US009809582B2

(12) United States Patent
Armani et al.

(10) Patent No.: US 9,809,582 B2
(45) Date of Patent: *Nov. 7, 2017

(54) AMINOESTER DERIVATIVES

(71) Applicant: CHIESI FARMACEUTICI S.p.A., Parma (IT)

(72) Inventors: Elisabetta Armani, Parma (IT); Gabriele Amari, Parma (IT); Wesley Blackaby, Saffron Walden (GB); Herve Van De Poel, Saffron Walden (GB); Charles Baker-Glenn, Saffron Walden (GB); Naimisha Trivedi, Saffron Walden (GB)

(73) Assignee: CHIESI FARMACEUTICI S.p.A., Parma (IT)

(*) Notice: Subject to any disclaimer, the term of this patent is extended or adjusted under 35 U.S.C. 154(b) by 0 days.

This patent is subject to a terminal disclaimer.

(21) Appl. No.: 15/148,225

(22) Filed: May 6, 2016

(65) Prior Publication Data

US 2016/0326147 A1 Nov. 10, 2016

(30) Foreign Application Priority Data

May 7, 2015 (EP) .................................... 15166703

(51) Int. Cl.
| A61K 31/4545 | (2006.01) |
| C07D 409/12 | (2006.01) |
| C07D 409/14 | (2006.01) |
| C07D 471/08 | (2006.01) |
| A61K 31/439 | (2006.01) |
| A61K 31/4436 | (2006.01) |
| A61K 31/4439 | (2006.01) |
| C07D 453/02 | (2006.01) |

(52) U.S. Cl.
CPC .......... *C07D 409/12* (2013.01); *A61K 31/439* (2013.01); *A61K 31/4436* (2013.01); *A61K 31/4439* (2013.01); *A61K 31/4545* (2013.01); *C07D 409/14* (2013.01); *C07D 453/02* (2013.01); *C07D 471/08* (2013.01)

(58) Field of Classification Search
USPC ......................................... 514/305, 318, 336
See application file for complete search history.

(56) References Cited

U.S. PATENT DOCUMENTS

| 9,090,606 B2* | 7/2015 | Armani | ................ C07D 453/02 |
| 9,133,185 B2* | 9/2015 | Amari | .................. C07D 409/14 |
| 9,145,409 B2 | 9/2015 | Amari et al. | |
| 9,169,245 B2 | 10/2015 | Armani et al. | |
| 9,199,980 B2 | 12/2015 | Armani et al. | |
| 9,326,976 B2 | 5/2016 | Armani et al. | |
| 2014/0155428 A1* | 6/2014 | Armani | ................ C07D 453/02 |
| | | | 514/305 |
| 2015/0352091 A1 | 12/2015 | Armani et al. | |

OTHER PUBLICATIONS

U.S. Appl. No. 15/168,425, filed May 31, 2016, Amari et al.
U.S. Appl. No. 15/168,438, filed May 31, 2016, Amari et al.

* cited by examiner

*Primary Examiner* — Pancham Bakshi
(74) *Attorney, Agent, or Firm* — Oblon, McClelland, Maier & Neustadt, L.L.P.

(57) ABSTRACT

Compounds of formula (I) are both phosphodiesterase 4 (PDE4) enzyme inhibitors and muscarinic M3 receptor antagonists and are useful for the prevention and/or treatment of diseases of the respiratory tract characterized by airway obstruction.

17 Claims, No Drawings

AMINOESTER DERIVATIVES

CROSS REFERENCES TO RELATED APPLICATIONS

This application claims priority to European Patent Application No. 15166703.7 filed on May 7, 2015, which is incorporated herein by reference in its entirety.

BACKGROUND OF THE INVENTION

Field of the Invention

The present invention relates to novel compounds which are both phosphodiesterase 4 (PDE4) enzyme inhibitors and muscarinic M3 receptor antagonists. In addition, the present invention relates to methods of preparing such a compound, compositions containing such a compound, and therapeutic uses of such a compound.

Discussion of the Background

Chronic obstructive pulmonary disease (COPD) is a respiratory disorder characterized by progressive, not fully reversible, airflow limitation associated with an abnormal pulmonary inflammatory response to noxious particles or gases.

For this reason, bronchial relaxation and inflammatory response suppression represent a mechanistic approach to the treatment of COPD that might improve symptoms such as dyspnea, wheezing, chest tightness, cough and mucus secretion, improve health status and reduce exacerbations.

Nowadays, the drug therapy options for COPD fall into two general classes: bronchodilators, (β2-adrenoceptor agonists, antimuscarinic agents, and methylxanthines) and antiinflammatory agents (glucocorticosteroids and selective phosphodiesterase-4 (PDE4) inhibitors).

Bronchodilator drugs are the current mainstay of treatment for relief of symptoms.

As anticholinergic bronchodilators, the efficacy of muscarinic M3 antagonists is based on the fact that the major reversible component of airflow narrowing in COPD patients is the increase of acetylcholine (ACh) released to airway smooth muscle, by the bronchial postganglionic vagal efferent in some pathological conditions. Therefore, compounds that antagonize the action of ACh at muscarinic receptors are able to counteract the bronchoconstriction and thus improve lung function in these patients.

Muscarinic antagonists block the effects of ACh at muscarinic receptors.

Currently, there are five known muscarinic receptor subtypes (M1-M5); human airway smooth muscle contains M1, M2, and M3 receptors. M1 receptors facilitate neurotransmission through parasympathetic ganglia and are weakly expressed on submucosal glands in human airways. The M2 receptors are located on the smooth-muscle fibers. Some studies have suggested a small role of M2 mediating the inhibition of airway smooth-muscle relaxation caused by adenylyl cyclase activation by compounds such as beta agonists. In addition, presynaptic M2 receptors are found on postganglionic parasympathetic nerves that project to airway smooth muscle and mucus-producing cells.

These presynaptic M2 autoreceptors provide a negative feedback mechanism, which, when stimulated, inhibit further release of ACh. Postsynaptic M3 receptors are known to mediate both contraction of smooth muscle in the respiratory tract and mucus secretion, making them a major target for symptomatic relief of COPD. Consequently, in the airways, the major effects of muscarinic antagonists are bronchodilation and reduction of mucus secretion via blockage of ACh-induced effects in the parasympathetic nervous system.

Given the distribution of muscarinic receptors, systemically available agents that bind to muscarinic receptors outside of the respiratory tract have the potential to produce unwanted side effects such as tachycardia, dry mouth, urinary retention and constipation. Whereas dry mouth is the most common systemic anticholinergic side effect associated with the use of antimuscarinic antagonists as a result of the systemic blockade of M1 and M3 receptors the most potentially serious systemic effect is tachycardia, which results from the blockade of cardiac M2 receptors.

Inhaled anticholinergic antimuscarinic drugs approved for the treatment of COPD include ipratropium bromide (Atrovent®), oxitropium bromide (Oxivent®) and tiotropium bromide (Spiriva®). Both ipratropium and oxitropium are short-acting agents. In contrast, tiotropium bromide is the only long-acting antimuscarinic agent (LAMA) currently marketed for COPD, proved to be suitable for once-daily administration as a dry powder. Several others newer LAMAs are newly registered for the treatment of COPD, including aclidinium bromide and glycopyrrolate bromide, or are currently in phase III development, including umeclidinium.

Although bronchodilators are quite effective to improve symptoms, they do not address the underlying chronic inflammation or the changes in airway structure.

Standard treatment with glucocorticosteroids as antiinflammatory agents has demonstrated limited efficacy. However, among the antiinflammatory agents currently being developed, PDE4 inhibitors proved to be effective in attenuating the responses of various inflammatory cells, through their ability to elevate cAMP levels.

PDE4 is the predominant PDE expressed in neutrophils and T cells, suggesting that PDE4 inhibitors would be effective in controlling inflammation in COPD. Inhibition of PDE4 in inflammatory cells influences various specific responses, such as the production and/or release of pro-inflammatory mediators including cytokines and reactive oxygen species, with a well-documented efficacy in animal models mimicking certain aspects of asthma and COPD, as well as inflammatory bowel disease, atopic dermatitis, psoriasis and rheumatoid arthritis.

The selective PDE4 inhibitor, roflumilast (Daxas®) is an approved phosphodiesterase-4 inhibitor for the treatment of COPD associated with chronic bronchitis and a history of exacerbations. Roflumilast inhibits lung inflammation and emphysema in a smoking model of COPD in mice. In COPD patients, oral roflumilast given over four weeks significantly reduces the numbers of neutrophils (by 36%) and CXCL8 concentrations in sputum. In clinical trials roflumilast (500 mg once daily) given over 12 months improved lung function in COPD patients to a small extent but had little effect in reducing exacerbations or improving quality of life. More recently roflumilast has been shown to significantly improve FEV 1 (by approximately 50 mL) and reduce exacerbation (by about 15%) in patients with severe disease who have frequent exacerbations and mucus hypersecretion. Roflumilast provides clinical benefit when added to salmeterol or tiotropium and so may be used as an additional treatment in patients with severe disease.

However, the clinical utility of PDE4 inhibitors has so far been compromised by the occurrence of mechanism-associated side effects, including headache, nausea and emesis, which often limited the maximally tolerated dose. This problem could be overcome by inhaled delivery and designing compounds with a potentially more advantageous therapeutic window.

Since bronchial relaxation and inflammatory response suppression represent a mechanistic approach to the treatment of COPD, the combination of muscarinic M3 antagonism with selective PDE4 inhibition may lead to a new class of drugs, combining both bronchodilating and antiinflammatory properties in one molecule, which may open new perspectives in the management of COPD.

WO 2014/086852, WO 2014/086849, WO 2014/086855, WO 2015/082616, and WO 2015/082619, all of which are incorporated herein by reference in their entireties, disclose compounds which exhibit both bronchodilating and antiinflammatory properties.

There remains, however, a need for additional compounds which are both phosphodiesterase 4 (PDE4) enzyme inhibitors and muscarinic M3 receptor antagonists.

SUMMARY OF THE INVENTION

Accordingly, it is one object of the present invention to provide novel compounds which are both phosphodiesterase 4 (PDE4) enzyme inhibitors and muscarinic M3 receptor antagonists.

It is another object of the present invention to provide novel methods of preparing such a compound.

It is another object of the present invention to provide novel compositions which contain such a compound.

It is another object of the present invention to provide novel therapeutic uses of such a compound.

These and other objects, which will become apparent during the following detailed description, have been achieved by the inventors' discovery that compounds of formula (I), shown below, exhibit the desired properties:

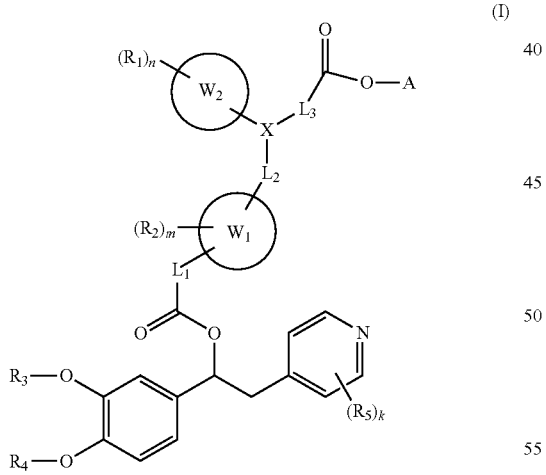

(I)

wherein
each $R_1$ is hydrogen or is independently selected from the group consisting of: halogen, $(C_1\text{-}C_4)$ alkyl, $(C_1\text{-}C_4)$ alkoxy, $(C_1\text{-}C_4)$ haloalkyl, hydroxy, $-SO_2NR_6R_7$, $-CN$, $-NR_8SO_2R_9$, $-NR_6R_7$, $-CONR_6R_7$ and $-NR_8COR_9$ and wherein said $(C_1\text{-}C_4)$ alkyl is optionally substituted by one or more groups selected from $(C_3\text{-}C_7)$ cycloalkyl, hydroxy and $-NR_6R_7$ and wherein said $(C_1\text{-}C_4)$ alkoxy is optionally substituted by one or more halogens or groups $(C_3\text{-}C_7)$ cycloalkyl wherein, $R_6$ is hydrogen or $(C_1\text{-}C_6)$ alkyl;
$R_7$ is hydrogen or $(C_1\text{-}C_6)$ alkyl;
$R_8$ is hydrogen or $(C_1\text{-}C_6)$ alkyl;
$R_9$ is hydrogen or $(C_1\text{-}C_6)$ alkyl;
n is an integer ranging from 1 to 3;
each $R_2$ is hydrogen or is selected from the group consisting of: halogen, $(C_1\text{-}C_4)$ alkyl, $(C_1\text{-}C_4)$ alkoxy, $(C_1\text{-}C_4)$ haloalkyl, hydroxy, $-CN$ and $-NR_{12}SO_2R_{13}$ and wherein said $(C_1\text{-}C_4)$ alkyl and said $(C_1\text{-}C_4)$ alkoxy are optionally substituted by one or more group $(C_3\text{-}C_7)$ cycloalkyl wherein
$R_{10}$ is hydrogen or $(C_1\text{-}C_6)$ alkyl;
$R_{11}$ is hydrogen or $(C_1\text{-}C_6)$ alkyl;
$R_{12}$ is hydrogen or $(C_1\text{-}C_6)$ alkyl;
$R_{13}$ is hydrogen or $(C_1\text{-}C_6)$ alkyl;
m is an integer ranging from 1 to 3;
$R_3$ and $R_4$ are different or the same and are independently selected from the group consisting of: H, $(C_3\text{-}C_7)$ cycloalkylcarbonyl, $(C_1\text{-}C_6)$ alkyl optionally substituted by one or more substituents selected from $(C_1\text{-}C_4)$ alkoxy, $(C_3\text{-}C_7)$ cycloalkyl or $(C_5\text{-}C_7)$ cycloalkenyl, $(C_1\text{-}C_6)$ haloalkyl, $(C_3\text{-}C_7)$ cycloalkyl, $(C_5\text{-}C_7)$ cycloalkenyl, $(C_2\text{-}C_6)$ alkenyl, and $(C_2\text{-}C_6)$ alkynyl;
each $R_5$, whenever present, is independently selected from the group consisting of: CN, $NO_2$, $CF_3$ and halogen atoms;
k is 0 or an integer ranging from 1 to 3;
$L_1$ is a bond
$W_1$ is selected from a divalent arylene and a heteroarylenegroup;
$W_2$ is selected from an aryl and a heteroaryl;
$L_2$ is a group selected from $-(CH_2)_q-$ wherein q is an integer ranging from 1 to 4;
$L_3$ is a bond or a group selected from $-(CH_2)_s-$ wherein s is 1 or 2;
X is a group selected from $X_1$, $X_2$ and $X_3$:

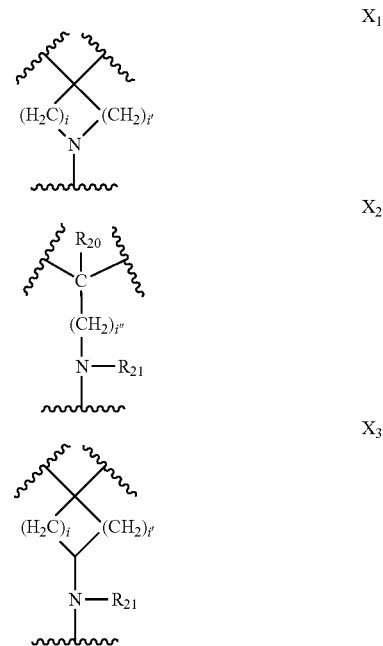

wherein
$R_{20}$ is selected in the group consisting of H, OH, $(C_1\text{-}C_4)$ alkyl, wherein said $(C_1\text{-}C_4)$ alkyl is optionally substituted by one or more hydroxyl, $R_{21}$ is selected from hydrogen, ($C_1$-$C_6$) alkyl optionally substituted by hydroxyl;
and wherein
i is 1 or 2;
i' is 1 or 2;
i" is an integer ranging from 1 to 4;
A is selected from:
a group —$(CH_2)_s$—$NR_{16}R_{17}$ wherein s is an integer ranging from 1 to 4 and $R_{16}$ and $R_{17}$ are independently selected from hydrogen or ($C_1$-$C_4$) alkyl; and
a saturated monocyclic, bicyclic or tricyclic heterocyclic ring system containing one N heteroatom or $NR_{18}$ group wherein $R_{18}$ is selected from ($C_1$-$C_4$) alkyl and benzyl;
their N-oxides on the pyridine ring, deuterated derivatives; and pharmaceutically acceptable salts, or solvates thereof.

The present invention further concerns the corresponding N-oxides on the pyridine ring of compounds of formula (I) which are represented by the formula (I)'

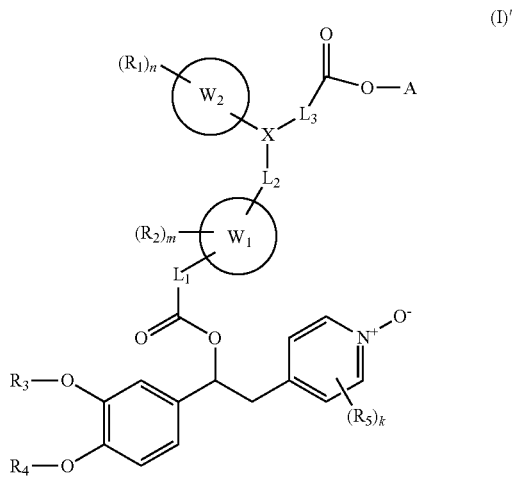

wherein $R_1$, $R_2$, $R_3$, $R_4$, $R_5$, $L_1$, $W_1$, $L_2$, $W_2$, X, $L_3$, A, m, n, and k are as described above.

The present invention further provides the corresponding deuterated derivatives of compounds of formula (I) wherein at least one hydrogen atom is substituted by corresponding atoms of deuterium.

In the context of the present invention, the term deuterated derivative means that the at least one position occupied by a hydrogen atom is occupied by deuterium in an amount above its natural abundance. Preferably, the percent of deuterium at that position is at least 90%, more preferably at least 95%, even more preferably 99%. Preferably deuterated derivatives according to the invention are deuterated at available positions in the substituent $R_3$.

The present invention also encompasses the pharmaceutically acceptable salts and/or solvates thereof.

The term "pharmaceutically acceptable salts" refers to derivatives of compounds of formula (I) or of their corresponding N-oxides on the pyridine ring wherein the parent compound is suitably modified by converting any of the free acid or basic group, if present, into the corresponding addition salt with any base or acid conventionally intended as being pharmaceutically acceptable.

Suitable examples of said salts may include mineral or organic acid addition salts of basic residues such as amino groups, as well as mineral or organic acid residues such as carboxylic groups.

Cations of inorganic bases which can be suitably used to prepare salts within the invention comprise ions of alkali or alkaline earth metals such as potassium, sodium, calcium, or magnesium.

Those obtained by reacting the main compound, functioning as a base, with an inorganic or organic acid to form a salt comprise, for example, salts of hydrochloric acid, hydrobromic acid, sulfuric acid, phosphoric acid, acetic acid, methane sulfonic acid, camphor sulfonic acid, oxalic acid, maleic acid, fumaric acid, succinic acid, and citric acid.

The skilled person will appreciate that many organic compounds can form complexes with solvents in which they are reacted or from which they are precipitated or crystallized. These complexes are known as "solvates". Pharmaceutically acceptable solvates of compound of the invention are within the scope of the invention.

Included within the scope of the present invention are also polymorphs and crystalline forms of compounds of formula (I), of their N-oxides on the pyridine ring, or of pharmaceutically acceptable salts, or solvates thereof.

Hereinafter, compounds of formula (I), (IA), (IB), (IC), (ID), (Ia), (Ib), (Ic), (Id) (Ie), (If), (Ig), (Ih), (I') and (I)", corresponding N-oxides on the pyridine ring, enantiomers, diastereoisomers thereof, their pharmaceutically acceptable salts and solvates, and polymorphs or crystalline forms thereof defined in any aspect of the invention (except intermediate compounds described in the chemical processes) are referred to as "compounds of the invention".

The present invention further provides processes for the preparation of compounds of the invention.

The present invention also provides pharmaceutical compositions of compounds of the invention either alone or in combination, in admixture with one or more pharmaceutically acceptable carriers.

In a further aspect the present invention provides the use of the compounds of the invention as a medicament.

In one aspect, the present invention provides the use of the compounds of the invention for the manufacture of a medicament.

In particular, the present invention provides the use of the compounds of the invention for the prevention and/or treatment of any disease wherein an inhibition of PDE4 activity along with muscarinic M3 receptor antagonism is desirable.

In particular the compounds of the invention alone or combined in a composition comprising other active ingredients may be administered for the prevention and/or treatment of a disease the respiratory tract characterized by airway obstruction such as asthma and COPD. In one embodiment, the compounds of the invention may be administered for the prevention and/or treatment of COPD.

In a further aspect, the present invention provides the use of compounds of the invention for the preparation of a medicament for the prevention and/or treatment of any disease wherein an inhibition of PDE4 activity along with muscarinic M3 receptor antagonism is desirable.

Moreover the present invention provides a method for prevention and/or treatment of any disease wherein an inhibition of PDE4 activity along with muscarinic M3 receptor antagonism is desirable, said method comprises administering to a patient in need of such treatment a therapeutically effective amount of a compound of the invention.

A further aspect of the present invention provides a suitable inhalation device, comprising a pharmaceutical composition of a compound of the invention, which may be respectively selected from a single- or multi-dose dry powder inhaler, a pressurized metered dosed inhaler or a nebulizer and in particular a soft mist nebulizer.

A further aspect of the present invention provides a kit comprising a pharmaceutical composition containing a compound of the invention either alone or in combination with one or more active ingredient and a device which may be a single- or multi-dose dry powder inhaler, a metered dose inhaler or a nebulizer.

DETAILED DESCRIPTION OF THE PREFERRED EMBODIMENTS

The term "halogen atoms" includes fluorine, chlorine, bromine, and iodine, preferably chlorine.

The term "$(C_1-C_x)$ alkyl" where x is an integer greater than 1, refers to straight and branched chain alkyl groups wherein the number of constituent carbon atoms is in the range 1 to x. Particular alkyl groups are methyl, ethyl, n-propyl, i-propyl, n-butyl, sec-butyl, i-butyl, and t-butyl.

By analogy, the term "$(C_1-C_x)$alkylene" refers to a divalent $(C_1-C_x)$alkyl radical, wherein $(C_1-C_x)$alkyl is as above defined.

The term "$(C_1-C_x)$ alkoxy" where x is an integer greater than 1 refers to straight and branched chain alkoxy groups wherein the number of constituent carbon atoms is in the range 1 to x. Particular alkoxy groups are methoxy, ethoxy, n-propoxy, i-propoxy, n-butoxy, sec-butoxy, i-butoxy, and t-butoxy.

The expression "$(C_1-C_x)$haloalkyl" refers to the above defined "$(C_1-C_x)$alkyl" groups wherein one or more hydrogen atoms are replaced by one or more halogen atoms, which can be the same or different from each other.

Examples of said $(C_1-C_6)$haloalkyl groups may thus include halogenated, poly-halogenated and fully halogenated alkyl groups wherein all of the hydrogen atoms are replaced by halogen atoms, e.g. trifluoromethyl or difluoro methyl groups.

The term "$(C_3-C_y)$ cycloalkyl", where y is an integer greater than or equal to 3, refers to saturated cyclic hydrocarbon groups containing from 3 to y ring carbon atoms. Examples include cyclopropyl, cyclobutyl, cyclopentyl, cyclohexyl, and cycloheptyl.

The expression "$(C_3-C_y)$cycloalkylcarbonyl" refers to $(C_3-C_y)$cycloalkylCO— groups wherein the group "$(C_3-C_y)$ cycloalkyl" has the meaning above defined.

The term "$(C_2-C_6)$alkenyl" refers to straight or branched, conjugated or non-conjugated, carbon chains with one or more double bonds, in cis or trans configuration, wherein the number of atoms is in the range 2 to 6.

The term "$(C_5-C_z)$ cycloalkenyl", where z is an integer greater than or equal to 5, refers to cyclic hydrocarbon groups containing from 5 to z ring carbon atoms and one or more double bonds.

The term "$(C_2-C_6)$alkynyl" refers to straight or branched carbon chains with one or more triple bonds wherein the number of atoms is in the range 2 to 6.

The expression "$(C_5-C_6)$ heteroarylene" refers to divalent monocyclic ring systems with 5 to 6 ring atoms, and in which at least one ring atom is a heteroatom (e.g. N, NH, S, or O). Non-limiting examples of suitable $(C_5-C_6)$ heteroarylene systems include, for instance, thiophenediyl, furanediyl, pyrrolediyl, pyrazolediyl, imidazolediyl, triazolediyl, tetrazolediyl, isoxazolediyl, oxazolediyl, isothiazolediyl, thiazolediyl, pyridinediyl radicals at any suitable position and the like.

The term "aryl" refers to mono or bi-cyclic systems which have 6 to 10 ring carbon atoms, wherein at least one ring is aromatic.

The expression "heteroaryl" refers to mono or bi-cyclic systems with 5 to 11 ring atoms, in which at least one ring is aromatic and in which at least one ring atom is a heteroatom (e.g. N, NH, S, or O).

Examples of suitable aryl or heteroaryl monocyclic systems with 5 to 6 ring atoms include, for instance, benzene (phenyl), thiophene (thiophenyl), pyrrole (pyrrolyl), pyrazole (pyrazolyl), imidazole (imidazolyl), triazole (triazolyl), tetrazole (tetrazolyl), isoxazole (isoxazolyl), oxazole (oxazolyl), isothiazole (isothiazolyl), thiazole (thiazolyl), pyridine (pyridinyl), furan (furanyl) derived radicals and the like.

Examples of suitable aryl or heteroaryl bicyclic systems with more than 6 ring atoms include naphthalene (naphthalenyl), biphenylene (biphenylenyl), tetrahydronaphthalene (tetrahydronaphthalenyl), purine (purinyl), pteridine (preridinyl), benzimidazole (benzimidazolyl), benzotriazole (benzotriazolyl), quinoline (quinolinyl), isoquinoline (iosquinolinyl), indole (indolyl), isoindole (isoindolyl), indazole (indazolyl), benzothiophene (benzothiopnenyl), benzofuran (benzofuranyl), benzoxazole (benzoxazolyl), dihydrobenzo dioxin, dihydrobenzo dioxepin, benzo-oxazin radicals and the like.

The expression "heterocyclic ring system" refers to optionally substituted mono-, bi- or tri-cyclic ring systems which may be saturated, partially unsaturated or unsaturated, such as $(C_3-C_7)$ heterocycloalkyl or heteroaryl having 5 to 11 ring atoms in which at least one ring atom is a heteroatom (e.g. N, S, or O), included in the definition are bridged mono-, bi- or tri-cyclic ring systems.

Examples of "heterocyclic ring system" are represented by: pyrrolidinyl, imidazolidinyl, piperazinyl, piperidinyl, quinuclidinyl, 8-azabicyclo[3.2.1]octanyl or dehydroxy scopine radical all optionally substituted by $(C_1-C_x)$ alkyl or benzyl on a nitrogen atom.

The present invention is directed to a class of compounds acting both as inhibitors of the phosphodiesterase 4 (PDE4) enzyme and as muscarinic M3 receptor antagonists.

The present invention provides compounds of general formula (I), N-oxides on the pyridine ring, deuterated derivatives and pharmaceutically acceptable salts or solvates thereof,

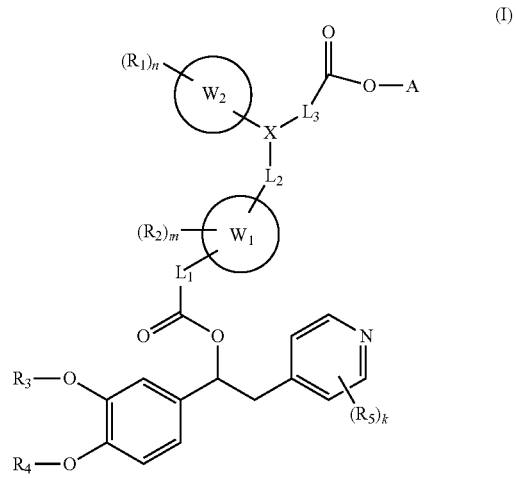

(I)

wherein $R_1$, $R_2$, $R_3$, $R_4$, $R_5$, $L_1$, $W_1$, $L_2$, $W_2$, X, $L_3$, A, n, m and k are as above defined.

Preferred compounds are those of formula (I), wherein $W_1$ is heteroarylene;

$W_2$ is selected from an aryl and a heteroaryl;

$L_2$ is a group selected from —$(CH_2)_q$— wherein q is an integer ranging from 1 to 4;

their N-oxides on the pyridine ring, deuterated derivatives;

and pharmaceutically acceptable salts, or solvates thereof.

Further preferred compounds of formula (I) are those wherein the saturated heterocyclic ring system A is represented by a group of formula (i), (ii), (iii) or (iv):

(i)

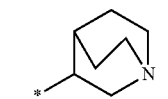

(ii)

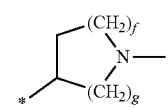

(iii)

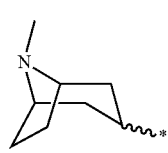

(iv)

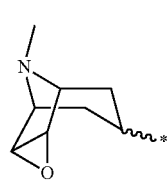

wherein f=1, 2 or 3;

g=1, 2 or 3;

and the asterisk (*) represents the point of attachment to the oxygen atom of formula (I).

It will be apparent to those skilled in the art that compounds of formula (I) contain at least one stereogenic center, namely represented by the carbon atom (1) in formula (I)" below, and therefore exist as optical stereoisomers.

It will also be apparent to the skilled person that compounds according to the present invention may have at least two stereogenic centers. Thus they may accordingly exist at least as four diastereoisomers. Where the compounds according to the invention possess more than two stereogenic centers, they will exist as $2^n$ diastereoisomers (wherein n here refers to the number of stereogenic centers). It is to be understood that all such isomers and mixtures thereof in any proportion are encompassed within the scope of the present invention.

In a preferred embodiment, the present invention is directed to compounds of formula (I)", which are compounds of formula (I) as above defined where the absolute configuration of carbon (1) is that shown below:

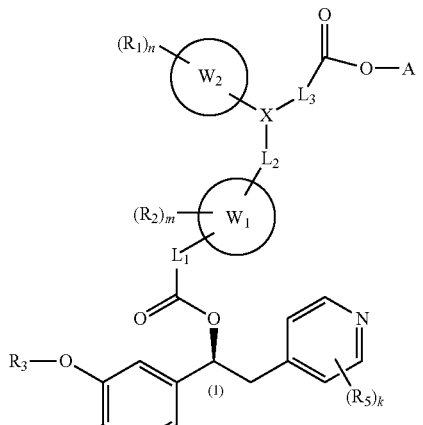

(I)"

The absolute configuration for carbon (1) is assigned on the basis of Cahn-Ingold-Prelog nomenclature based on groups' priorities.

In one preferred embodiment, for compounds of formula (I), the absolute configuration at carbon (1) is (S).

In one embodiment, when A is a group of formula (i) as above defined, or a group of formula (ii) containing a stereogenic carbon atom at the point of attachment of the oxygen atom of formula (I), compounds of formula (I) may exist as at least four diastereoisomers (Ia), (Ib), (Ic), and (Id), when A is (i), and (Ie), (If), (Ig), and (Ih), when A is (ii) herebelow reported, which are comprised within the scope of the present invention; when X is the group $X_2$, or the groups $X_1$ and $X_3$ wherein i and i' are different from each other, each (Ia), (Ib), (Ic), (Id), (Ie), (If), (Ig), and (Ih) is constituted by a couple of corresponding epimers at stereogenic center at the carbon atom of group X.

(Ia)

(Ib)
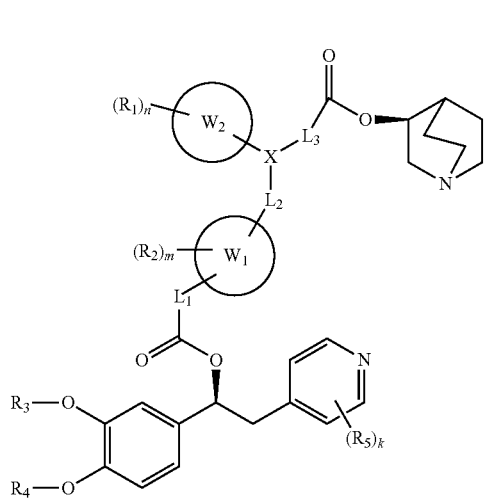
(Ic)
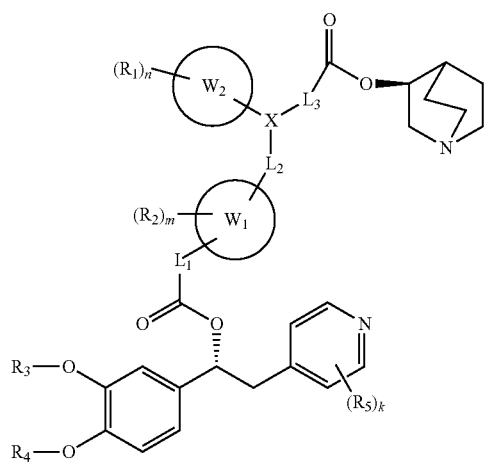
(Id)
(Ie)
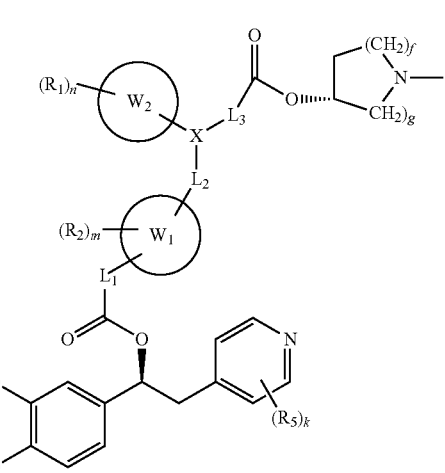
(If)
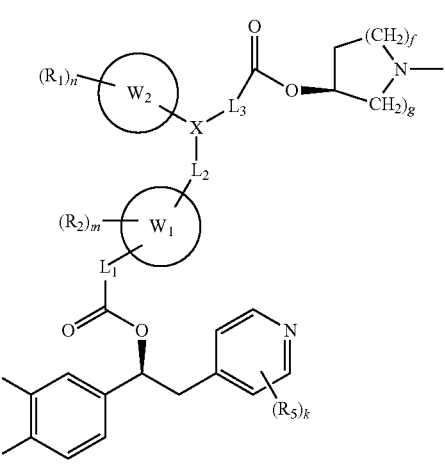
(Ig)
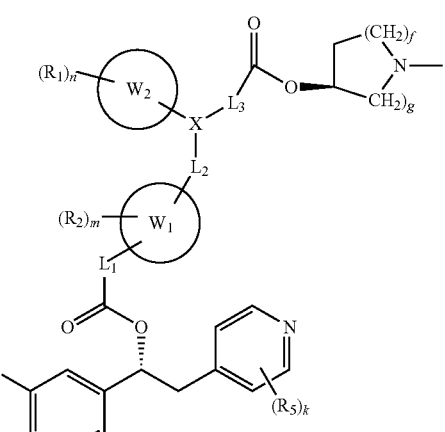

the pyridine ring of compounds of formula (I) wherein $L_3$ is a bond, X is the group $X_1$, deuterated derivatives and pharmaceutically acceptable salts and solvates thereof:

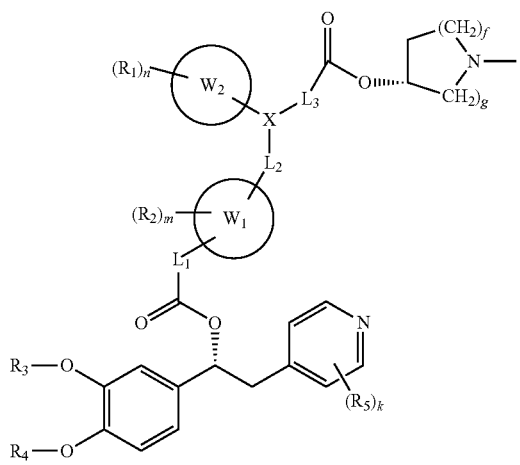

(Ih)

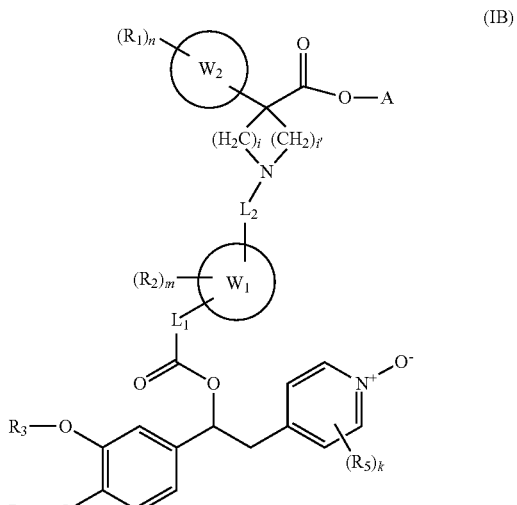

(IB)

It will be apparent to the skilled person that compounds of formula (Ia), (Ib), (Ic), (Id), (Ie), (If), (Ig), and (Ih) may be also obtained as single diastereoisomers wherein, when X contains a stereogenic centre at carbon atom, said stereogenic centre is defined as R or S.

In one embodiment, compounds of formula (Ia) are provided as above reported, or as a single diastereoisomers thereof.

It is to be understood that all preferred groups or embodiments described herebelow and hereabove for compounds of formula (I) may be combined among each other and apply to compounds of formula (IA), (IB), (IC), (ID), (Ia), (Ib), (Ic), (Id), (Ie), (If), (Ig), (Ih), (I)' and (I)" as well mutatis mutandis.

In a preferred embodiment, the present invention provides compounds of formula (IA), which are N-oxides on the pyridine ring of compounds of formula (I) wherein $L_3$ is a bond, X is the group $X_2$ and i" is 1, deuterated derivatives and pharmaceutically acceptable salts and solvates thereof:

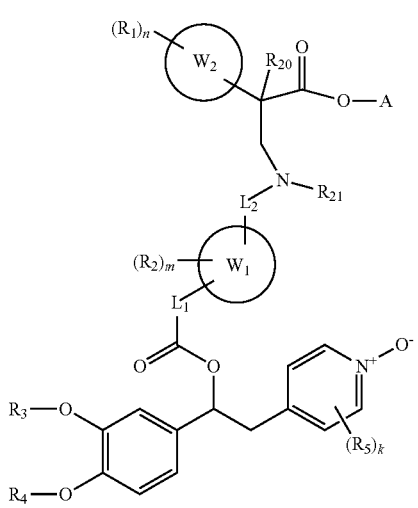

(IA)

wherein $R_1$, $R_2$, $R_3$, $R_4$, $R_5$, $R_{20}$, $R_{21}$, $L_1$, $W_1$, $L_2$, $W_2$, A, m, n, and k are as described above.

In another preferred embodiment the present invention provides compounds of formula (IB), which are N-oxides on wherein $R_1$, $R_2$, $R_3$, $R_4$, $R_5$, $L_1$, $W_1$, $L_2$, $W_2$, A, i, i', m, n, and k are as described for formula (I).

In another preferred embodiment the present invention provides compounds of formula (IE), which are N-oxides on the pyridine ring of compounds of formula (I) wherein $L_3$ is a bond, X is the group $X_3$, deuterated derivatives and pharmaceutically acceptable salts and solvates thereof:

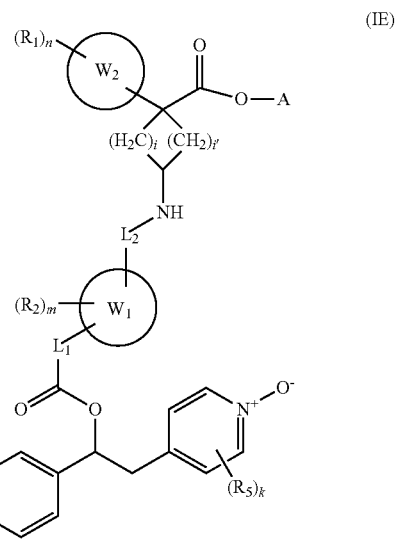

(IE)

wherein $R_1$, $R_2$, $R_3$, $R_4$, $R_5$, $L_1$, $W_1$, $L_2$, $W_2$, A, i, i', m, n, and k are as described for formula (I).

In a preferred embodiment of formulae (IA), (IB), or (IE), k is 2 and $R_5$ are halogen atoms. In a further preferred embodiment, $R_5$ are two chlorine atoms at positions 3 and 5 of the pyridine ring.

In one preferred embodiment, $R_4$ is selected from a $(C_1$-$C_6)$ alkyl and $R_3$ is selected from $(C_3$-$C_7)$ cycloalkyl or $(C_1$-$C_6)$ alkyl which is optionally substituted by $(C_3$-$C_7)$ cycloalkyl.

In another preferred embodiment, $R_3$ is $(C_1-C_6)$ alkyl and $R_4$ is $(C_1-C_6)$ alkyl.

In another preferred embodiment, $R_3$ and $R_4$ are both methyl.

A preferred group of compounds of formula (I) is that wherein the 4-pyridinyl ring is substituted in 3 and 5 with two atoms of chlorine, according to the general formula (IC):

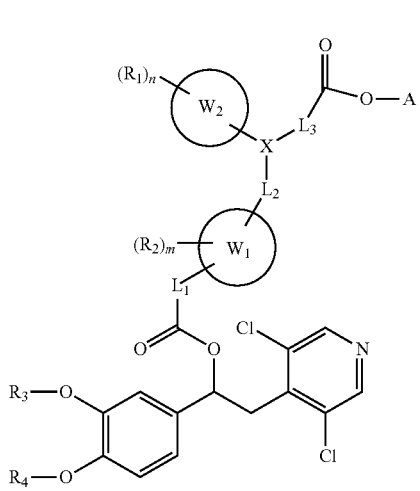

(IC)

wherein $R_1$, $R_2$, $R_3$, $R_4$, A, $L_1$, $W_1$, $L_2$, $W_2$, X, $L_3$, m and n are as defined above for compounds of formula (I); and the corresponding N-oxide on the pyridine ring, deuterated derivatives and pharmaceutically acceptable salts and solvates thereof.

A more preferred group of compounds is that shown below according to general formula (ID):

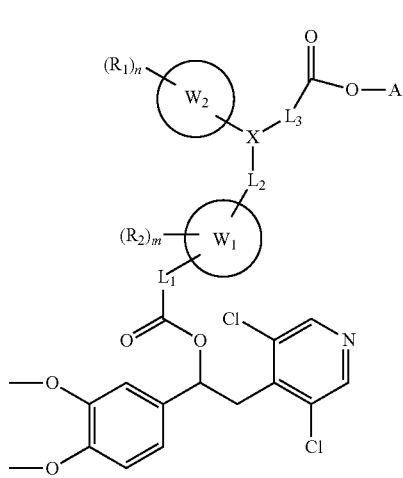

(ID)

wherein $R_1$, $R_2$, A, $L_1$, $W_1$, $L_2$, $W_2$, X, $L_3$, m and n are as defined above for compounds of formula (I), the corresponding N-oxide on the pyridine ring, deuterated derivatives and pharmaceutically acceptable salts and solvates thereof.

In one embodiment of formula (ID), both $L_1$ and $L_3$ are a bond.

In another embodiment of formula (ID), m is 0 and $W_1$ is phenylene-1,4-diyl, phenylene-1,3-diyl or thienylene-2,5-diyl; alternatively named 1,4-phenylene, 1,3-phenylene, thiophene-2,5-diyl.

In another embodiment of formula (ID), n is 0 and $W_2$ is unsubstituted phenyl.

In another embodiment of formula (ID), X is a group of formula $X_1$ wherein both i and i' are 1 or 2, or a group of formula $X_2$ wherein i" is 1 and $R_{20}$ and $R_{21}$ are independently selected form H or methyl, or a group of formula $X_3$ wherein both i and i' are 1 and $R_{21}$ is H.

In another embodiment of formula (ID), A is a group of formula (i) or (ii):

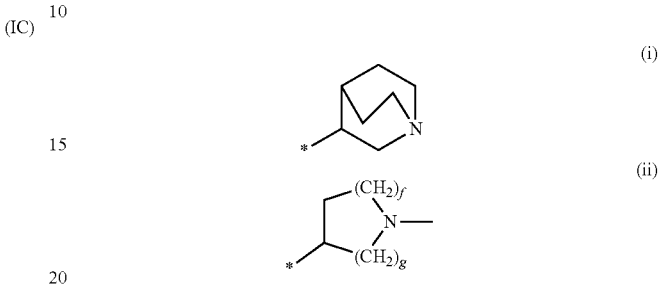

wherein f is 1 and g is 1 or f is 1 and g is 2, or A is the group —$CH_2CH_2N(CH_3)_2$.

According to a preferred embodiment, the present invention provides the compounds reported below:

[(1S)-2-(3,5-dichloro-1-oxido-pyridin-1-ium-4-yl)-1-(3,4-dimethoxyphenyl)ethyl] 5-[[[3-oxo-2-phenyl-3-[(3R)-quinuclidin-3-yl]oxy-propyl]amino]methyl]thiophene-2-carboxylate;

[(1S)-2-(3,5-dichloro-1-oxido-pyridin-1-ium-4-yl)-1-(3,4-dimethoxyphenyl)ethyl] 4-[[[3-oxo-2-phenyl-3-[(3R)-quinuclidin-3-yl]oxy-propyl]amino]methyl]benzoate;

[(3R)-quinuclidin-3-yl] 1-[[5-[(1S)-2-(3,5-dichloro-1-oxido-pyridin-1-ium-4-yl)-1-(3,4-dimethoxyphenyl)ethoxy]carbonyl-2-thienyl]methyl]-4-phenyl-piperidine-4-carboxylate;

[(1S)-2-(3,5-dichloro-1-oxido-pyridin-1-ium-4-yl)-1-(3,4-dimethoxyphenyl)-ethyl]-5-[[[3-[(3R)-1-methylpyrrolidin-3-yl]oxy-3-oxo-2-phenyl-propyl]amino]methyl]-thiophene-2-carboxylate;

[(1S)-2-(3,5-dichloro-1-oxido-pyridin-1-ium-4-yl)-1-(3,4-dimethoxyphenyl)ethyl] 5-[[[3-[(1-methyl-4-piperidyl)oxy]-3-oxo-2-phenyl-propyl]amino]methyl]thiophene-2-carboxylate;

[(1S)-2-(3,5-dichloro-1-oxido-pyridin-1-ium-4-yl)-1-(3,4-dimethoxyphenyl)ethyl] 5-[[[3-(2-dimethylaminoethyloxy)-3-oxo-2-phenyl-propyl]amino]methyl]thiophene-2-carboxylate;

[(1S)-2-(3,5-dichloro-1-oxido-pyridin-1-ium-4-yl)-1-(3,4-dimethoxyphenyl)ethyl] 5-[[[2-methyl-3-oxo-2-phenyl-3-[(3R)-quinuclidin-3-yl]oxy-propyl]amino]methyl]-thiophene-2-carboxylate;

[(1S)-2-(3,5-dichloro-1-oxido-pyridin-1-ium-4-yl)-1-(3,4-dimethoxyphenyl)ethyl] 5-[[[2-methyl-3-[(1-methyl-4-piperidyl)oxy]-3-oxo-2-phenyl-propyl]amino]methyl]-thiophene-2-carboxylate;

[(1S)-2-(3,5-dichloro-1-oxido-pyridin-1-ium-4-yl)-1-(3,4-dimethoxyphenyl)ethyl] 5-[[[3-(2-dimethylaminoethyloxy)-2-methyl-3-oxo-2-phenyl-propyl]amino]methyl]-thiophene-2-carboxylate;

[(1S)-2-(3,5-dichloro-1-oxido-pyridin-1-ium-4-yl)-1-(3,4-dimethoxyphenyl)-ethyl]-5-[[methyl-[2-methyl-3-oxo-2-phenyl-3-[(3R)-quinuclidin-3-yl]oxy-propyl]-amino]methyl]thiophene-2-carboxylate;

[(3R)-quinuclidin-3-yl]-1-[[4-[(1S)-2-(3,5-dichloro-1-oxido-pyridin-1-ium-4-yl)-1-(3,4-dimethoxyphenyl)ethoxy]-carbonylphenyl]methyl]-4-phenyl-piperidine-4-carboxylate;

[(3R)-quinuclidin-3-yl]-1-[2-[4-[(1S)-2-(3,5-dichloro-1-oxido-pyridin-1-ium-4-yl)-1-(3,4-dimethoxyphenyl)ethoxy]carbonylphenyl]ethyl]-4-phenyl-piperidine-4-carboxylate;

[(3R)-quinuclidin-3-yl] 1-[2-[3-[(1S)-2-(3,5-dichloro-1-oxido-pyridin-1-ium-4-yl)-1-(3,4-dimethoxyphenyl)ethoxy]carbonylphenyl]ethyl]-4-phenyl-piperidine-4-carboxylate;

[(3R)-quinuclidin-3-yl]-1-[[3-[(1S)-2-(3,5-dichloro-1-oxido-pyridin-1-ium-4-yl)-1-(3,4-dimethoxyphenyl)ethoxy]carbonylphenyl]methyl]-4-phenyl-piperidine-4-carboxylate;

[(3R)-quinuclidin-3-yl]-1-[[5-[(1S)-2-(3,5-dichloro-1-oxido-pyridin-1-ium-4-yl)-1-(3,4-dimethoxyphenyl)ethoxy]carbonyl-2-thienyl]methyl]-3-phenyl-azetidine-3-carboxylate;

[(3R)-1-methylpyrrolidin-3-yl] 1-[[5-[(1S)-2-(3,5-dichloro-1-oxido-pyridin-1-ium-4-yl)-1-(3,4-dimethoxyphenyl)ethoxy]carbonyl-2-thienyl]methyl]-3-phenyl-azetidine-3-carboxylate;

Single diastereoisomer of [(1S)-2-(3,5-dichloro-1-oxido-pyridin-1-ium-4-yl)-1-(3,4-dimethoxyphenyl)ethyl] 5-[[[2-hydroxy-3-oxo-3-[(3R)-quinuclidin-3-yl]oxy-2-(2-thienyl)propyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]-5-[[[3-oxo-2-phenyl-3-[(3R)-quinuclidin-3-yl]oxypropyl]amino]-methyl]thiophene-2-carboxylate (diastereoisomer 1);

Single diastereoisomer 2 of [(1S)-2-(3,5-dichloro-1-oxido-pyridin-1-ium-4-yl)-1-(3,4-dimethoxyphenyl)ethyl]-5-[[[3-oxo-2-phenyl-3-[(3R)-quinuclidin-3-yl]oxypropyl]amino]-methyl]thiophene-2-carboxylate (diastereoisomer 2);

Single diastereoisomer 1 of [(1S)-2-(3,5-dichloro-1-oxido-pyridin-1-ium-4-yl)-1-(3,4-dimethoxyphenyl)ethyl]-5-[[[2-hydroxy-3-oxo-2-phenyl-3-[(3R)-quinuclidin-3-yl]oxy-propyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl] 5-[[[2-hydroxy-3-oxo-2-phenyl-3-[(3R)-quinuclidin-3-yl]oxy-propyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl] 5-[[[3-(2-dimethylaminoethyloxy)-3-oxo-2-phenyl-propyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl] 5-[[[3-(2-dimethylaminoethyloxy)-3-oxo-2-phenyl-propyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl] 5-[[[2-methyl-3-[(1-methyl-4-piperidyl)oxy]-3-oxo-2-phenyl-propyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl] 5-[[[2-methyl-3-[(1-methyl-4-piperidyl)oxy]-3-oxo-2-phenyl-propyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl] 5-[[methyl-[2-methyl-3-oxo-2-phenyl-3-[(3R)-quinuclidin-3-yl]oxy-propyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl] 5-[[methyl-[2-methyl-3-oxo-2-phenyl-3-[(3R)-quinuclidin-3-yl]oxy-propyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl] 5-[[[3-(2-dimethylaminoethyloxy)-2-methyl-3-oxo-2-phenyl-propyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl] 5-[[[3-(2-dimethylaminoethyloxy)-2-methyl-3-oxo-2-phenyl-propyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl] 5-[[[2-methyl-3-oxo-2-phenyl-3-[(3R)-quinuclidin-3-yl]oxy-propyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl] 5-[[[2-methyl-3-oxo-2-phenyl-3-[(3R)-quinuclidin-3-yl]oxy-propyl]amino]methyl]thiophene-2-carboxylate;

[(1S)-2-(3,5-dichloro-1-oxido-pyridin-1-ium-4-yl)-1-(3,4-dimethoxyphenyl)ethyl] 5-[[[3-[(1-methyl-4-piperidyl)oxycarbonyl]-3-phenyl-cyclobutyl]amino]methyl]-thiophene-2-carboxylate;

Single diastereoisomer 1 of [(1S)-2-(3,5-dichloro-1-oxido-pyridin-1-ium-4-yl)-1-(3,4-dimethoxyphenyl)ethyl] 5-[[[3-[(1-methyl-4-piperidyl)oxycarbonyl]-3-phenyl-cyclobutyl]amino]methyl]-thiophene-2-carboxylate;

Single diastereoisomer 2 of [(1S)-2-(3,5-dichloro-1-oxido-pyridin-1-ium-4-yl)-1-(3,4-dimethoxyphenyl)ethyl] 5-[[[3-[(1-methyl-4-piperidyl)oxycarbonyl]-3-phenyl-cyclobutyl]amino]methyl]-thiophene-2-carboxylate;

[(1S)-2-(3,5-dichloro-1-oxido-pyridin-1-ium-4-yl)-1-(3,4-dimethoxyphenyl)ethyl] 5-[[[3-phenyl-3-[(3R)-quinuclidin-3-yl]oxycarbonyl-cyclobutyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl] 5-[[[3-phenyl-3-[(3R)-quinuclidin-3-yl]oxycarbonyl-cyclobutyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl] 5-[[[3-phenyl-3-[(3R)-quinuclidin-3-yl]oxycarbonyl-cyclobutyl]amino]methyl]thiophene-2-carboxylate;

the corresponding N-oxide on the pyridine ring, deuterated derivatives and pharmaceutically acceptable salts and solvates thereof.

The expression "single diastereoisomer" is reported near the chemical name of each compound of formula (I) isolated as single diastereoisomer whose absolute configuration at the stereogenic carbon atom of X was not determined.

The present invention also concerns processes for the preparation of compounds of the invention.

Compounds of formula (IA), (IB) and compounds of formula (IE) can be obtained according to general synthetic routes of Scheme A, Scheme B, and scheme D, respectively, below reported or following slightly modified procedures that the skilled person can easily apply.

Processes of preparation described below and reported in the following Scheme A, Scheme B, and scheme D should not be viewed as limiting the scope of the synthetic methods available for the preparation of the compounds of the invention.

In the following Scheme A, Scheme B, and Scheme D, for compounds of formula (IA), (IB), and (IE) and for compounds of formula (II) to (XXX), unless otherwise indicated, $R_1$, $R_2$, $R_3$, $R_4$, $R_5$, $R_{20}$, $R_{21}$, $L_1$, $W_1$, $L_2$, $W_2$, A, n, m, k and are as above defined, whereas Y is a bond or $CH_2$.

Scheme A:
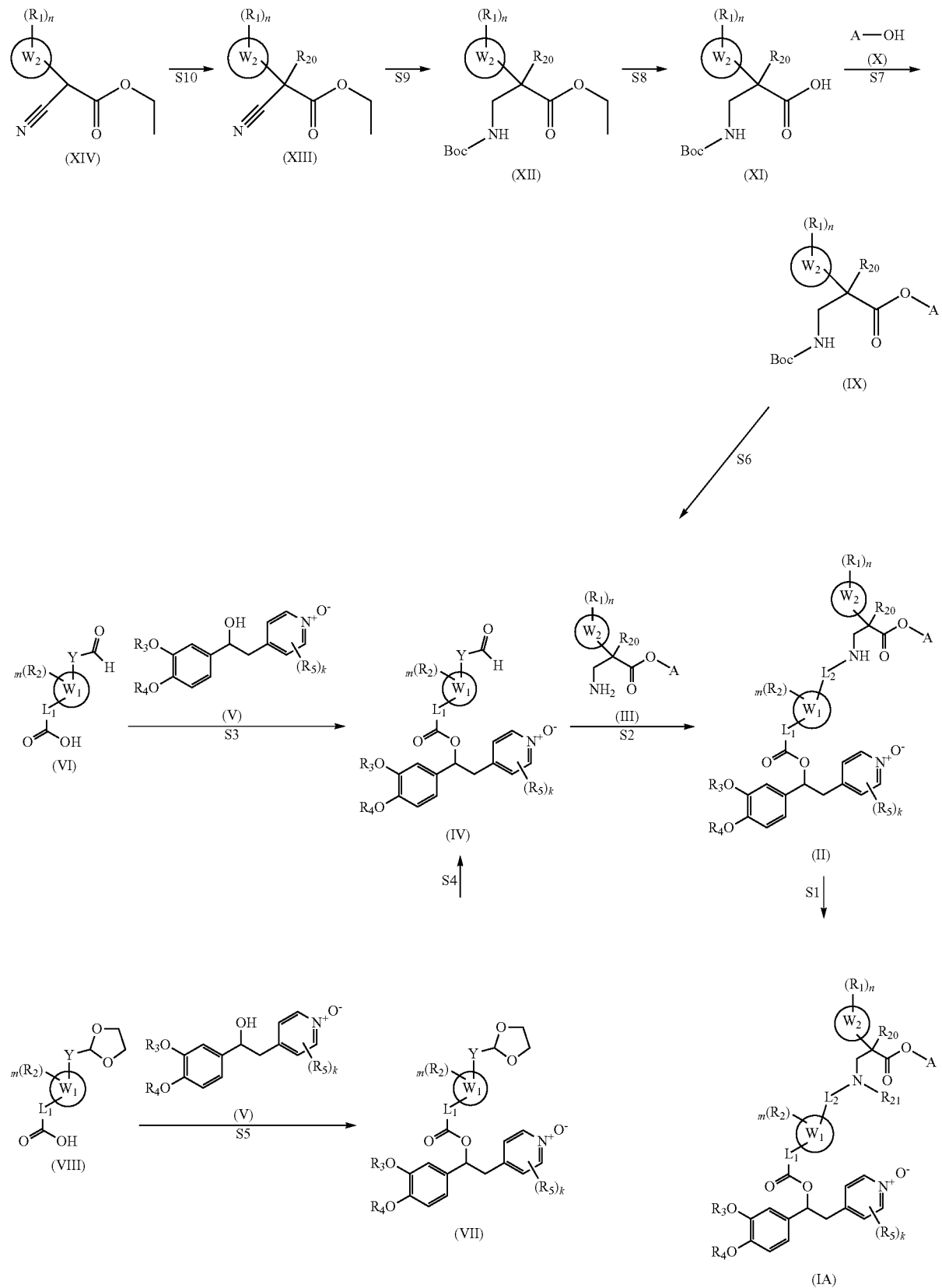

Compounds of formula (IA) may be prepared according to Scheme 1/(S1) below by reaction of a compound of formula (II) as below reported.

Compounds of formula (II) may be prepared according to Scheme 2/(S2) below by reaction of a compound of formula (IV) with a compound of formula (III) as below reported.

Scheme 1 (S1):

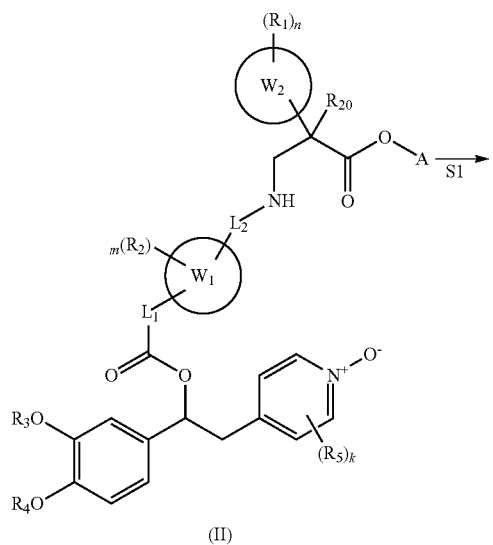

(II)

Scheme 2:

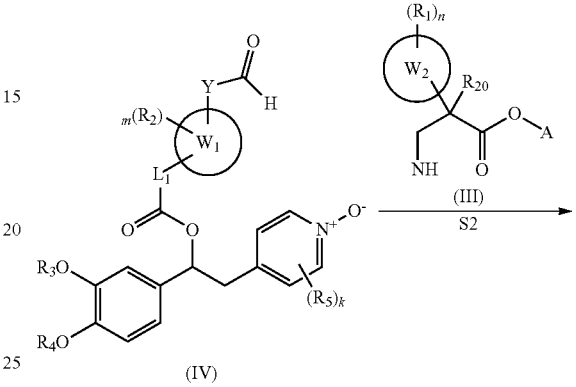

(S2)

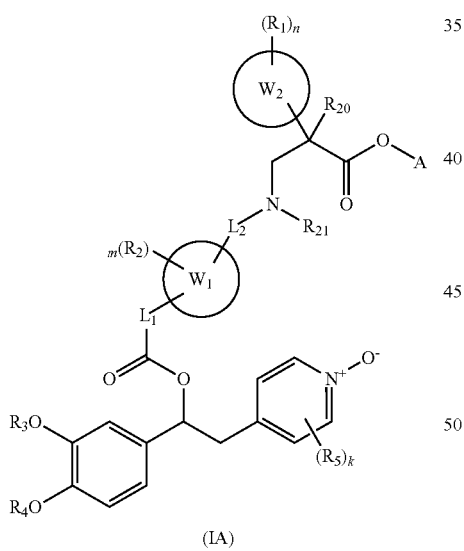

(IA)

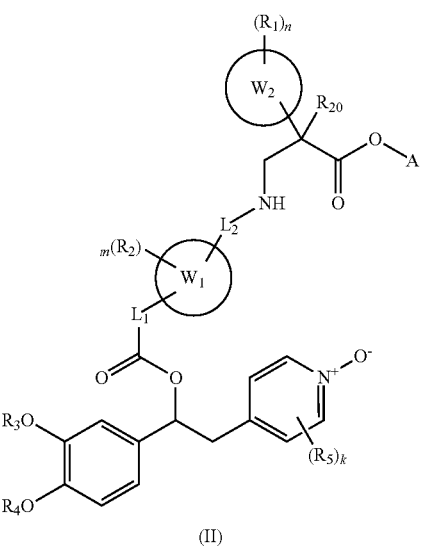

(II)

Typical reaction conditions comprise reacting a compound of formula (II) with an aldehyde, such as formaldehyde, in a suitable solvent, such as acetonitrile, DCM or ethanol in the presence of an acid, such as formic acid, and a reducing agent, such as NaB(OAc)$_3$H or NaBH$_3$CN, at an appropriate temperature, such as room (or ambient) temperature or 40° C.

Typical reaction conditions comprise reacting a compound of formula (IV) with a compound of formula (HI) in a suitable solvent, such as acetonitrile, DCM or ethanol in the presence of an acid, such as acetic acid, and an optional base, such as triethylamine, and a reducing agent, such as NaB(OAc)$_3$H or NaBH$_3$CN, at an appropriate temperature, such as room (or ambient) temperature or 0° C. or 40° C.

Compounds of formula (IV) may be prepared according to Scheme 3/(S3) below by reaction of a compound of formula (VI) with a compound of formula (V) as below reported.

Scheme 3 (S3):

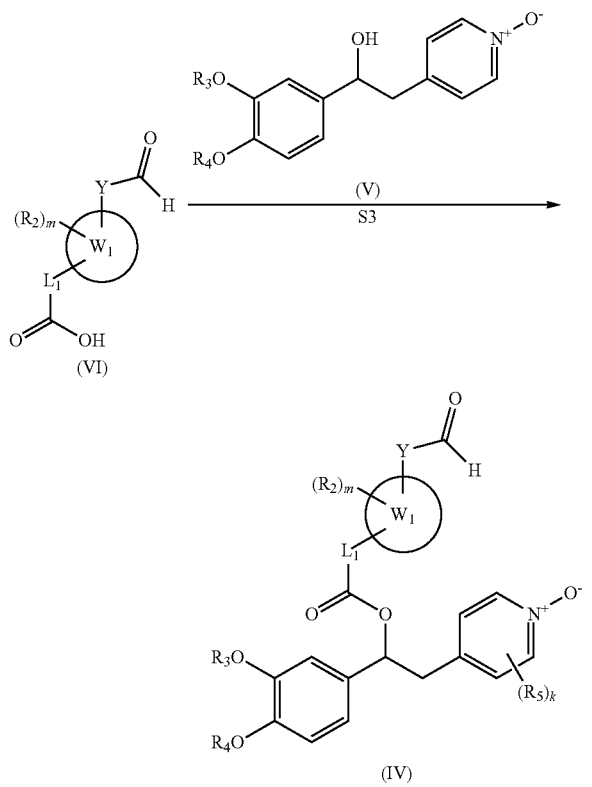

Typical reaction conditions comprise reacting a compound of formula (VI), with a compound of formula (V) in a suitable solvent, such as DCM, in the presence of a suitable coupling agent, such as EDC/DMAP or HATU, at an appropriate temperature, such as room (or ambient) temperature.

Compounds of formula (V) may be prepared as described in the co-pending International Patent Application No. PCT/EP2013/075520, which is incorporated herein by reference in its entirety.

Compounds of formula (IV) may also be prepared according to Scheme 4/(S4) below by reaction of a compound of formula (VII) as below reported.

Scheme 4 (S4):

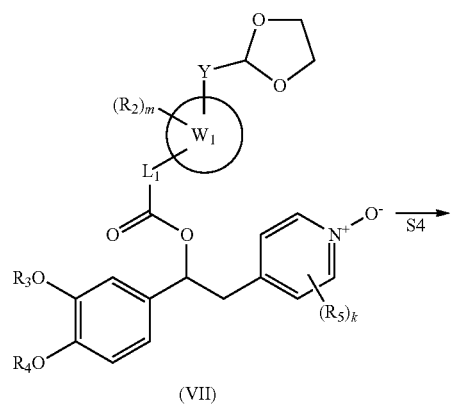

Typical reaction conditions comprise reacting a compound of formula (VII) in a suitable solvent, such as THF, in the presence of a suitable acid, such as hydrochloric acid, at an appropriate temperature, such as room (or ambient) temperature.

Compounds of formula (VII) may be prepared according to Scheme 5/(S5) below by reaction of a compound of formula (VIII) with a compound of formula (V) as below reported.

Scheme 5 (S5):

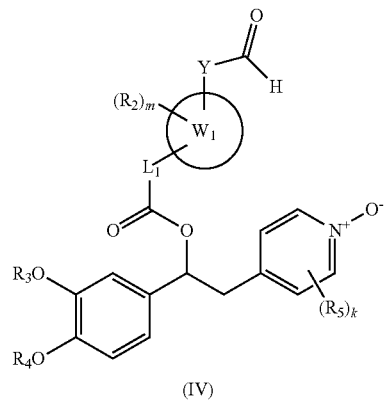

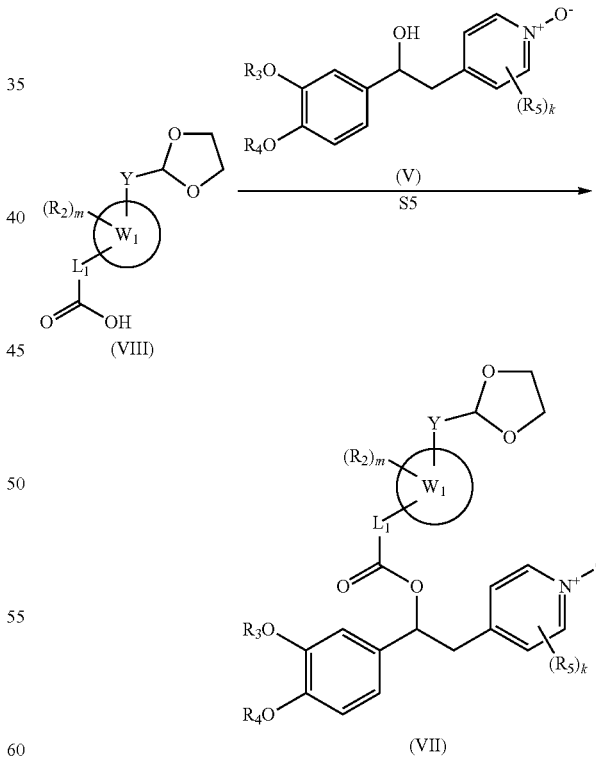

Typical reaction conditions comprise reacting a compound of formula (VIII) with a compound of formula (V) in a suitable solvent, such as DCM, in the presence of a suitable coupling agent, such as EDC/DMAP or HATU, at an appropriate temperature, such as room (or ambient) temperature.

Compounds of formula (V) may be prepared as described in the co-pending International Patent Application No. PCT/EP2013/075520, which is incorporated herein by reference in its entirety.

Compounds of formula (III) may be prepared according to Scheme 6/(S6) below by reaction of a compound of formula (IX) as below reported.

Scheme 6 (S6):

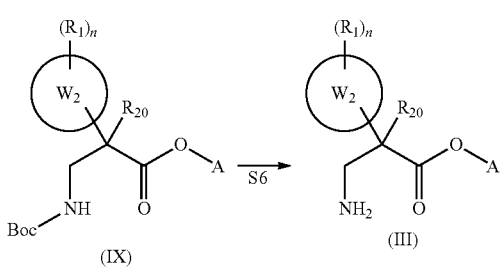

Typical reaction conditions comprise reacting a compound of formula (IX) in a suitable solvent, such as 1,4-dioxane, in the presence of a suitable acid, such as hydrochloric acid, at an appropriate temperature, such as room (or ambient) temperature.

Compounds of formula (IX) may be prepared according to Scheme 7/(S7) below by reaction of a compound of formula (XI) with a compound of formula (X) as below reported.

Scheme 7 (S7):

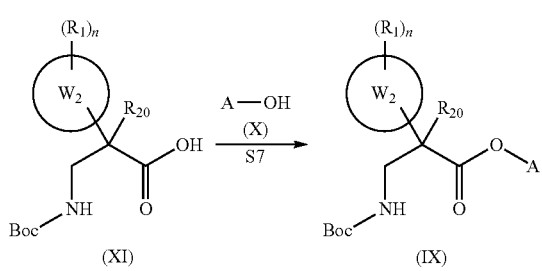

Typical reaction conditions comprise reacting a compound of formula (XI) with a compound of formula (X) in a suitable solvent, such as THF in the presence of a suitable coupling agent, such as DCC/HOBt or EDC/DMAP or HATU, at an appropriate temperature, such as room (or ambient) temperature or 40° C.

Compounds of formula (XI) may be prepared according to Scheme 8/(S8) below by reaction of a compound of formula (XII) as below reported.

Scheme 8 (S8):

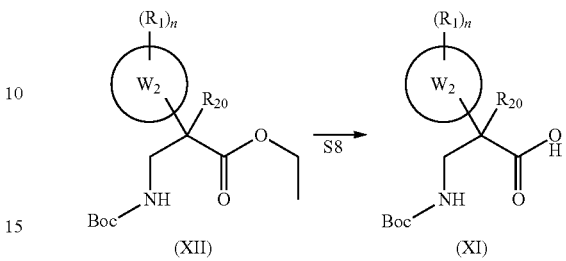

Typical reaction conditions comprise reacting compound of formula (XII) with a suitable base, such as LiOH in a suitable solvent, such as MeOH at an appropriate temperature, such as room (or ambient) temperature or 50° C.

Compounds of formula (XII) may be prepared according to Scheme 9/(S9) below by reaction of a compound of formula (XIII) as below reported.

Scheme 9 (S9):

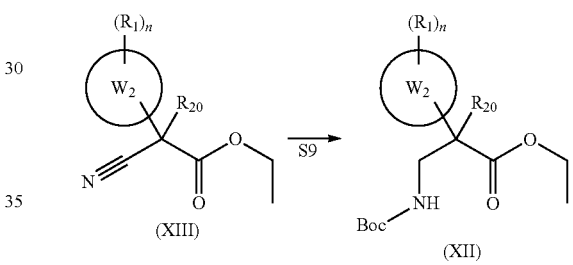

Typical reaction conditions comprise reacting compound of formula (XIII) with $CoCl_2 \cdot 6H_2O$ in a suitable solvent, such as MeOH in the presence of di-tert-butyl dicarbonate and a reducing agent, such as sodium borohydride at an appropriate temperature, such as room (or ambient) temperature or 50° C.

Compounds of formula (XIII) may be prepared according to Scheme 10/(S10) below by reaction of a compound of formula (XIV) as below reported.

Scheme 10 (S10):

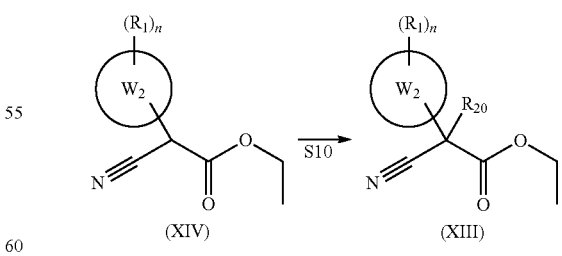

Typical reaction conditions comprise reacting a compound of formula (XIV) with an alkylating agent, such as iodomethane, in a suitable solvent, such as THF or 1,4-dioxane, in the presence of a suitable base such as sodium hydride, at an appropriate temperature, such as 0° C. or room (or ambient) temperature.

Scheme B
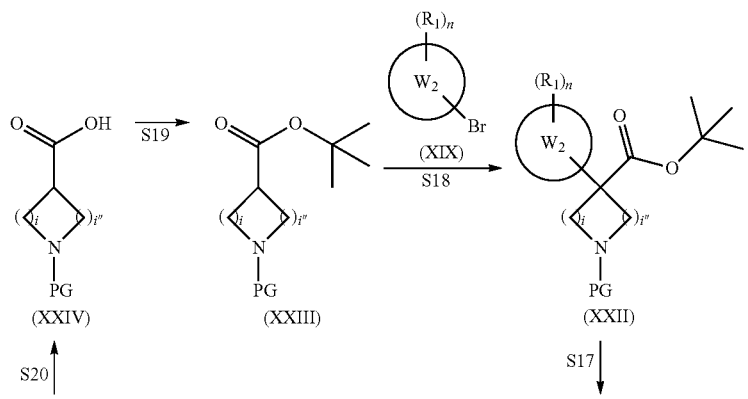
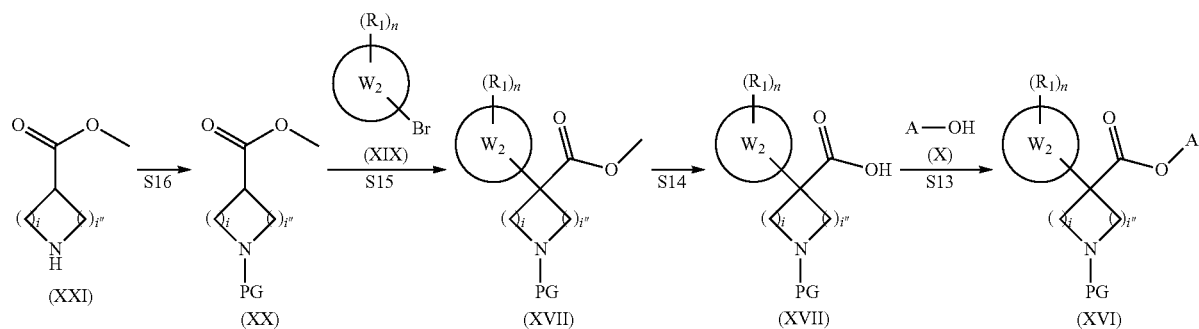
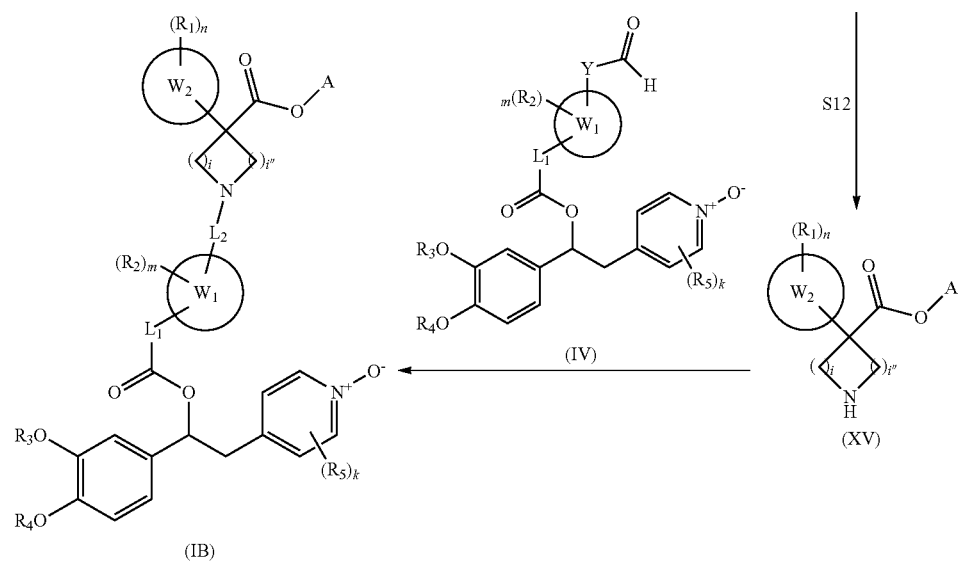

Compounds of formula (IB) may be prepared according to Scheme 11/(S11) below by reaction of a compound of formula (XV) with a compound of formula (IV) as below reported.

Scheme 11 (S11):

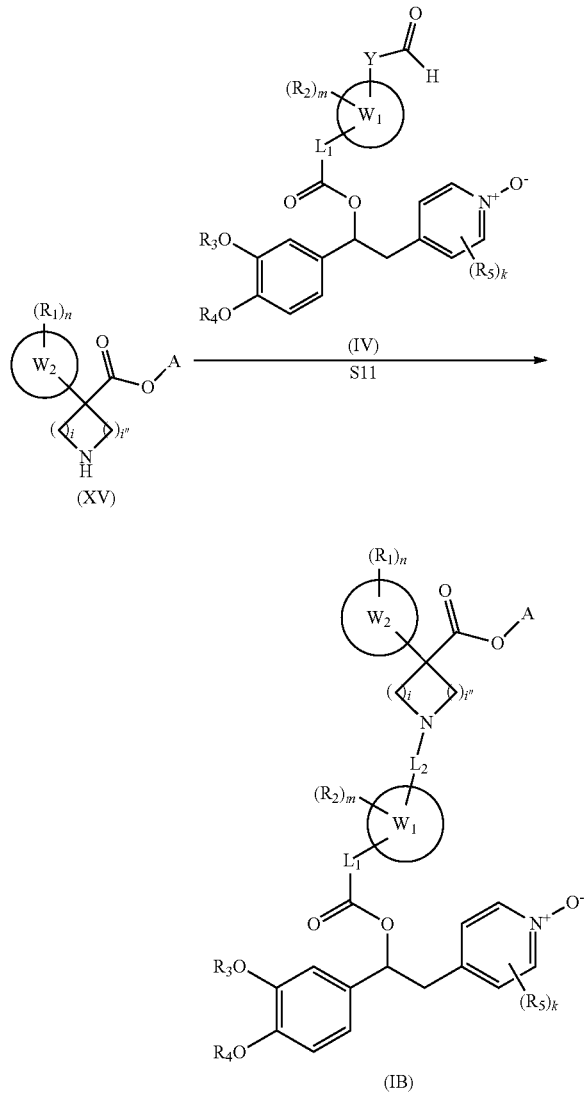

Typical reaction conditions comprise reacting a compound of formula (XV) with a compound of formula (IV) in a suitable solvent, such as acetonitrile, DCM or ethanol in the presence of an acid, such as acetic acid, and an optional base, such as triethylamine, and a reducing agent, such as NaB(OAc)$_3$H or NaBH$_3$CN, at an appropriate temperature, such as room (or ambient) temperature or 0° C. or 40° C.

Compounds of formula (XV) may be prepared according to Scheme 12/(S12) below by reaction of a compound of formula (XVI), wherein PG is a protecting group which can be removed by hydrogenolysis or protonolysis such as, for example, the benzyloxycarbonyl group, as below reported.

Scheme 12 (S12):

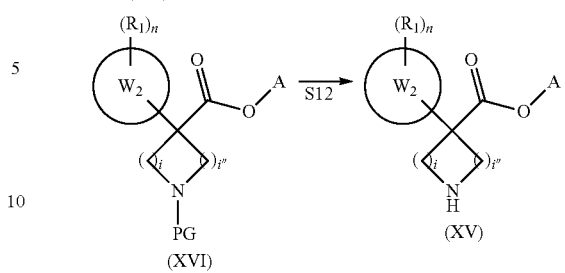

Typical reaction conditions comprise reacting a compound of formula (XVI) with a source of hydrogen, such as ammonium formate or gaseous hydrogen over a suitable catalyst, such as 10% Pd/C, in a suitable solvent, such as EtOAc, at an appropriate temperature, such as room (or ambient) temperature.

Compounds of formula (XV) may also be prepared by reacting a compound of formula (XVI) in a suitable solvent, such as 1,4-dioxane, in the presence of a suitable acid, such as hydrochloric acid, at an appropriate temperature, such as room (or ambient) temperature.

Compounds of formula (XVI) may be prepared according to Scheme 13/(S13) below by reaction of a compound of formula (XVII) with a compound of formula (X) as below reported.

Scheme 13 (S13):

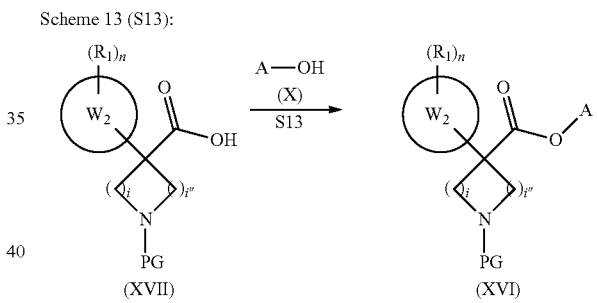

Typical reaction conditions comprise reacting a compound of formula (XVII) with a compound of formula (X) in a suitable solvent, such as THF in the presence of a suitable coupling agent, such as DCC/HOBt or EDC/DMAP or HATU, at an appropriate temperature, such as room (or ambient) temperature or 40° C.

Compounds of formula (XVII) may be prepared according to Scheme 14/(S14) below by reaction of a compound of formula (XVIII) as below reported.

Scheme 14 (S14):

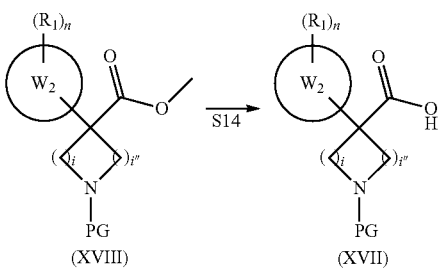

Typical reaction conditions comprise reacting compound of formula (XVIII) with a suitable base, such as NaOH or LiOH in a suitable solvent, such as MeOH at an appropriate temperature, such as room (or ambient) temperature or 50° C.

Compounds of formula (XVIII) may be prepared according to Scheme 15/(S15) below by reaction of a compound of formula (XX) with a compound of formula (XIX) as below reported.

Scheme 15 (S15):

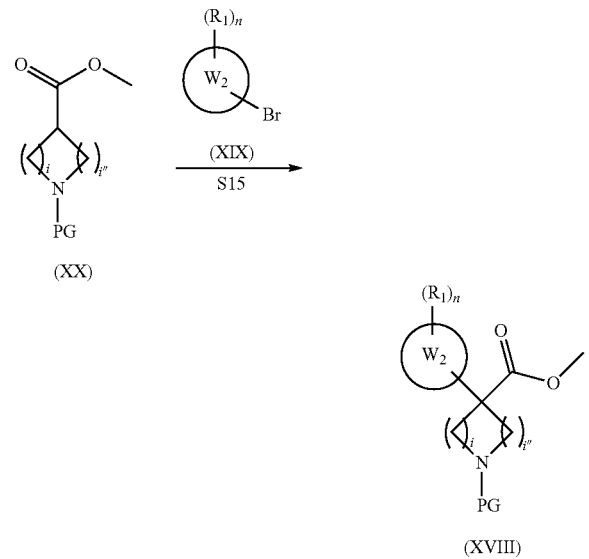

Typical reaction conditions comprise reacting a compound of formula (XX) with an aryl halide, such as bromobenzene, in a suitable solvent, such as toluene, in the presence of a palladium catalyst, such as $Pd_2(dba)_3$, a trialkyl phosphine ligand, such as $[HP(tBu_3)]BF_4$, and a suitable base, such as LiHMDS, at an appropriate temperature, such as room (or ambient) temperature or 0° C.

Compounds of formula (XX) may be prepared according to Scheme 16/(S16) below by reaction of a compound of formula (XXI) as below reported.

Scheme 16 (S16):

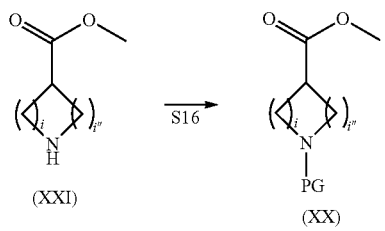

Typical reaction conditions comprise reacting a compound of formula (XXI) with an electrophile, such as benzyl chloroformate, in a suitable solvent, such as THF/water or 1,4-dioxane/water, in the presence of a suitable base such as sodium hydroxide, at an appropriate temperature, such as 0° C. or room (or ambient) temperature.

Compounds of formula (XVII) may also be prepared according to Scheme 17/(S17) below by reaction of a compound of formula (XXII) as below reported.

Scheme 17 (S17):

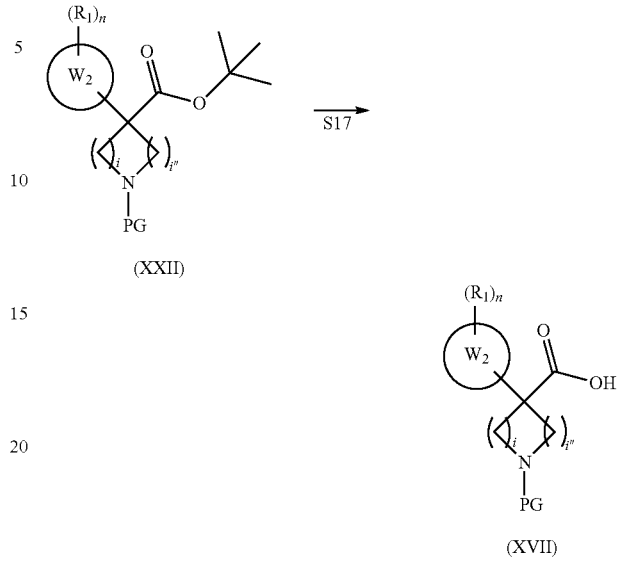

Typical reaction conditions comprise reacting a compound of formula (XXII) in a suitable solvent, such as 1,4-dioxane, in the presence of a suitable acid, such as hydrochloric acid, at an appropriate temperature, such as room (or ambient) temperature.

Compounds of formula (XXII) may be prepared according to Scheme 18/(S18) below by reaction of a compound of formula (XXIII) with a compound of formula (XIX) as below reported.

Scheme 18 (S18):

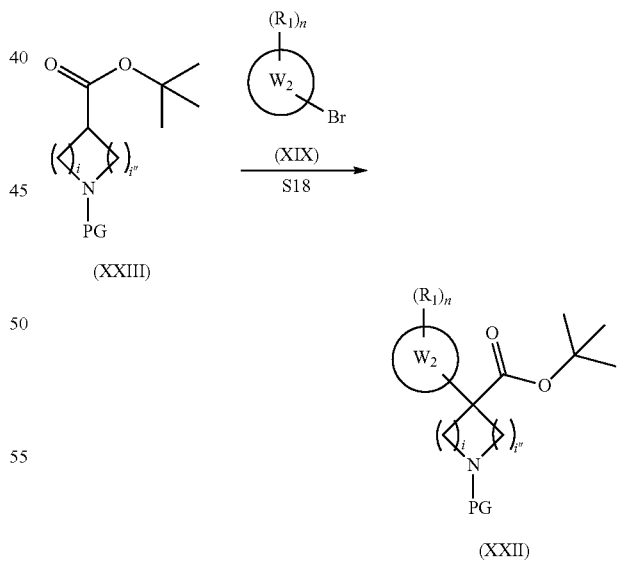

Typical reaction conditions comprise reacting a compound of formula (XXIII) with an aryl halide, such as bromobenzene, in a suitable solvent, such as toluene, in the presence of a palladium catalyst, such as $Pd_2(dba)_3$, a phosphine ligand, such as $[HP(tBu_3)]BF_4$, and a suitable base, such as LiHMDS, at an appropriate temperature, such as room (or ambient) temperature or 0° C.

Compounds of formula (XXIII) may be prepared according to Scheme 19/(S19) below by reaction of a compound of formula (XXIV) as below reported.

Scheme 19 (S19):

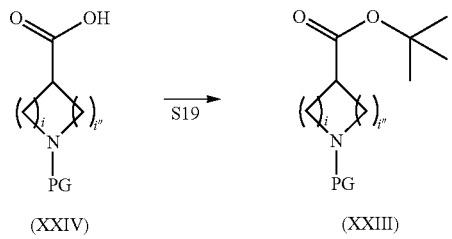

(XXIV) → (XXIII)

Typical reaction conditions comprise reacting a compound of formula (XXIV) with tert-butyl alcohol in a suitable solvent, such as THF or DCM in the presence of a suitable coupling agent, such as DCC/HOBt or EDC/DMAP or HATU, at an appropriate temperature, such as room (or ambient) temperature or 40° C.

Compounds of formula (XXIV) may be prepared according to Scheme 20/(S20) below by reaction of a compound of formula (XX) as below reported.

Scheme 20 (S20):

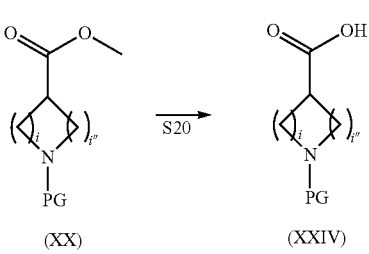

(XX) → (XXIV)

Typical reaction conditions comprise reacting compound of formula (XX) with a suitable base, such as NaOH in a suitable solvent, such as MeOH at an appropriate temperature, such as room (or ambient) temperature or 50° C.

Scheme D

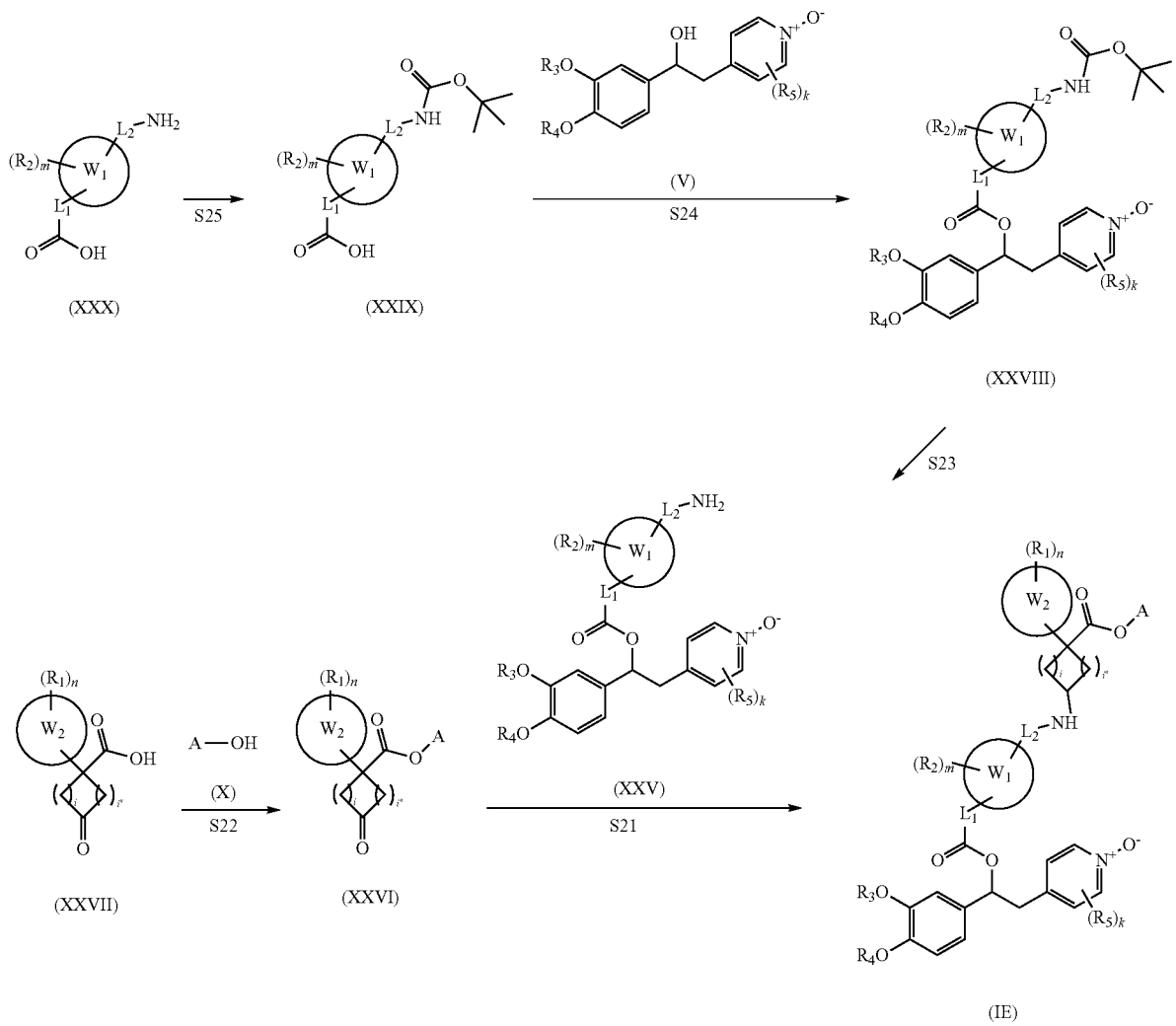

Compounds of formula (IE) may be prepared according to Scheme 21/(S21) below by reaction of a compound of formula (XXV) with a compound of formula (XXVI) as below reported.

Scheme 21 (S21):

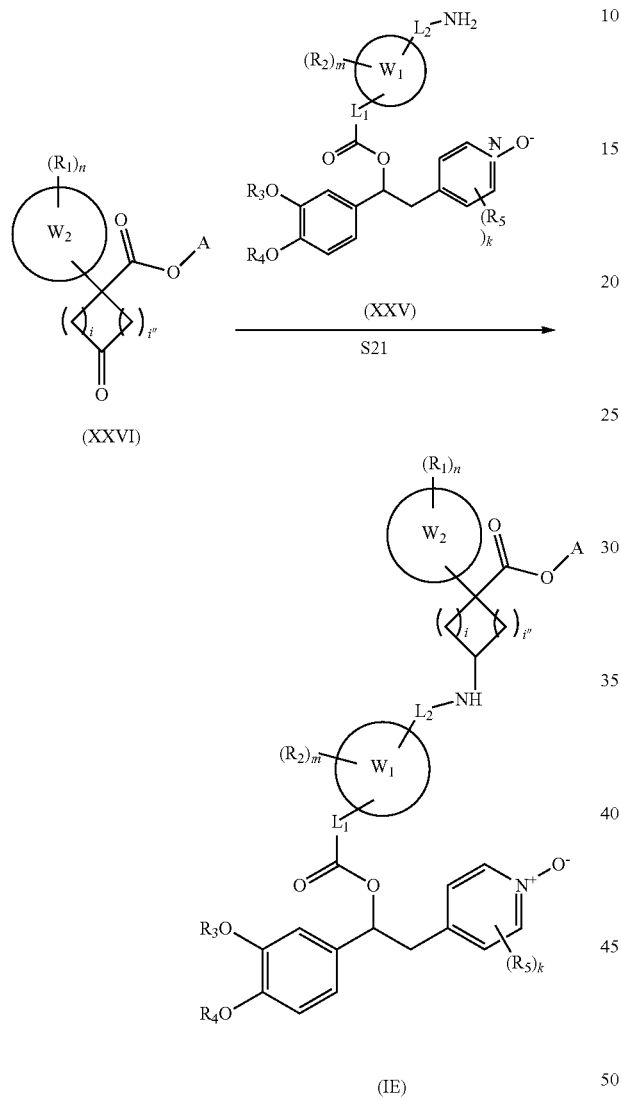

(IE)

Typical reaction conditions comprise reacting a compound of formula (XXV) with a compound of formula (XXVI), in a suitable solvent, such as trifluoroethanol in the presence of an acid, such as acetic acid, and a reducing agent, such as $NaB(OAc)_3H$ or $NaBH_3CN$, at an appropriate temperature, such as room (or ambient) temperature or 40° C.

Compounds of formula (XXVI) may be prepared according to Scheme 22/(S22) below by reaction of a compound of formula (XXVII) with a compound of formula (X) as below reported.

Scheme 22 (S22):

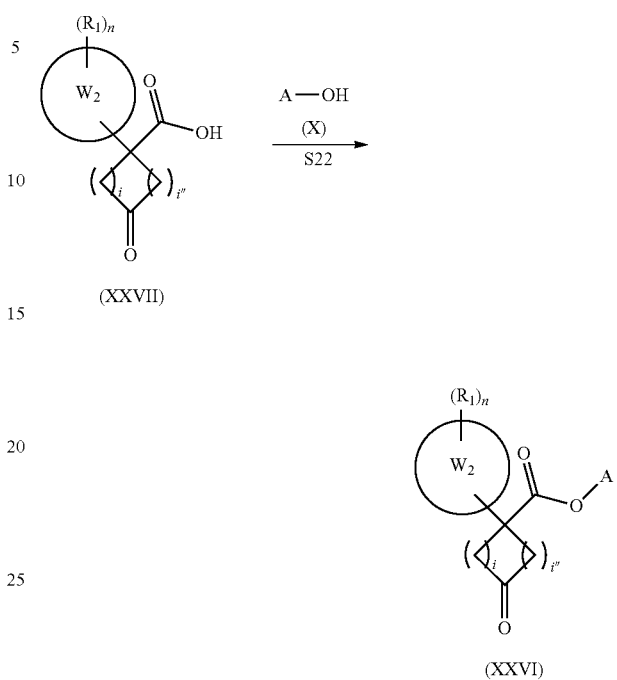

Typical reaction conditions comprise reacting a compound of formula (XXVII) with a compound of formula (X) in a suitable solvent, such as THF in the presence of a suitable coupling agent, such as DCC/HOBt or EDC/DMAP or HATU, at an appropriate temperature, such as room (or ambient) temperature or 40° C.

Compounds of formula (XXV) may be prepared according to Scheme 23/(S23) below by reaction of a compound of formula (XXVIII) as below reported.

Scheme 23 (S23):

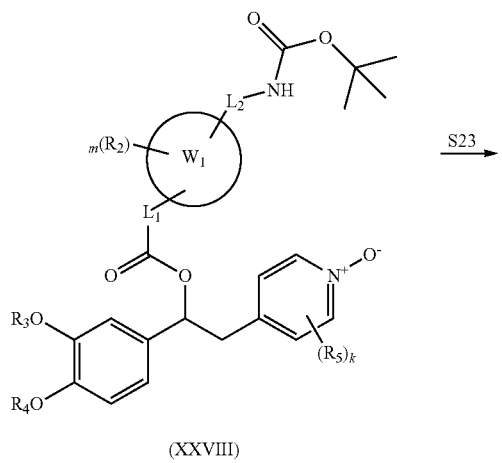

(XXVIII)

-continued

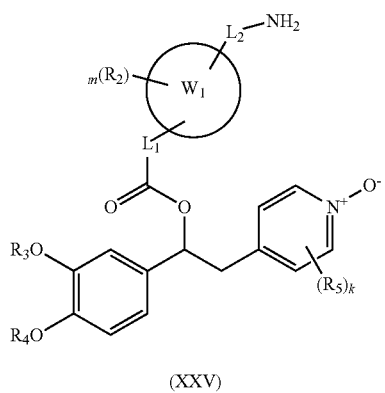

(XXV)

Typical reaction conditions comprise reacting a compound of formula (XXVIII) with an acid such as HCl or TFA in a suitable solvent, such as dioxane or DCM at an appropriate temperature, such as room (or ambient) temperature or 0° C.

Compounds of formula (XXVIII) may be prepared according to Scheme S24 (S24) below by reaction of a compound of formula (XXIX) with a compound of formula (V) as below reported.

Scheme 24 (S24):

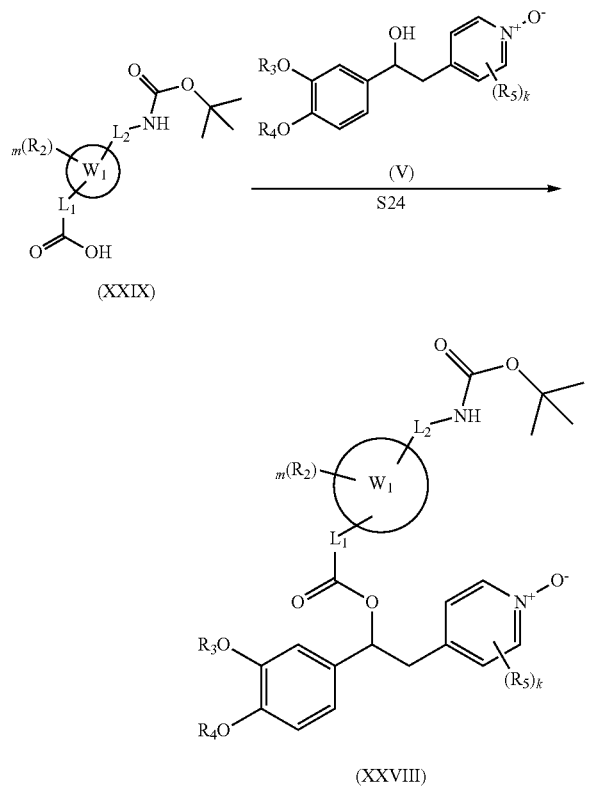

Compounds of formula (XXIX) may be prepared according to Scheme 25/(S25) below by reaction of a compound of formula (XXX) as below reported.

Scheme 25 (S25):

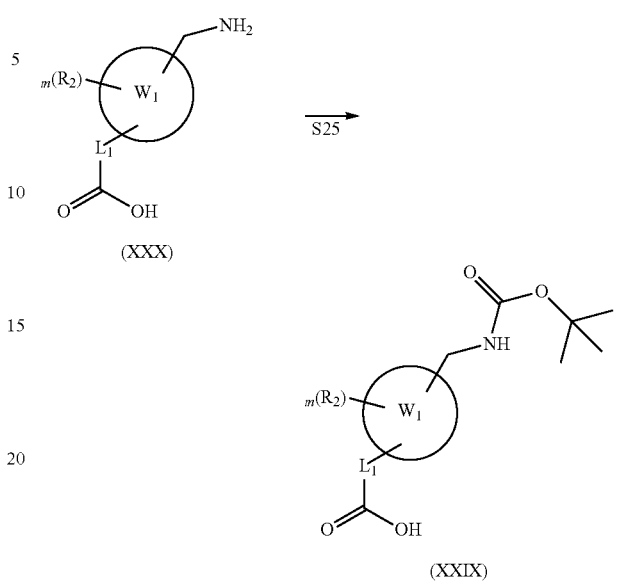

Typical reaction conditions comprise reacting a compound of formula (XXX) with di-tert butyl dicarbonate in a suitable solvent, such as dioxane and water in the presence of sodium hydroxide or $NaHCO_3$ at an appropriate temperature, such as room (or ambient) temperature or 0° C.

The processes described are particularly advantageous as they are susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form.

In particular, functional groups which may be present in the intermediate compounds and reactants depicted in Scheme A or Scheme B and which could generate unwanted side reactions and by-products, need to be properly protected before the relevant reaction takes place. Likewise, subsequent deprotection of those same protected groups may follow upon completion of the said reactions.

According to the invention, unless otherwise indicated, the term "protecting group" designates a protective group adapted to preserve the function of the group it is bound to. Typically, protective groups are used to preserve amino, hydroxy, or carboxyl functions. Appropriate protecting groups may thus include, for example, benzyl, benzyloxycarbonyl, t-butoxycarbonyl, alkyl or benzyl esters or the like, which are well known to those skilled in the art [see, for a general reference, T. W. Green; Protective Groups in Organic Synthesis (Wiley, N.Y. 1999), which is incorporated herein by reference in its entirety].

Likewise, selective protection and deprotection of any of the said groups, for instance including carbonyl, hydroxy or amino groups, may be accomplished according to very well-known methods commonly employed in organic synthetic chemistry.

Optional salification of the compounds of formula (I) may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

The present invention also provides pharmaceutical compositions of compounds of the invention in admixture with one or more pharmaceutically acceptable carriers, for example, those described in Remington's Pharmaceutical Sciences Handbook, XVII Ed., Mack Pub., N.Y., U.S.A., which is incorporated herein by reference in its entirety.

Administration of the compounds of the invention or may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges, and bulk powders. The compounds of the invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants, and the like. Time release capsules, tablets and gels are also advantageous in administering the compounds of the present invention.

Various liquid oral dosage forms may also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, such suitable carriers as are known in the art.

For topical administration the pharmaceutical composition may be in the form of creams, ointments, liniments, lotions, emulsions, suspensions, gels, solutions, pastes, powders, sprays, and drops suitable for administration to the skin, eye, ear, or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metered aerosols, or propellant-free inhalable formulations and may be administered through a suitable inhalation device which may be respectively selected from dry powder inhaler, pressurized metered dosed inhaler, or a nebulizer.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic, or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs), and mucus regulators.

The present invention also provides combinations of a compound of the invention, with a β2-agonist selected from the group consisting of carmoterol, vilanterol (GSK-642444), indacaterol, milveterol, arformoterol, formoterol, salbutamol, levalbuterol, terbutaline, AZD-3199, olodaterol (BI-1744-CL), abediterol (LAS-100977), bambuterol, isoproterenol, procaterol, clenbuterol, reproterol, fenoterol, and ASF-1020 and salts thereof.

The present invention also provides combinations of a compound of the invention, with a corticosteroid selected from the group consisting of fluticasone propionate, fluticasone furoate, mometasone furoate, beclometasone dipropionate, ciclesonide, budesonide, GSK 685698, and GSK 870086.

The present invention also provides combinations of a compound of the invention, with an antimuscarinic agent selected from the group consisting of aclidinium, tiotropium, ipratropium, trospium, glycopyrronium, and oxitropium salts.

The present invention also provides combinations of a compound of the invention, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414, and RPL-554.

The present invention also provides combinations of a compound of the invention, with a P38 MAP kinase inhibitor selected from the group consisting of semapimod, talmapimod, pirfenidone, PH-797804, GSK-725, minokine, and losmapimod and salts thereof.

In a preferred embodiment, the present invention provides combinations of a compound of the invention with an IKK2 inhibitor.

The present invention also provides combinations of a compound of the invention with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C, and prolastin inhaled.

The present invention also provides combinations of a compound of the invention with a leukotriene modulator selected from the group consisting of montelukast, zafirlukast, and pranlukast.

The present invention also provides combinations of a compound of the invention with a NSAID selected from the group consisting of ibuprofen and ketoprofen.

The present invention also provides combinations of a compound of the invention with a mucus regulator selected from the group consisting of INS-37217, diquafosol, sibenadet, CS-003, talnetant, DNK-333, MSI-1956, and gefitinib.

The dosages of the compounds of the invention depend upon a variety of factors, including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the invention may be administered for example, at a dosage of 0.001 to 1000 mg/day, preferably 0.1 to 500 mg/day.

When they are administered by inhalation route, the dosage of the compounds of the invention is advantageously 0.01 to 20 mg/day, preferably 0.1 to 10 mg/day.

Preferably, the compounds of the invention alone or combined with other active ingredients may be administered for the prevention and/or treatment of any obstructive respiratory disease such as asthma, chronic bronchitis, and chronic obstructive pulmonary disease (COPD).

The compounds of the invention may be administered for the prevention and/or treatment of any disease wherein PDE4 inhibition or M3 antagonism is required. Said diseases include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia areata, hypertrophic scars, discoid lupus erythematosus, systemic lupus erythematosus, follicular and wide-area pyodermias, endogenous and exogenous acne, acne rosacea, Behçet's disease, anaphylactoid purpura nephritis, inflammatory bowel disease, leukemia, multiple sclerosis, gastrointestinal diseases, autoimmune diseases, and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Abbreviations

Boc=terbutoxycarbonyl;
Cbz=benzyloxycarbonyl;
AcOH=acetic acid;
DCC=N,N'-dicyclohexylcarbodiimide;
HOBt=hydroxybenzotriazole;
HATU=(dimethylamino)-N,N-dimethyl(3H-[1,2,3]triazolo[4,5-b]pyridin-3-yloxy) methaniminium hexafluorophosphate;
EDC=1-ethyl-3-(3-dimethylaminopropyl) carbodiimide hydrochloride;
DMAP=4-dimethylaminopyridine;
DMF=dimethylformamide;
DMSO=dimethyl sulfoxide;
EtOAc=ethyl acetate;
RT=room temperature;
THF=tetrahydrofuran;
DCM=dichloromethane;
MeOH=methyl alcohol;
EtOH=ethyl alcohol;
LHMDS=lithium bis(trimethylsilyl)amide;
LC-MS=liquid chromatography/mass spectrometry;
NMR=nuclear magnetic resonance;
HPLC=high pressure liquid chromatography;
SFC=supercritical fluid chromatography General Experimental Details Analytical Methods
Liquid Chromatography—Mass Spectrometry
Method 1

LC-MS was performed on a Waters 2795 Alliance HT HPLC with Waters 2996 Diode Array Detector coupled to a Micromass ZQ, single quadrapole mass spectrometer using a Phenomenex Luna C18 (2) column (5 µm, 100×4.6 mm plus guard cartridge) with a linear gradient of 5-95% acetonitrile/water (with 0.1% formic acid in each mobile phase) within 3.5 minutes and held at 95% for 2.0 minutes.
Method 2

LC-MS was performed on a Waters 2795 Alliance HT HPLC with Waters 2996 Diode Array Detector coupled to a Micromass ZQ, single quadrapole mass spectrometer using a Waters Xterra MS C18 column (5 µm, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.
Method 3

UPLC-MS was performed on a Waters Acquity I-Class with Waters Diode Array Detector coupled to a Waters SQD2 single quadrapole mass spectrometer using an Waters HSS C18 column (1.8 µm, 100×2.1 mm) being initially held at 5% acetonitrile/water (with 0.1% formic acid in each mobile phase) for 1.2 minutes, followed by a linear gradient of 5-100% within 3.5 minutes and then held at 100% for 1.5 minutes (F=0.5 mL/min).
Method 10

UPLC-MS was performed on a Waters Acquity I-Class with Waters Diode Array Detector coupled to a Waters SQD2 single quadrapole mass spectrometer using an BEH Shield RP18 column (1.7 µm, 100×2.1 mm) being initially held at 5% acetonitrile/water (with 10 mM ammonium bicarbonate in each mobile phase) for 1.2 minutes, followed by a linear gradient of 5-100% within 3.5 minutes and then held at 100% for 1.5 minutes (F=0.5 mL/min).

Chiral Separation Protocol

The diastereomeric separation of compounds was achieved either by chiral High Performance Liquid Chromatography (HPLC) using a Gilson Trilution preparative HPLC system (322 pump, 155 UVNIS, GX281 liquid handler and fraction collector) or by Supercritical Fluid Chromatography (SFC) using a Waters Thar Prep100 preparative SFC system (P200 $CO_2$ pump, 2545 modifier pump, 2998 UVNIS detector, 2767 liquid handler with Stacked Injection Module). The Waters 2767 liquid handler acted as both auto-sampler and fraction collector.

The column used for the preparative purification of the compounds was a Diacel Chiralpak IA/IB/IC, a Phenomenex Lux Cellulose-4, an YMC Amylose-C or an YMC Cellulose-C at 5 μm 250×20-21.2 mm ID.

Appropriate isocratic methods were selected based on methanol, ethanol or isopropanol solvent systems under un-modified or basic conditions.

The standard SFC method used was modifier, $CO_2$, 100 mL/min, 120 Bar backpressure, 40° C. column temperature. The standard HPLC method used was modifier, heptane, 5 mL/min and room temperature.

The modifier used under basic conditions was diethylamine (0.1% VN). The modifier used under acidic conditions was either formic acid (0.1% V/V) or trifluoroacetic acid (0.1% V/V).

The SFC purification was controlled by Waters Fractionlynx software through monitoring at 210-400 nm and triggered at a threshold collection value, typically 260 nm. Collected fractions were analysed by SFC (Waters/Thar SFC systems with Waters SQD). The fractions that contained the desired product were concentrated by vacuum centrifugation.

HPLC purification was controlled by Gilson Trilution software monitoring two wavelengths and triggered at a threshold collection value, typically 260 nm. Collected fractions were analysed by HPLC (Agilent 1200 series HPLC system). The fractions that contained the desired product were concentrated by vacuum centrifugation.

Supercritical Fluid Chromatography—Mass Spectrometry Analytical Conditions

Method 4

SFC-MS was performed on a Waters/Thar SFC systems with Waters SQD using a YMC Amylose-C column with a 30% iso-propyl alcohol/$CO_2$ (with 0.1% diethylamine) isocratic run at 5 mL/min, 120 Bar backpressure, 40° C. column temperature.

Method 5

SFC-MS was performed on a Waters/Thar SFC systems with Waters SQD using a YMC Amylose-C column with a 35% iso-propyl alcohol/$CO_2$ (with 0.1% diethylamine) isocratic run at 5 mL/min, 120 Bar backpressure, 40° C. column temperature.

Method 6

SFC-MS was performed on a Waters/Thar SFC systems with Waters SQD using a YMC Amylose-C column with a 40% ethyl alcohol/$CO_2$ (with 0.1% diethylamine) isocratic run at 5 mL/min, 120 Bar backpressure, 40° C. column temperature.

Method 7

SFC-MS was performed on a Waters/Thar SFC systems with Waters SQD using a YMC Cellulose-C column with a 40% ethyl alcohol/$CO_2$ (with 0.1% diethylamine) isocratic run at 5 mL/min, 120 Bar backpressure, 40° C. column temperature.

Method 8

SFC-MS was performed on a Waters/Thar SFC systems with Waters SQD using a YMC Cellulose-C column with a 55% ethyl alcohol/$CO_2$ (with 0.1% diethylamine) isocratic run at 5 mL/min, 120 Bar backpressure, 40° C. column temperature.

Method 11

SFC-MS was performed on a Waters/Thar SFC systems with Waters SQD using a YMC Amylose-C column with a 45% ethyl alcohol/$CO_2$ (with 0.1% diethylamine) isocratic run at 5 mL/min, 120 bar backpressure, 40° C. column temperature.

Chiral HPLC—Analytical Conditions

Method 9

Chiral HPLC was performed on an Agilent 1200 series HPLC system using a Chiralpak IB column with 50% ethyl alcohol/heptane (with 0.1% diethylamine) at 1 mL/min.

NMR $^1$H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Preparative Reverse-Phase HPLC Conditions

Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector.

The columns used for the preparative purification of the compounds were a Waters Sunfire OBD Phenomenex Luna Phenyl Hexyl or Waters Xbridge Phenyl at 10 μm 19×150 mm or Waters CSH Phenyl Hexyl, 19×150, 5 μm column.

Appropriate focused gradients were selected based on acetonitrile and methanol solvent systems under either acidic or basic conditions.

The modifiers used under acidic/basic conditions were formic acid or trifluoroacetic acid (0.1% V/V) and ammonium bicarbonate (10 mM) respectively.

The purification was controlled by Waters Fractionlynx software through monitoring at 210-400 nm, and triggered a threshold collection value at 260 nm and, when using the Fractionlynx, the presence of target molecular ion as observed under API conditions. Collected fractions were analysed by LCMS (Waters Acquity systems with Waters SQD).

Compound Preparation

Where the preparation of starting materials is not described, these are commercially available, known in the literature, or readily obtainable by those skilled in the art using standard procedures. Where it is stated that compounds were prepared "analogously" or "similarly" to earlier examples or intermediates, it will be appreciated by the skilled person that the reaction time, number of equivalents of reagents and temperature can be modified for each specific reaction and that it may be necessary or desirable to employ different work-up or purification techniques.

Many of the compounds described in the following Examples have been prepared from stereochemically pure starting materials, for example, 95% enantiomeric excess (ee).

The stereochemistry of the compounds in the examples, where indicated, has been assigned on the assumption that absolute configuration at resolved stereogenic centers of staring materials is maintained throughout any subsequent reaction conditions.

Compounds isolated as single diastereoisomers whose absolute configuration at one stereogenic center was not determined, are herebelow referred to as Single Diastereoisomers without mention in their chemical name of absolute configuration for the unknown stereogenic centre. An asterisk "*" was introduced in the chemical structures on a stereogenic center that was isolated as single diastereoisomer or enantiomer but without assignment of the absolute configuration.

Intermediate 1. [(1S)-2-(3,5-Dichloro-1-oxido-pyridin-1-ium-4-yl)-1-(3,4-dimethoxyphenyl)ethyl] 5-formyl-thiophene-2-carboxylate

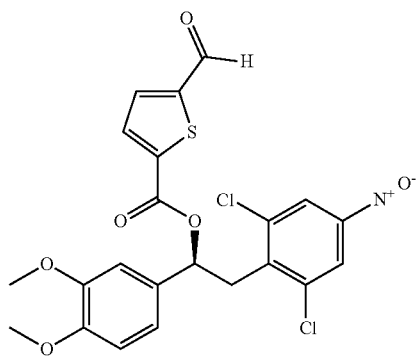

To a stirred solution of 5-formyl-2-thiophenecarboxylic acid (400 mg, 2.56 mmol) in dichloromethane (20 mL) was added (1S)-2-(3,5-dichloro-1-oxido-pyridin-1-ium-4-yl)-1-(3,4-dimethoxyphenyl)ethanol (compound I-1/A described in co-pending International Patent Application No. PCT/EP2013/075520, which is incorporated herein by reference in its entirety) (881 mg, 2.56 mmol) followed by 4-(dimethylamino)-pyridine (156 mg, 1.28 mmol) and N-(3-dimethylaminopropyl)-N'-ethylcarbodiimide hydrochloride (983 mg, 5.12 mmol). The resulting mixture was stirred at room temperature for 18 hours. The reaction was partitioned between dichloromethane and saturated aqueous sodium bicarbonate solution. The organic layer was washed with brine, passed through a hydrophobic fit and the solvent was removed in vacuo. The crude material was purified by silica gel column chromatography, eluting with 0-100% EtOAc in DCM, to afford the title compound (488 mg, 39%) as yellow oil.

$^1$H NMR (400 MHz, CDCl3): δ 9.97 (s, 1H), 8.15 (s, 2H), 7.81 (d, J=3.6 Hz, 1H), 7.72 (d, J=3.6 Hz, 1H), 7.03-6.99 (m, 2H), 6.87 (d, J=8.7 Hz, 1H), 6.26 (dd, J=4.4, 10.0 Hz, 1H), 3.91 (s, 3H), 3.88 (s, 3H), 3.72 (dd, J=10.0, 14.0 Hz, 1H), 3.33 (dd, J=4.4, 14.0 Hz, 1H). LCMS (Method 2): [MH+]= 482 at 3.38 min.

The following intermediates were synthesized via a similar method to Intermediate 1.

| Structure | Intermediate number | Analytical Data |
|---|---|---|
| 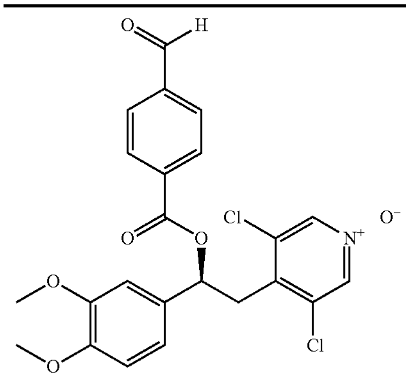 | Intermediate 2 | $^1$H NMR (400 MHz, CDCl$_3$): δ 10.09 (s, 1 H), 8.45 (s, 2 H), 8.19 (d, J = 8.1 Hz, 2 H), 7.94 (d, J = 8.1 Hz, 2 H), 7.08 (dd, J = 8.2, 2.1 Hz, 1 H), 6.99 (d, J = 2.0 Hz, 1 H), 6.87 (d, J = 8.3 Hz, 1 H), 6.36 (dd, J = 10.0, 4.3 Hz, 1 H), 3.90 (s, 3 H), 3.88 (s, 3 H), 3.83 (dd, J = 13.7, 10.0 Hz, 1 H), 3.43 (dd, J = 13.7, 4.4 Hz, 1 H). LCMS (Method 1): [MH+] = 460 at 4.45 min. |
| 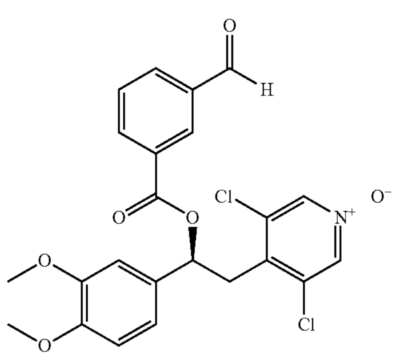 | Intermediate 3 | $^1$H NMR (400 MHz, CDCl$_3$): δ 10.08 (s, 1 H), 8.54 (t, J = 1.7 Hz, 1 H), 8.27 (dt, J = 7.8, 1.5 Hz, 1 H), 8.14 (s, 2 H), 8.09 (dt, J = 7.7, 1.5 Hz, 1 H), 7.63 (t, J = 7.7 Hz, 1 H), 7.05 (dd, J = 8.2, 2.1 Hz, 1 H), 7.00 (d, J = 2.1 Hz, 1 H), 6.87 (d, J = 8.3 Hz, 1 H), 6.33 (dd, J = 9.7, 4.6 Hz, 1 H), 3.92 (s, 3 H), 3.88 (s, 3 H), 3.76 (dd, J = 14.0, 9.8 Hz, 1 H), 3.39 (dd, J = 14.0, 4.6 Hz, 1 H). LCMS (Method 1): [MH+] = 476 at 3.55 min. |

Intermediate 4. [(3R)-quinuclidin-3-yl]-3-(tert-butoxycarbonylamino)-2-phenyl-propanoate

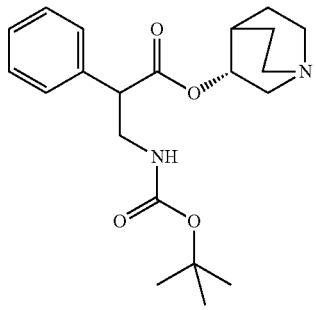 [SMILES: CC(C)(C)OC(=O)NCC(C(=O)O[C@H]1CN2CCC1CC2)c1ccccc1]

To a solution of 3-(tert-butoxycarbonylamino)-2-phenyl-propanoic acid (795 mg, 3.0 mmol) in THF (50 mL) was successively added N,N'-dicyclohexylcarbodiimide (745 mg, 3.6 mmol), 1-hydroxybenzotriazole hydrate (490 mg, 3.6 mmol) and (R)-quinuclidin-3-ol (460 mg, 3.6 mmol). The resulting mixture was stirred at room temperature for 18 hours. After this time, the reaction mixture was filtered through a pad of Celite® and the solvent was removed in vacuo. The residue was partitioned between EtOAc (100 mL) and saturated aqueous $Na_2CO_3$ (2×50 mL), and the resulting aqueous fractions were re-extracted with EtOAc (2×50 mL). The combined organic fractions were washed with brine (30 mL), dried ($Na_2SO_4$), filtered and the solvent removed in vacuo to give a white foam (950 mg, 85% yield), which was used in the next step without further purification.

LCMS (Method 2): [MH+]=375 at 2.99 min.

The following intermediates were synthesized via a similar method.

| Structure | Intermediate | Precursor | Analytical Data |
|---|---|---|---|
| 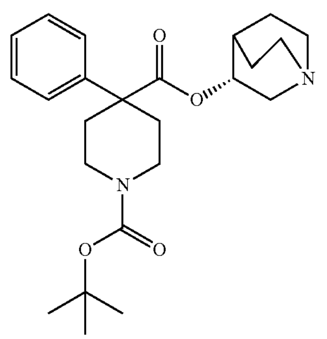 [SMILES: CC(C)(C)OC(=O)N1CCC(C(=O)O[C@H]2CN3CCC2CC3)(c2ccccc2)CC1] | Intermediate 5 | 1-tert-butoxycarbonyl-4-phenyl-piperidine-4-carboxylic acid | LCMS (Method 1): [MH+] = 415 at 5.49 min |
| 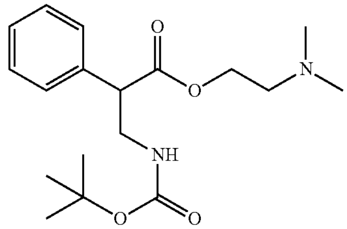 [SMILES: CN(C)CCOC(=O)C(CNC(=O)OC(C)(C)C)c1ccccc1] | Intermediate 6 | 3-((tert-butoxycarbonyl)amino)-2-phenylpropanoic acid | LCMS ([Method 6]): [MH+] = 337 at 3.13 min |
| 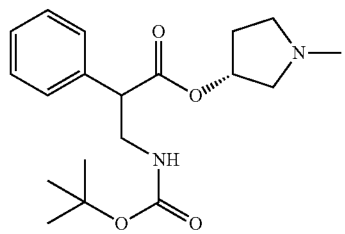 [SMILES: CN1CC[C@@H](OC(=O)C(CNC(=O)OC(C)(C)C)c2ccccc2)C1] | Intermediate 7 | 3-((tert-butoxycarbonyl)amino)-2-phenylpropanoic acid | LCMS ([Method 6]): [MH+] = 349 at 3.55 min |
| 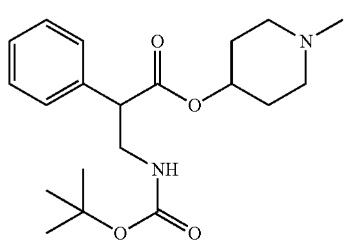 [SMILES: CN1CCC(OC(=O)C(CNC(=O)OC(C)(C)C)c2ccccc2)CC1] | Intermediate 8 | 3-((tert-butoxycarbonyl)amino)-2-phenylpropanoic acid | LCMS ([Method 6]): [MH+] = 363 at 3.50 min |

Intermediate 9. [(3R)-quinuclidin-3-yl]-3-amino-2-phenyl-propanoate bis hydrochloride

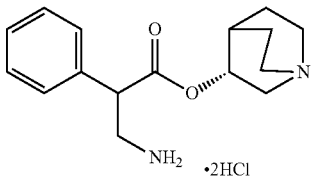 [SMILES: NCC(C(=O)O[C@H]1CN2CCC1CC2)c1ccccc1]

To a solution of [(3R)-quinuclidin-3-yl] 3-(tert-butoxycarbonylamino)-2-phenyl-propanoate (950 mg, 2.54 mmol) in 1,4-dioxane (20 mL) was added 4 N HCl in dioxane (3.2 mL, 12.7 mmol) and the mixture was stirred at room temperature for 18 hours. The solvent was removed by evaporation under reduced pressure, co-evaporated with Et$_2$O to give the title compound as a yellow solid (875 mg, quantitative yield).

LCMS (Method 2): [MH+]=275 at 2.45 min.

The following intermediate was synthesized via a similar method:

| Structure | Intermediate | Precursor | Analytical Data |
|---|---|---|---|
| 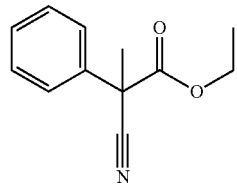 | Intermediate 10 | Intermediate 5 | $^1$H NMR (400 MHz, DMSO): δ 7.47-7.32 (m, 5 H), 5.05-5.00 (m, 1 H), 3.24-2.91 (m, 11 H), 2.73-2.59 (m, 2 H), 2.29-2.08 (m, 3 H), 1.84-1.70 (m, 2 H), 1.60-1.44 (m, 2 H). |

Intermediate 11. (1-methyl-4-piperidyl)-3-(tert-butoxycarbonylamino)-2-methyl-2-phenyl-propanoate

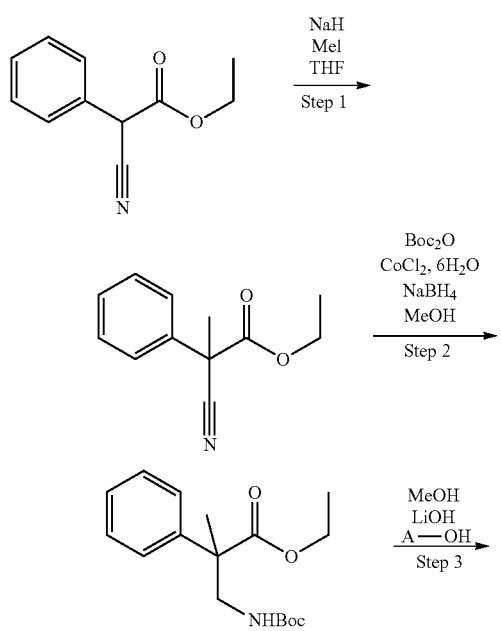

Step 1: Preparation of ethyl 2-cyano-2-phenylpropanoate

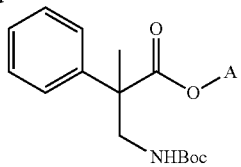

To a slurry of sodium hydride (60% dispersion in mineral oil, 811 mg, 20.2 mmol) in dry THF (170 mL) at 0° C. was added ethyl 2-cyano-2-phenylacetate (3.2 g, 16.9 mmol). The resulting mixture was stirred for one hour at 0° C. before adding methyl iodide (2.87 mL, 30.3 mmol) dropwise and slowly warming the mixture to room temperature over 16 hours. The mixture was then quenched with saturated aqueous NH$_4$Cl (100 mL) and EtOAc (200 mL). The layers were separated and the aqueous phase was back-extracted with EtOAc (3×50 mL). The combined organic phases were dried (MgSO$_4$), filtered and the solvent was removed in vacuo. The residue was purified by silica gel column chromatography, eluting with 10% EtOAc in isohexane to give the title compound as a colourless oil (2.2 g, 64%).

$^1$H NMR (400 MHz, CDCl$_3$): δ 7.55-7.51 (m, 2H), 7.44-7.36 (m, 3H), 4.26-4.22 (m, 2H), 1.96 (s, 3H), 1.25 (t, J=7.2 Hz, 3H).

Step 2: Preparation of ethyl 3-((tert-butoxycarbonyl)amino)-2-methyl-2-phenylpropanoate

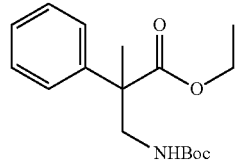 [SMILES: CCOC(=O)C(C)(CNC(=O)OC(C)(C)C)c1ccccc1]

To a solution of ethyl 2-cyano-2-phenylpropanoate (2.2 g, 10.8 mmol) in MeOH (10 mL), was added Boc$_2$O (4.71 g, 21.6 mmol) and CoCl$_2$.6H$_2$O (3.1 g, 13 mmol). The resulting pink mixture was cooled to 0° C. and NaBH$_4$ (1.03 g, 27 mmol) was added portionwise over 10 minutes. After effervescence had stopped, additional NaBH$_4$ (500 mg, 13.1 mmol) was added to the blue slurry and the mixture was stirred at 0° C. for a further 10 minutes and at room temperature for 1.5 hours. Water (50 mL) and EtOAc (200 mL) were cautiously added at 0° C. and the mixture was stirred at room temperature for 10 minutes. The pink slurry was filtered through a pad of Celite® and the cake washed with EtOAc (100 mL). The filtrate was transferred to a separatory funnel and the layers separated. The aqueous layer was back-extracted with EtOAc (3×50 mL). The combined organic phases were dried (MgSO$_4$), filtered and the solvent was removed in vacuo. The residue was purified was purified by silica gel column chromatography, eluting with 5% of a 7N methanolic ammonia solution in ethyl acetate to give the title compound as a white solid (200 mg, 17% over two steps).

$^1$H NMR (400 MHz, CDCl$_3$): δ 7.37-7.22 (m, 5H), 6.01-5.55 (m, 1H), 5.01-4.92 (m, 1H), 4.91-4.81 (m, 1H), 3.73-3.59 (m, 1H), 2.41-2.25 (m, 4H), 2.21 (s, 3H), 1.97-1.79 (m, 2H), 1.72-1.63 (m, 2H), 1.61 (s, 3H), 1.39 (s, 9H).

The following intermediates were synthesized via the same method:

| Structure | Intermediate number | Precursor | Analytical Data |
|---|---|---|---|
| 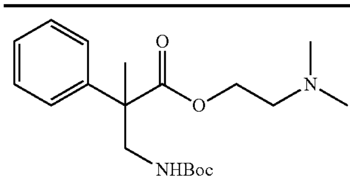 | Intermediate 12 | Ethyl 3-((tert-butoxycarbonyl)amino)-2-methyl-2-phenylpropanoate | LCMS ([Method 6]): [MH+] = 351 at 3.93 min |
| | Intermediate 13 | Ethyl 3-((tert-butoxycarbonyl)amino)-2-methyl-2-phenylpropanoate | LCMS ([Method 6]): [MH+] = 389 at 2.91 min | by silica gel column chromatography, eluting with 10% EtOAc in isohexane to give the title compound as a thick oil (3.3 g, quantitative yield).

$^1$H NMR (400 MHz, CDCl$_3$): δ 7.36-7.30 (m, 2H), 7.27-7.22 (m, 3H), 5.02-4.91 (m, 1H), 4.22-4.14 (m, 2H), 3.60 (dd, J=5.9, 13.8 Hz, 1H), 3.55-3.45 (m, 1H), 1.61 (s, 3H), 1.39 (s, 9H), 1.21 (t, J=7.2 Hz, 3H). LCMS (Method 2): [MH+]=308 at 3.62 min.

Step 3: Preparation of (1-methyl-4-piperidyl) 3-(tert-butoxycarbonylamino)-2-methyl-2-phenyl-propanoate

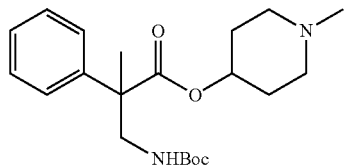 [SMILES: CN1CCC(OC(=O)C(C)(CNC(=O)OC(C)(C)C)c2ccccc2)CC1]

To a solution of ethyl 3-((tert-butoxycarbonyl)amino)-2-methyl-2-phenylpropanoate (1.9 g, 6.2 mmol) in MeOH (50 mL), was added LiOH (1 N in water, 50 mL, 50 mmol) at room temperature. The resulting mixture was refluxed for 18 hours, cooled to room temperature and acidified with 2 N HCl solution to pH-2. The aqueous layer was back-extracted with EtOAc (3×100 mL). The combined organic phases were dried over MgSO$_4$, filtered and the solvent was removed in vacuo. Half of the white solids residue (650 mg, 2.33 mmol) was dissolved in dry THF (10 mL). 3-Hydroxy-N-methyl-piperidine (322 mg, 2.80 mmol), 1-hydroxyben-zotriazole (377 mg, 2.80 mmol) and N,N'-dicyclohexylcar-bodiimide (577 mg, 2.80 mmol) were added and the reaction mixture stirred at room temperature for 2 days. After this time the reaction mixture was filtered through a pad of Celite® which was then washed with EtOAc (100 mL) and the filtrate was washed with saturated aqueous Na$_2$CO$_3$ (2×50 mL). The organic phase was dried over MgSO$_4$, filtered and the solvent was removed in vacuo. The residue Intermediate 14. [(1δS)-2-(3,5-dichloro-1-oxido-pyridin-1-ium-4-yl)-1-(3,4-dimethoxyphenyl)-ethyl] 4-(1,3-dioxolan-2-ylmethyl)benzoate

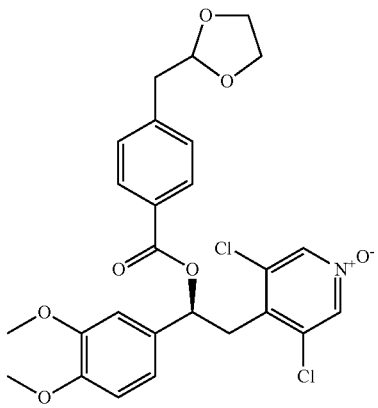

To a solution of 4-((1,3-dioxolan-2-yl)methyl)benzoic acid (362 mg, 1.05 mmol) in DCM (9 mL) was added (1S)-2-(3,5-dichloro-1-oxido-pyridin-1-ium-4-yl)-1-(3,4-dimethoxyphenyl)ethanol (200 mg, 0.96 mmol) followed by DMAP (58 mg, 0.48 mmol) and EDC.HCl (396 mg, 1.9 mmol). The mixture was stirred at room temperature for 18 hours. H$_2$O (20 mL) and DCM (20 mL) were then added and the organic phase was passed through a hydrophobic fit. The solvent was removed in vacuo and the crude material was purified by silica gel column chromatography, eluting with 30-100% EtOAc in DCM, to give the title compound as an off-white solid (497 mg, 97%).

$^1$H NMR (400 MHz, CDCl$_3$): δ 8.13 (s, 2H), 7.96 (d, J=8.1 Hz, 2H), 7.34 (d, J=8.1 Hz, 2H), 7.02-6.97 (m, 2H), 6.85 (d, J=8.2 Hz, 1H), 6.29 (dd, J=9.7, 4.6 Hz, 1H), 5.08 (t, J=4.6 Hz, 1H), 3.95-3.80 (m, 10H), 3.76-3.66 (m, 1H), 3.34 (dd, J=14.0, 4.6 Hz, 1H), 3.02 (d, J=4.6 Hz, 2H). LCMS (Method 1): [MH+]=534 at 3.70 min.

The following intermediate was synthesized via a similar method to Intermediate 14.

| Structure | Intermediate number | Analytical Data |
|---|---|---|
| 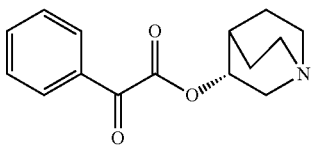 [SMILES: O=C(O[C@H]1CN2CCC1CC2)C(=O)c1ccccc1] | Intermediate 15 | $^1$H NMR (400 MHz, CDCl$_3$): δ 8.13 (s, 2 H), 7.94 (s, 1 H), 7.91 (d, J = 7.8 Hz, 1 H), 7.48 (d, J = 7.7 Hz, 1 H), 7.37 (t, J = 7.7 Hz, 1 H), 7.04-6.99 (m, 2 H), 6.86 (d, J = 8.2 Hz, 1 H), 6.29 (dd, J = 9.8, 4.5 Hz, 1 H), 5.07 (t, J = 4.6 Hz, 1 H), 3.94-3.81 (m, 4 H), 3.91 (s, 3 H), 3.87 (s, 3 H), 3.72 (dd, J = 14.0, 9.8 Hz, 1 H), 3.35 (dd, J = 14.0, 4.6 Hz, 1 H), 3.01 (d, J = 4.6 Hz, 2 H). LCMS (Method 2): [MH+] = 534 at 3.58 min. |

Intermediate 16.
[(3R)-quinuclidin-3-yl]-2-oxo-2-phenyl-acetate

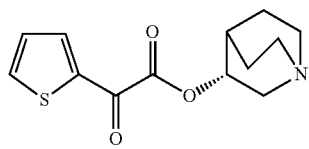 [SMILES: O=C(O[C@H]1CN2CCC1CC2)C(=O)c1cccs1]

To a mixture of 2-oxo-2-phenyl-acetic acid (4.01 g, 26.7 mmol) and DMF (2 drops) in CHCl$_3$ (60 mL) at 0° C. was added dropwise oxalyl chloride (3.62 mL, 42.8 mmol) over a period of 10 minutes. The mixture was stirred at 0° C. for a further 30 minutes, then allowed to warm to room temperature and stirred for 2 hours. The solvent was removed in vacuo, co-evaporated with CHCl$_3$ to give a yellow mobile oil which was re-dissolved in CHCl$_3$ (15 mL) and added dropwise to a solution of (3R)-quinuclidin-3-ol (3.73 g, 29.4 mmol) in CHCl$_3$ (50 mL) at 0° C. under N$_2$. The mixture was stirred at 0° C. for a further 30 minutes, then allowed to warm to room temperature and stirred overnight. The solvent was removed in vacuo and the residue was suspended in toluene (100 mL) and extracted with saturated NaHCO$_3$ solution (2×50 mL). The combined acidic aqueous phase was basified with solid K$_2$CO$_3$ and extracted with CHCl$_3$ (3×75 mL), the combined organic phases were filtered through a phase separator fit and the solvent removed in vacuo to give the title compound as a yellow oil, which solidified on standing (6.30 g, 91%). LCMS (Method 2): [MH+]=260 at 2.71 min.

Intermediate 17. (3R)-Quinuclidin-3-yl-2-oxo-2-(2-thienyl)acetate

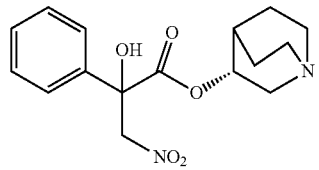 [SMILES: O=C(O[C@H]1CN2CCC1CC2)C(O)(C[N+](=O)[O-])c1ccccc1]

To a solution of ethyl-2-oxo-2-(2-thienyl)acetate (3 mL, 20.3 mmol) in EtOH (30 mL) and H$_2$O (30 mL) was added solid NaOH (1.22 g, 30.6 mmol). The resulting mixture was stirred at room temperature for 18 h then 2 N aqueous HCl was added at 0° C. until ~pH 2-3. The aqueous phase was extracted with EtOAc (3×50 mL) and the organic phases were combined, dried over MgSO$_4$, filtered and concentrated in vacuo. The residue was redissolved in dry DCM (46 mL). The resulting solution was cooled to 0° C. and oxalyl chloride (2.1 mL, 24.4 mmol) was added followed by a couple of drops of DMF. The reaction mixture was stirred for 20 minutes at 0° C. and then at room temperature for 4 hours. The reaction solvent was removed in vacuo and the residue azeotroped with CHCl$_3$. The residue was redissolved in CHCl$_3$ (50 mL) and added to a solution of (R)-quinuclidin-3-ol (5.2 g, 40.6 mmol) in CHCl$_3$ (50 mL) at 0° C. The resulting solution was stirred at 0° C. for 30 minutes and then at room temperature for 18 hours. The reaction solution was diluted with DCM (100 mL) and H$_2$O (20 mL). The organic phase was passed through a hydrophobic fit and concentrated in vacuo to give the title compound as a brown oil (4.97 g, 92%). LCMS (Method 1): [MH+]=266 at 2.15 min.

Intermediate 18. [(3R)-quinuclidin-3-yl]-2-hydroxy-3-nitro-2-phenyl-propanoate

To a stirred solution of [(3R)-quinuclidin-3-yl]-2-oxo-2-phenyl-acetate (3.20 g, 12.3 mmol) in nitromethane (45 mL) was added dry Et$_3$N (0.34 mL, 2.47 mmol) and the resulting solution was stirred at room temperature for 24 hours. The solvent was removed in vacuo, co-evaporated with EtOAc then CH$_3$CN to give the title compound as a yellow solid (3.68 g, 93%). LCMS (Method 1): [MH+]=321 at 2.61 min.

The following intermediate was synthesized via the same method:

| Structure | Intermediate | Precursor | Analytical Data |
|---|---|---|---|
| 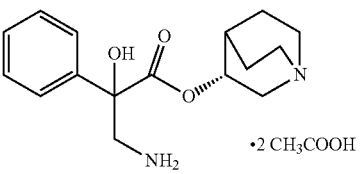 [SMILES: NCC(O)(C(=O)O[C@H]1CN2CCC1CC2)c1ccccc1] | Intermediate 19 | Intermediate 17 | $^1$H NMR (400 MHz, CDCl$_3$): δ 7.35 (dd, J = 1.3, 5.1 Hz, 1 H), 7.18 (dd, J = 1.3, 3.6 Hz, 1 H), 7.04 (dd, J = 3.7, 5.1 Hz, 1 H), 5.08-5.02 (m, 1 H), 3.31-3.23 (m, 1 H), 3.17-2.99 (m, 2 H), 2.77-2.69 (m, 2 H), 2.19-2.09 (m, 1 H), 1.80-1.70 (m, 2 H), 1.65-1.56 (m, 2 H), 1.54-1.44 (m, 1 H). |

Intermediate 20. [(3R)-quinuclidin-3-yl]-3-amino-2-hydroxy-2-phenyl-propanoate, bis acetate To a stirred solution of [(3R)-quinuclidin-3-yl]-2-hydroxy-3-nitro-2-phenyl-propanoate (0.93 g, 2.91 mmol) in glacial acetic acid (40 mL) under N$_2$ was added zinc dust (7.60 g 0.116 mol) portionwise over a period of 45 minutes. After stirring the mixture at room temperature overnight, the mixture was filtered through a pad of Celite®, washed through with AcOH and the solvent removed in vacuo to give the title compound as a yellow gum (2.2 g, quantitative yield). LCMS (Method 2): [MH+]=291 at 2.05 min.

The following intermediate was synthesized via the same method:

Example 1. [(1S)-2-(3,5-dichloro-1-oxido-pyridin-1-ium-4-yl)-1-(3,4-dimethoxyphenyl)ethyl] 5-[[[3-oxo-2-phenyl-3-[(3R)-quinuclidin-3-yl]oxy-propyl]amino]methyl]thiophene-2-carboxylate

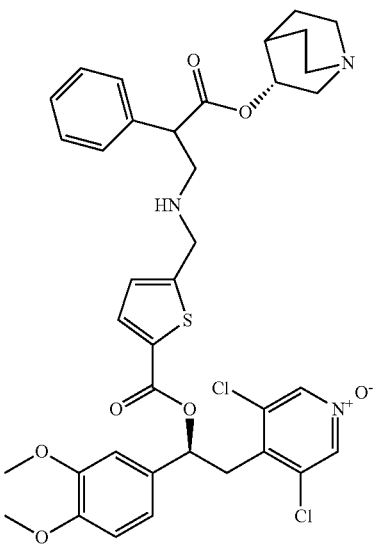

To a suspension of [(3R)-quinuclidin-3-yl] 3-amino-2-phenyl-propanoate bis hydrochloride (Intermediate 9) (380 mg, 1.1 mmol) in EtOH (10 mL) was successively added Et$_3$N (0.31 mL, 2.2 mmol), acetic acid (63 µL, 1.1 mmol), [(1S)-2-(3,5-dichloro-1-oxido-pyridin-1-ium-4-yl)-1-(3,4-dimethoxyphenyl)ethyl] 5-formyl-thiophene-2-carboxylate (intermediate 1) (260 mg, 0.55 mmol) and NaBH$_3$CN (70 mg, 1.1 mmol). The resulting mixture was stirred at room

| Structure | Intermediate | Precursor | Analytical Data |
|---|---|---|---|
| | Intermediate 21 | Intermediate 19 | LCMS (Method 2): [MH+] = 297 at 1.53 min. | temperature for 18 hours. The solvent was removed in vacuo, the residue partitioned between EtOAc (20 mL) and H₂O (20 mL), and the aqueous fraction was back-extracted with EtOAc (2×20 mL). The combined organic fractions were washed with 0.2 N HCl (2×20 mL). The combined aqueous phases were saturated with NaCl and back-extracted with CHCl₃ (4×50 mL). The combined organic phases were passed through a hydrophobic fit and the solvent removed in vacuo. The residue was then purified by preparative HPLC to give the title compound as a white solid (40 mg, 10% yield).

¹H NMR (400 MHz, DMSO): δ 8.62 (s, 2H), 7.73 (d, J=3.8 Hz, 1H), 7.42-7.31 (m, 6H), 7.08-7.01 (m, 3H), 6.18 (dd, J=4.0, 9.1 Hz, 1H), 4.75-4.69 (m, 1H), 4.04-3.90 (m, 1H), 3.90-3.84 (m, 1H), 3.82 (s, 3H), 3.81-3.79 (m, 1H), 3.62 (dd, J=9.6, 14.1 Hz, 1H), 3.36-3.31 (m, 1H), 3.25-3.21 (m, 1H), 3.15-3.04 (m, 1H), 2.88-2.82 (m, 1H), 2.73-2.66 (m, 2H), 2.41-2.38 (m, 1H), 1.96-1.94 (m, 1H), 1.82-1.80 (m, 1H), 1.59-1.44 (m, 4H), 1.33-1.17 (m, 2H). LCMS (Method 1): [MH+]=740 at 2.32 min.

The following compounds were synthesized via a similar method as 1:1 mixture of diastereoisomers.

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[[[3-oxo-2-phenyl-3-[(3R)-quinuclidin-3-yl]oxy-propyl]amino]methyl]benzoate 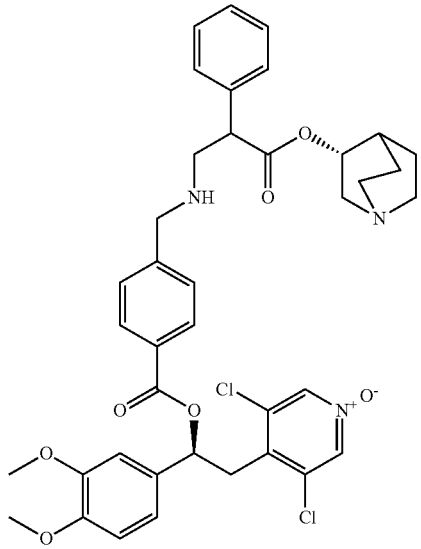 | Example 2 | Intermediate 2 and Intermediate 9 | ¹H NMR (400 MHz, DMSO): δ 8.61 (s, 2 H), 7.97 (d, J = 7.8 Hz, 2 H), 7.48 (d, J = 7.8 Hz, 2 H), 7.40-7.30 (m, 6 H), 7.11-7.01 (m, 2 H), 6.26 (dd, J = 4.3, 9.6 Hz, 1 H), 4.74-4.68 (m, 1 H), 3.92-3.72 (m, 9 H), 3.64 (dd, J = 9.6, 14.1 Hz, 1 H), 3.39-3.33 (m, 1 H), 3.23-3.05 (m, 2 H), 2.85-2.75 (m, 1 H), 2.74-2.66 (m, 2 H), 2.41-2.33 (m, 1 H), 1.94-1.92 (m, 1 H), 1.82-1.80 (m, 1 H), 1.66-1.48 (m, 4 H), 1.38-1.23 (m, 2 H). LCMS (Method 1): [MH+] = 734 at 2.32 min. |
| [(3R)-quinuclidin-3-yl] 1-[[5-[(1S)-2-(3,5-dichloro-1-oxido-pyridin-1-ium-4-yl)-1-(3,4-dimethoxyphenyl)ethoxy]carbonyl-2-thienyl]methyl-4-phenyl-piperidine-4-carboxylate 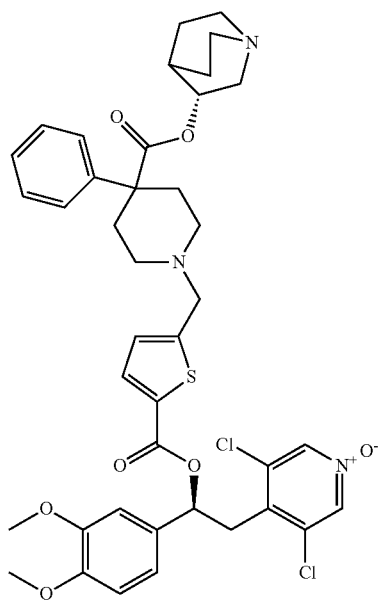 | Example 3 | Intermediate 1 and Intermediate 10 | ¹H NMR (400 MHz, DMSO): δ 8.56 (s, 2 H), 7.69 (d, J = 3.9 Hz, 1 H), 7.42-7.33 (m, 4 H), 7.27 (tt, J = 1.7, 6.8 Hz, 1 H), 7.05 (d, J = 3.8 Hz, 1 H), 7.02 (s, 1 H), 6.98 (s, 2 H), 6.13 (dd, J = 4.6, 9.4 Hz, 1 H), 4.69-4.63 (m, 1 H), 3.77 (s, 3 H), 3.75 (s, 3 H), 3.71 (s, 2 H), 3.59 (dd, J = 9.7, 13.8 Hz, 1 H), 3.40 (s, 2 H), 3.30 (dd, J = 4.2, 14.2 Hz, 1 H), 3.07-2.99 (m, 1 H), 2.82-2.74 (m, 2 H), 2.70-2.55 (m, 4 H), 2.35-2.16 (m, 3 H), 1.93-1.85 (m, 2 H), 1.80-1.75 (m, 1 H), 1.57-1.48 (m, 1 H), 1.46-1.39 (m, 2 H), 1.27-1.17 (m, 1 H). LCMS (Method 1): [MH+] = 780 at 2.36 min. |

Example 4. [(1S)-2-(3,5-dichloro-1-oxido-pyridin-1-ium-4-yl)-1-(3,4-dimethoxyphenyl)ethyl]-5-[[[3-[(3R)-1-methylpyrrolidin-3-yl]oxy-3-oxo-2-phenyl-propyl]amino]methyl]thiophene-2-carboxylate

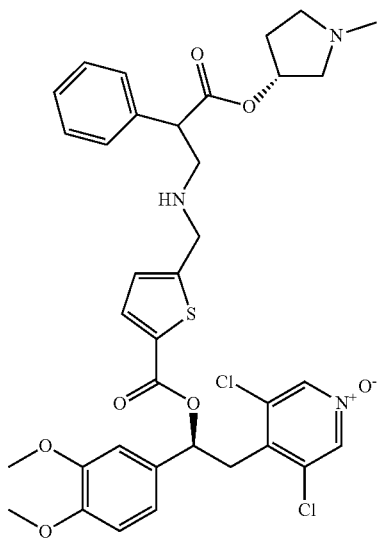

To a solution of [(3R)-1-methylpyrrolidin-3-yl] 3-(tert-butoxycarbonylamino)-2-phenyl-propanoate (Intermediate 7) (681 mg, 1.95 mmol) in dioxane (6 mL) was added 4 N HCl solution in dioxane (6.0 mL, 6.0 mmol) and the resulting mixture was stirred at room temperature for 18 hours. The solvent was removed in vacuo and the residue was taken up in DCM (50 mL) and washed with saturated aqueous NaHCO₃ (20 mL). The organic layer was dried over a hydrophobic frit and the solvent was removed in vacuo. The crude residue (232 mg, 0.93 mmol) was dissolved in acetonitrile (3 mL) and [(1S)-2-(3,5-dichloro-1-oxido-pyridin-1-ium-4-yl)-1-(3,4-dimethoxyphenyl)ethyl] 5-formylthiophene-2-carboxylate (Intermediate 1) (320 mg, 0.67 mmol) was added followed by acetic acid (90 µL, 1.34 mmol). The resultant solution was stirred at room temperature for 18 hours. NaBH(OAc)₃ (442 mg, 2.01 mmol) was then added and the resulting mixture was stirred at room temperature for 18 hours. The solvent was removed in vacuo and the residue was taken up in H₂O (20 mL) and EtOAc (20 mL). The layers were separated and the aqueous phase was extracted with EtOAc (2×20 mL) and the combined organic extracts were passed through a hydrophobic frit and the solvent were removed in vacuo. Purification of the crude material by preparative HPLC afforded the title compound (82 mg, 12%) as a pale yellow solid.

$^1$H NMR (400 MHz, CD₃CN): δ 8.18 (s, 2H), 7.69 (d, J=3.8 Hz, 1H), 7.36-7.30 (m, 5H), 7.07-7.01 (m, 2H), 6.98-6.93 (m, 2H), 6.18 (dd, J=4.5, 9.6 Hz, 1H), 5.17-5.11 (m, 1H), 4.01 (d, J=15.8 Hz, 1H), 3.96 (d, J=15.6 Hz, 1H), 3.83 (s, 3H), 3.83-3.82 (m, 1H), 3.82 (s, 3H), 3.77 (dd, J=6.2, 9.6 Hz, 1H), 3.67 (dd, J=9.7, 14.2 Hz, 1H), 3.34 (dd, J=4.5, 14.1 Hz, 1H), 3.23 (dd, J=9.2, 12.0 Hz, 1H), 2.89 (ddd, J=2.3, 5.9, 11.9 Hz, 1H), 2.71-2.56 (m, 3H), 2.49$^{\dagger or *}$ (d, J=9.1 Hz, 1H), 2.32-2.18 (m, 2H), 2.26$^{\dagger or *}$ (s, 3H), 2.23$^{\dagger or *}$ (s, 3H), 1.81-1.74$^{\dagger or *}$ (m, 1H), 1.67-1.56$^{\dagger or *}$ (m, 1H). † and * refer to different isomers (arbitrarily assigned). LCMS (Method 2): [MH+]=714 at 3.05 min The following compounds were synthesized via a similar method as 1:1 mixture of diastereoisomers.

| Structure | Example number | Precursor | Analytical Data |
| --- | --- | --- | --- |
| [(1S)-2-(3,5-dichloro-1-oxido-pyridin-1-ium-4-yl)-1-(3,4-dimethoxyphenyl)ethyl] 5-[[[3-[(1-methyl-4-piperidyl)oxy]-3-oxo-2-phenyl-propyl]amino]methyl]thiophene-2-carboxylate | Example 5 | Intermediate 1 and Intermediate 8 | $^1$H NMR (400 MHz, CD₃CN): δ 8.18 (s, 2 H), 7.68 (d, J = 3.8 Hz, 1 H), 7.37-7.29 (m, 5 H), 7.07-7.01 (m, 2 H), 6.97-6.93 (m, 2 H), 6.17 (dd, J = 4.5, 9.6 Hz, 1 H), 4.79-4.72 (m, 1 H), 4.01 (d, J = 13.4 Hz, 1 H), 3.96 (d, J = 14.2 Hz, 1 H), 3.83 (s, 3 H), 3.83-3.80 (m, 1 H), 3.82 (s, 3 H), 3.77 (dd, J = 5.7, 8.8 Hz, 1 H), 3.67 (dd, J = 9.8, 14.0 Hz, 1 H), 3.34 (dd, J = 4.4, 14.4 Hz, 1 H), 3.25 (dd, J = 9.1, 11.9 Hz, 1 H), 2.90 (ddd, J = 2.0, 6.1, 11.9 Hz, 1 H), 2.54-2.47 (m, 1 H), 2.44-2.37 (m, 1 H), 2.25-2.13 (m, 2 H), 2.15 (s, 3 H), 1.90-1.80 (m, 1 H), 1.79-1.70 (m, 1 H), 1.69-1.59 (m, 1 H), 1.59-1.47 (m, 1 H). LCMS (Method 1): [MH+] = 728 at 2.29 min. |

| Structure | Example number | Precursor | Analytical Data |
|---|---|---|---|
| (1S)-2-(3,5-dichloro-1-oxido-pyridin-1-ium-4-yl)-1-(3,4-dimethoxyphenyl)ethyl] 5-[[[3-(2-dimethyl-aminoethyloxy)-3-oxo-2-phenyl-propyl]amino]methyl]thiophene-2-carboxylate 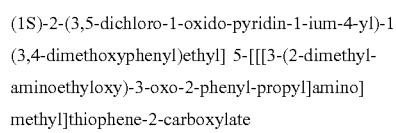 | Example 6 | Intermediate 1 and Intermediate 6 | $^1$H NMR (400 MHz, CDCl$_3$): δ 8.13 (s, 2 H), 7.63 (d, J = 3.8 Hz, 1 H), 7.35-7.25 (m, 5 H), 7.01-6.97 (m, 2 H), 6.88-6.83 (m, 2 H), 6.22 (dd, J = 4.4, 9.7 Hz, 1 H), 4.26-4.14 (m, 2 H), 3.99 (s, 2 H), 3.90 (s, 3 H), 3.88 (s, 3 H), 3.88-3.83 (m, 1 H), 3.66 (dd, J = 9.6, 13.9 Hz, 1 H), 3.34-3.27 (m, 2 H), 2.94 (ddd, J = 2.0, 6.2, 12.0 Hz, 1 H), 2.50 (dd, J = 5.8, 5.8 Hz, 2 H), 2.18 (s, 6 H), NH not visible. LCMS (Method 2): [MH+] = 702 at 2.75 min. |
| [(1S)-2-(3,5-dichloro-1-oxido-pyridin-1-ium-4-yl)-1-(3,4-dimethoxyphenyl)ethyl] 5-[[[2-methyl-3-oxo-2-phenyl-3-[(3R)-quinuclidin-3-yl]oxy-propyl]amino]methyl]thiophene-2-carboxylate 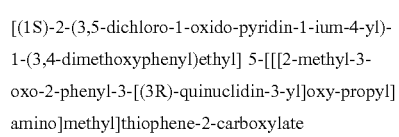 | Example 7 | Intermediate 1 and Intermediate 13 | $^1$H NMR (400 MHz, DMSO): δ 8.49$^{†or*}$ (s, 2 H), 8.48$^{†or*}$ (s, 2 H), 7.60$^{†or*}$ (d, J = 3.8 Hz, 1 H), 7.59$^{†or*}$ (d, J = 4.0 Hz, 1 H), 7.29-7.17 (m, 5 H), 6.96-6.92 (m, 2 H), 6.91-6.88 (m, 2 H), 6.06 (dd, J = 4.5, 9.3 Hz, 1 H), 4.64-4.59$^{†or*}$ (m, 1 H), 4.58-4.53$^{†or*}$ (m, 1 H), 3.92-3.82 (m, 2 H), 3.71$^{†or*}$ (s, 3 H), 3.70$^{†or*}$ (s, 3 H), 3.68 (s, 3 H), 3.51 (dd, J = 9.6, 13.6 Hz, 1 H), 3.22-3.19 (m, 1 H), 3.16-3.07 (m, 1 H), 3.00-2.84 (m, 2 H), 2.59-2.46 (m, 4 H), 2.35 (d, J = 14.4 Hz, 1 H, 2.28-2.22$^{†or*}$ (m, 1 H), 1.78-1.74$^{†or*}$ (m, 1 H), 1.62-1.57$^{†or*}$ (m, 1 H), 1.48$^{†or*}$ (s, 3 H), 1.46$^{†or*}$ (s, 3 H), 1.39-1.25 (m, 3 H), 1.16-1.06$^{†or*}$ (m, 1 H), 1.05-0.98$^{†or*}$ (m, 1 H). NH not visible, † and * refer to different isomers (arbitrarily assigned). LCMS (Method 1): [MH+] = 754 at 2.38 min. |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[2-methyl-3-[(1-methyl-4-piperidyl)oxy]-3-oxo-2-phenyl-propyl]amino]methyl]thiophene-2-carboxylate 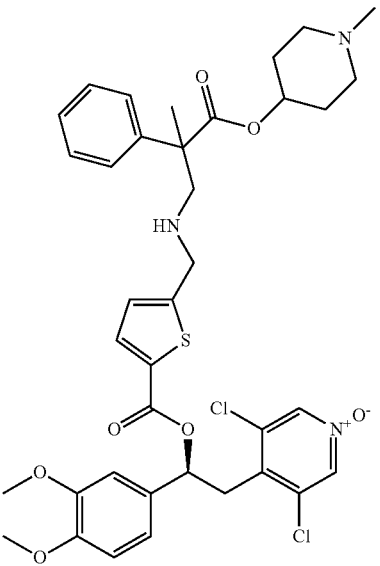 | Example 8 | Intermediate 1 and Intermediate 11 | $^1$H NMR (400 MHz, CD$_3$CN): δ 8.18 (s, 2 H), 7.67 (dd, J = 1.3, 3.8 Hz, 1 H), 7.38-7.32 (m, 4 H), 7.30-7.24 (m, 1 H), 7.07-7.01 (m, 2 H), 6.97-6.93 (m, 2 H), 6.18 (dd, J = 4.5, 9.6 Hz, 1 H), 4.82-4.76 (m, 1 H), 3.99 (d, J = 15.3 Hz, 1 H), 3.94 (d, J = 15.3 Hz, 1 H), 3.85-3.79 (m, 1 H), 3.83 (s, 3 H), 3.82 (s, 3 H), 3.67 (dd, J = 9.9, 14.1 Hz, 1 H), 3.34 (dd, J = 4.5, 14.1 Hz, 1 H), 3.21 (d, J = 11.6 Hz, 1 H), 2.97 (dd, J = 3.9, 11.7 Hz, 1 H), 2.41-2.34 (m, 2 H), 2.23-2.10 (m, 2 H), 2.13 (s, 3 H), 1.81-1.76 (m, 2 H), 1.59 (s, 3 H), 1.64-1.49 (m, 2 H). LCMS (Method 1): [MH+] = 742 at 2.33 min. |
| [(1S)-2-(3,5-dichloro-1-oxido-pyridin-1-ium-4-yl)-1-(3,4-dimethoxyphenyl)ethyl] 5-[[[3-(2-dimethyl-aminoethyloxy)-2-methyl-3-oxo-2-phenyl-propyl]amino]methyl]thiophene-2-carboxylate 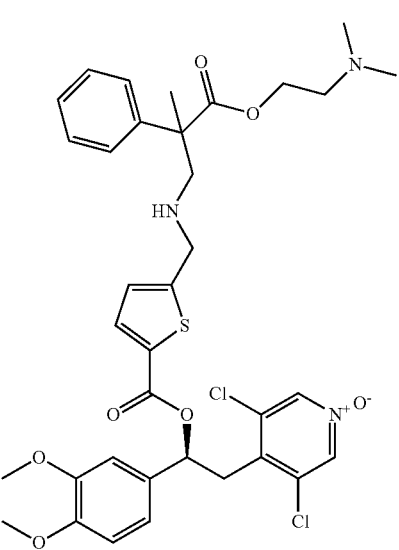 | Example 9 | Intermediate 1 and Intermediate 12 | $^1$H NMR (400 MHz, CD$_3$CN): δ 8.19$^{†or*}$ (s, 2 H), 8.18$^{†or*}$ (s, 2 H), 7.68 (d, J = 3.5 Hz, 1 H), 7.38-7.30 (m, 4 H), 7.30-7.24 (m, 1 H), 7.07-7.00 (m, 2 H), 6.96-6.92 (m, 2 H), 6.18 (dd, J = 4.5, 9.6 Hz, 1 H), 4.32-4.24 (m, 1 H), 4.13-4.06 (m, 1 H), 4.03-3.94 (m, 2 H), 3.84$^{†or*}$ (s, 3 H), 3.83$^{†or*}$ (s, 3 H), 3.82 (s, 3 H), 3.67 (dd, J = 9.7, 14.0 Hz, 1 H), 3.35 (dd, J = 4.5, 13.6 Hz, 1 H), 3.26 (d, J = 12.1 Hz, 1 H), 2.91 (dd, J = 4.5, 11.6 Hz, 1 H), 2.48-2.42 (m, 2 H), 2.11 (s, 6 H), 1.59 (s, 3 H). † and * refer to different isomers (arbitrarily assigned), NH not visible. LCMS (Method 1): [MH+] = 716 at 2.31 min. |

Example 10. [(1S)-2-(3,5-dichloro-1-oxido-pyridin-1-ium-4-yl)-1-(3,4-dimethoxyphenyl)ethyl]-5-[[methyl-[2-methyl-3-oxo-2-phenyl-3-[(3R)-quinuclidin-3-yl]oxy-propyl]amino]methyl]thiophene-2-carboxylate Example 11. [(3R)-quinuclidin-3-yl]-1-[[4-[(1S)-2-(3,5-dichloro-1-oxido-pyridin-1-ium-4-yl)-1-(3,4-dimethoxyphenyl)ethoxy]-carbonylphenyl]methyl]-4-phenyl-piperidine-4-carboxylate

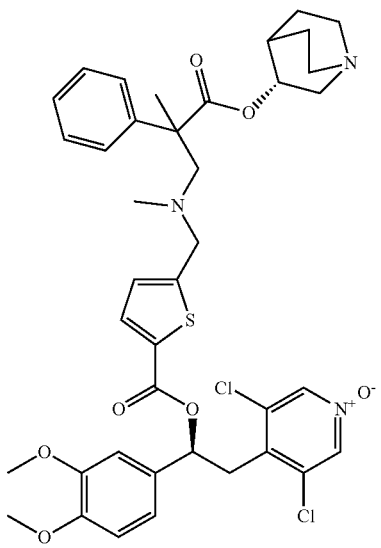

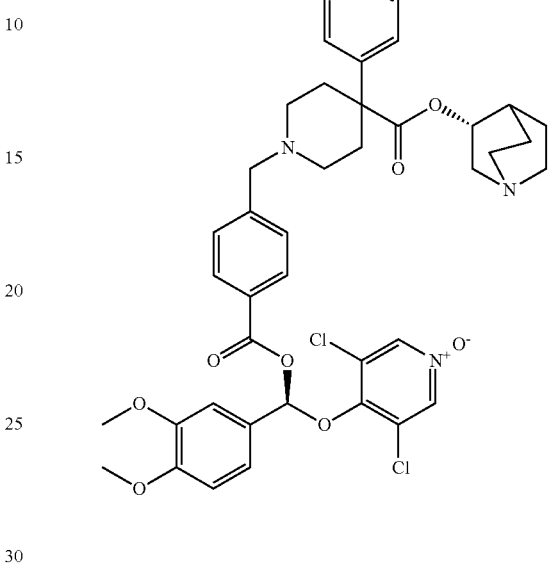

To a mixture of [(1S)-2-(3,5-dichloro-1-oxido-pyridin-1-ium-4-yl)-1-(3,4-dimethoxyphenyl)ethyl] 5-[[[2-methyl-3-oxo-2-phenyl-3-[(3R)-quinuclidin-3-yl]oxy-propyl]amino]methyl]thiophene-2-carboxylate (Example 7) (117 mg, 0.18 mmol) and formic acid (0.30 mL) in aqueous formaldehyde (37%, 6 mL) was added NaBH$_3$CN (48 mg, 0.78 mmol) at room temperature. The reaction mixture was stirred for one hour and diluted with DCM (50 mL) and saturated aqueous NaHCO$_3$ (20 mL). The resulting slurry was stirred vigorously for 30 minutes until the layers were clear. The organic layer was passed through a hydrophobic fit and the solvent was removed in vacuo. The crude residue was purified by preparative HPLC to give the title compound as a white solid (120 mg, 87% yield).

$^1$H NMR (400 MHz, CD$_3$CN): δ 8.18$^{\dagger or *}$ (s, 2H), 8.18$^{\dagger or *}$ (s, 2H), 7.64 (dd, J=1.8, 3.8 Hz, 1H), 7.42-7.39 (m, 2H), 7.37-7.32 (m, 2H), 7.28-7.24 (m, 1H), 7.06-7.00 (m, 2H), 6.94 (d, J=8.3 Hz, 1H), 6.91-6.88 (m, 1H), 6.16 (ddd, J=2.5, 4.5, 9.6 Hz, 1H), 4.78-4.72 (m, 1H), 3.82 (s, 3H), 3.80 (s, 3H), 3.79 (d, J=2.1 Hz, 1H), 3.76-3.63 (m, 2H), 3.33 (dd, J=4.1, 14.1 Hz, 2H), 3.17-3.03 (m, 1H), 2.92 (dd, J=10.9, 13.6 Hz, 1H), 2.72-2.56 (m, 4H), 2.54-2.45 (m, 1H), 2.17$^{\dagger or *}$ (s, 3H), 2.16$^{\dagger or *}$ (s, 3H), 1.91-1.88$^{\dagger or *}$ (m, 1H), 1.84-1.77$^{\dagger or *}$ (m, 1H), 1.71$^{\dagger or *}$ (s, 3H), 1.69$^{\dagger or *}$ (s, 3H), 1.64-1.45 (m, 3H), 1.32-1.22 (m, 1H). † and * refer to different isomers (arbitrarily assigned). LCMS (Method 2): [MH+]=768 at 3.83 min.

To a mixture of [(1S)-2-(3,5-dichloro-1-oxido-pyridin-1-ium-4-yl)-1-(3,4-dimethoxyphenyl)ethyl] 4-formylbenzoate (intermediate 2) (24 mg, 0.05 mmol) and [(3R)-quinuclidin-3-yl] 4-phenylpiperidine-4-carboxylate dihydrochloride (intermediate 10) (39 mg, 0.1 mmol) in MeOH (1 mL) was added NaBH$_3$CN (6 mg, 0.1 mmol). The mixture was stirred at room temperature for 18 hours and further NaBH$_3$CN (6 mg, 0.1 mmol) was added. The mixture was stirred at room temperature for 6 hours and then the solvent was removed in vacuo. The residue was taken up in H$_2$O (10 mL) and EtOAc (20 mL). The layers were separated and saturated aqueous NaHCO$_3$ (10 mL) was added to the aqueous phase, which was then extracted with EtOAc (2×20 mL). The combined organic fractions were extracted with 0.2 M aqueous hydrochloric acid (40 mL) and H$_2$O (30 mL). The aqueous extracts were combined and NaCl (6.5 g) was added. The mixture was extracted with CHCl$_3$ (3×30 mL) and the combined organic extracts were washed with saturated aqueous NaHCO$_3$ (30 mL), passed through a hydrophobic fit and the solvent removed in vacuo. Purification of the crude material by preparative HPLC afforded the title compound as an off-white solid (5 mg, 13%).

$^1$H NMR (400 MHz, CD$_3$CN): δ 8.18 (s, 2H), 8.00 (d, J=8.3 Hz, 2H), 7.48-7.41 (m, 4H), 7.41-7.34 (m, 2H), 7.32-7.26 (m, 1H), 7.10-7.02 (m, 2H), 6.94 (d, J=8.3 Hz, 1H), 6.24 (dd, J=4.5, 9.6 Hz, 1H), 4.73-4.67 (m, 1H), 3.83 (s, 3H), 3.81 (s, 3H), 3.71 (dd, J=9.6, 14.1 Hz, 1H), 3.55 (s, 2H), 3.36 (dd, J=4.5, 14.1 Hz, 1H), 3.07 (ddd, J=2.1, 8.2, 14.7 Hz, 1H), 2.83-2.12 (m, 13H), 1.85-1.77 (m, 1H), 1.66-1.43 (m, 3H), 1.34-1.22 (m, 1H). LCMS (Method 1): [MH+]=774 at 2.35 min.

Example 12. [(3R)-quinuclidin-3-yl]-1-[2-[4-[(1S)-2-(3,5-dichloro-1-oxido-pyridin-1-ium-4-yl)-1-(3,4-dimethoxyphenyl)ethoxy]carbonylphenyl]ethyl]-4-phenyl-piperidine-4-carboxylate

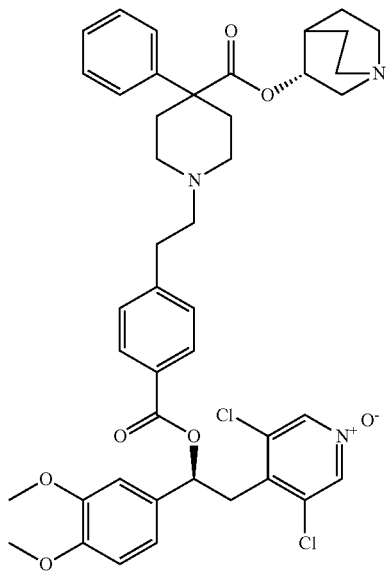

To a mixture of [(1S)-2-(3,5-dichloro-1-oxido-pyridin-1-ium-4-yl)-1-(3,4-dimethoxyphenyl)-ethyl] 4-(1,3-dioxolan-2-ylmethyl)benzoate (intermediate 14)(268 mg, 0.5 mmol) in THF (10 mL) was added 2 N aqueous hydrochloric acid (10 mL) and the mixture was heated to 40° C. for 6 hours. DCM (20 mL) and H$_2$O (10 mL) were added and the mixture was passed through a hydrophobic fit and the solvent was removed in vacuo. The residue was taken up in EtOH (10 mL) and to half of this mixture (5 mL) was added [(3R)-quinuclidin-3-yl] 4-phenylpiperidine-4-carboxylate dihydrochloride (intermediate 10) (97 mg, 0.25 mmol) and NaBH$_3$CN (31 mg, 0.5 mmol). The mixture was allowed to stir at room temperature for 18 hours and then the solvent was removed in vacuo. The residue was taken up in saturated aqueous NaHCO$_3$ (10 mL) and EtOAc (20 mL). The organic phase was extracted with 0.2 N aqueous hydrochloric acid (40 mL) and H$_2$O (30 mL). The aqueous extracts were combined and NaCl (6.5 g) was added. The mixture was extracted with CHCl$_3$ (3×30 mL) and the combined organic extracts were washed with saturated aqueous NaHCO$_3$ (30 mL), passed through a hydrophobic frit and the solvent was removed in vacuo. Purification of the crude material by preparative HPLC afforded the title compound as an off-white solid (15 mg, 8%).

$^1$H NMR (400 MHz, CD$_3$CN): ä 8.17 (s, 2H), 7.97 (d, J=8.3 Hz, 2H), 7.48-7.44 (m, 2H), 7.41-7.34 (m, 4H), 7.31-7.26 (m, 1H), 7.09-7.03 (m, 2H), 6.94 (d, J=8.1 Hz, 1H), 6.23 (dd, J=4.7, 9.5 Hz, 1H), 4.76-4.70 (m, 1H), 3.83 (s, 3H), 3.81 (s, 3H), 3.70 (dd, J=9.5, 14.0 Hz, 1H), 3.36 (dd, J=4.5, 14.1 Hz, 1H), 3.09 (ddd, J=2.1, 8.2, 14.7 Hz, 1H), 2.92-2.82 (m, 4H), 2.79-2.54 (m, 9H), 2.43 (td, J=2.8, 14.7 Hz, 1H), 2.32-2.21 (m, 2H), 1.99-1.84 (m, 2H), 1.68-1.46 (m, 3H), 1.37-1.25 (m, 1H). LCMS (Method 1): [MH+]=788 at 2.37 min.

The following compound was synthesized following the same procedure.

| Structure | Example Number | Precursor | Analytical Data |
|---|---|---|---|
| [(3R)-quinuclidin-3-yl] 1-[2-[3-[(1S)-2-(3,5-dichloro-1-oxido-pyridin-1-ium-4-yl)-1-(3,4-dimethoxyphenyl)ethoxy]carbonyl-phenyl]ethyl]-4-phenyl-piperidine-4-carboxylate 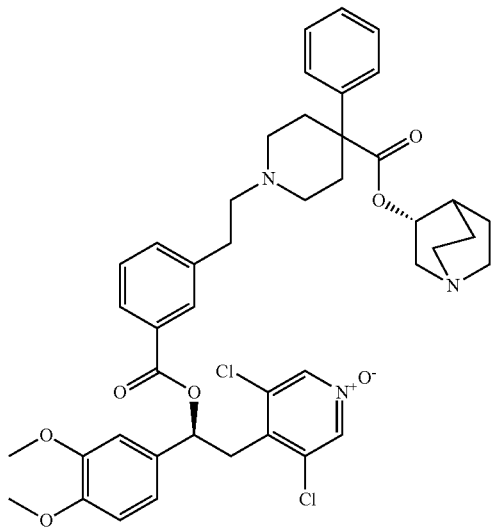 | Example 13 | Intermediate 10 and Intermediate 15 | $^1$H NMR (400 MHz, CD$_3$CN): δ 8.18 (s, 2 H), 7.95 (s, 1 H), 7.87 (d, J = 7.8 Hz, 1 H), 7.52-7.43 (m, 3 H), 7.42-7.34 (m, 3 H), 7.30-7.25 (m, 1 H), 7.08 (d, J = 2.0 Hz, 1 H), 7.04 (dd, J = 2.0, 8.3 Hz, 1 H), 6.91 (d, J = 8.3 Hz, 1 H), 6.23 (dd, J = 4.5, 9.6 Hz, 1 H), 4.74- 4.69 (m, 1 H), 3.82 (s, 3 H), 3.80 (s, 3 H), 3.69 (dd, J = 9.6, 14.1 Hz, 1 H), 3.35 (dd, J = 4.8, 14.1 Hz, 1 H), 3.06 (ddd, J = 2.1, 8.2, 14.7 Hz, 1 H), 2.94-2.81 (m, 4 H), 2.76-2.54 (m, 9 H), 2.40 (td, J = 2.8, 14.8 Hz, 1 H), 2.34-2.21 (m, 2 H), 2.03-1.80 (m, 2 H), 1.66-1.43 (m, 3 H), 1.35-1.23 (m, 1 H). LCMS (Method 1): [MH+] = 788 at 2.36 min. |

Example 14. [(3R)-quinuclidin-3-yl]-1-[[3-[(1S)-2-(3,5-dichloro-1-oxido-pyridin-1-ium-4-yl)-1-(3,4-dimethoxyphenyl)ethoxy]carbonylphenyl]methyl]-4-phenyl-piperidine-4-carboxylate

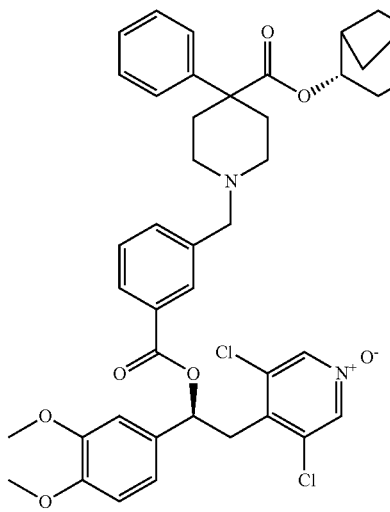

To a stirred mixture of [(1S)-2-(3,5-dichloro-1-oxido-pyridin-1-ium-4-yl)-1-(3,4-dimethoxyphenyl)ethyl] 3-formylbenzoate (intermediate 3) (150 mg, 0.47 mmol) and [(3R)-quinuclidin-3-yl] 4-phenylpiperidine-4-carboxylate dihydrochloride (intermediate 10) (182 mg, 0.47 mmol) in trifluoroethanol (5 mL) at room temperature was added $Et_3N$ (0.13 mL, 0.94 mmol) and acetic acid (0.035 mL, 0.62 mmol). The mixture was stirred at room temperature for 3 days. The solvent was removed in vacuo and azeotroped with toluene (3×30 mL). The residue was suspended in anhydrous $CH_3CN$ (5 mL) and $NaBH(OAc)_3$ (133 mg, 0.62 mmol) was added and the reaction mixture stirred at room temperature for 48 hours. Additional $NaBH(OAc)_3$ (133 mg, 0.62 mmol) was added and the mixture was stirred at room temperature for a further 24 hours. The solvent was removed in vacuo and the residue was partitioned between EtOAc (10 mL) and $H_2O$ (10 mL). The aqueous layer was further extracted with EtOAc (3×10 mL). The aqueous phase was acidified to ~pH 2 with 0.2 N HCl and extracted with $CHCl_3$ (3×10 mL). The combined $CHCl_3$ extracts were filtered through a phase separator and the solvent was removed in vacuo to give the bis hydrochloride salt of the product as a white solid (240 mg, 90%). A portion of this solid (140 mg) was re-dissolved in $CHCl_3$ (10 mL), washed with saturated aqueous $NaHCO_3$ solution (10 mL). The organic phase was filtered through a phase separator frit and the solvent was removed in vacuo to give the free base of the title compound as a white solid (70 mg).

$^1$H NMR (400 MHz, $CD_3CN$): δ 8.18 (s, 2H), 8.02 (s, 1H), 7.93 (d, J=7.8 Hz, 1H), 7.57 (d, J=7.6 Hz, 1H), 7.48-7.42 (m, 3H), 7.37 (dd, J=7.7, 7.7 Hz, 2H), 7.31-7.26 (m, 1H), 7.10-7.03 (m, 2H), 6.93 (d, J=8.1 Hz, 1H), 6.25 (dd, J=4.5, 9.6 Hz, 1H), 4.73-4.69 (m, 1H), 3.83 (s, 3H), 3.81 (s, 3H), 3.71 (dd, J=9.6, 14.1 Hz, 1H), 3.56 (s, 2H), 3.37 (dd, J=4.5, 14.1 Hz, 1H), 3.06 (ddd, J=2.1, 8.1, 14.6 Hz, 1H), 2.78 (d, J=11.1 Hz, 2H), 2.69-2.55 (m, 7H), 2.38 (dd, J=2.3, 14.4 Hz, 1H), 2.26-2.21 (m, 2H), 1.83-1.79 (m, 1H), 1.64-1.45 (m, 3H), 1.30-1.22 (m, 1H). LCMS (Method 1): [MH+]=774 at 2.33 min.

Example 15. [(3R)-quinuclidin-3-yl]-1-[[5-[(1S)-2-(3,5-dichloro-1-oxido-pyridin-1-ium-4-yl)-1-(3,4-dimethoxyphenyl)ethoxy]carbonyl-2-thienyl] methyl]-3-phenyl-azetidine-3-carboxylate

SCHEME C

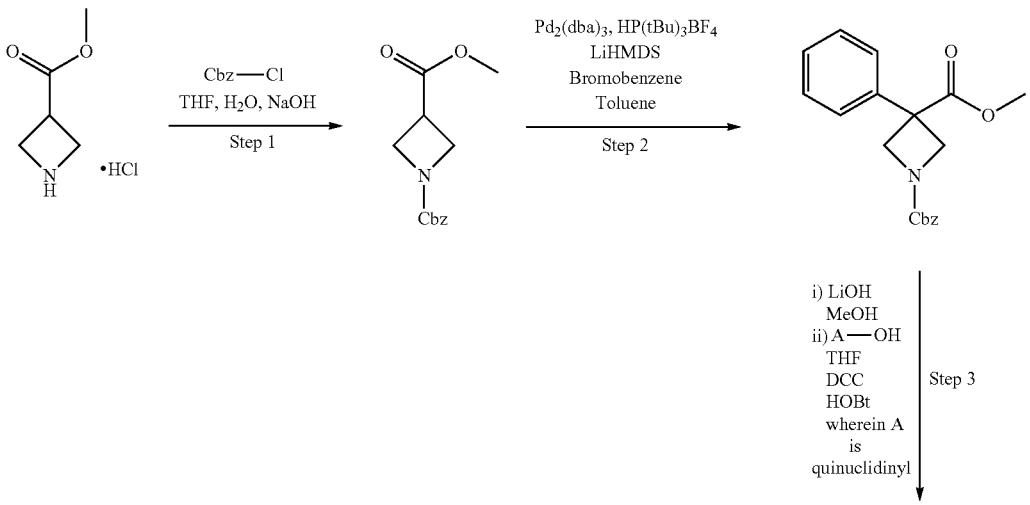

-continued i) HCO₂NH₄, Pd/C, EtOAc ii) 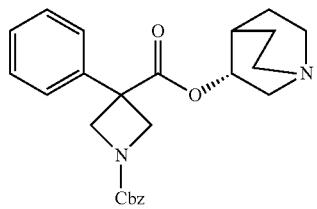

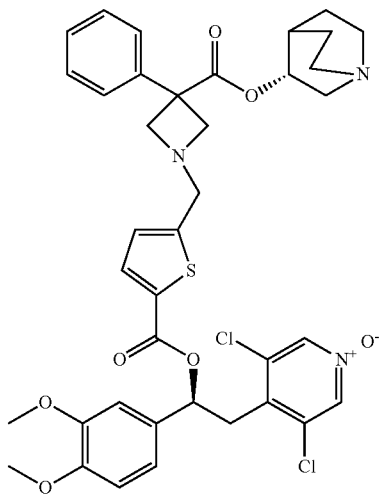

AcOH, trifluoroethanol
iii) Azeotroped with toluene then NaBH(OAc)₃, CH₃CN

Step 4 ←

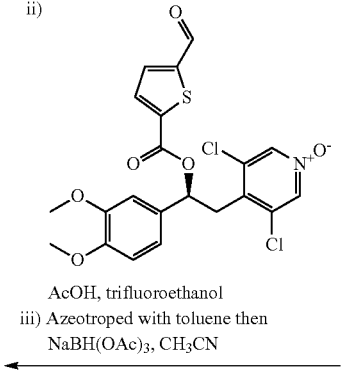

Step 1: Preparation of O1-benzyl-O3-methyl azetidine-1,3-dicarboxylate

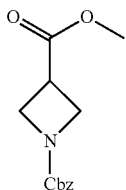 [SMILES: COC(=O)C1CN(C(=O)OCc2ccccc2)C1]

To a round bottomed flask containing methyl azetidine-3-carboxylate hydrochloride (3 g, 20 mmol), THF (30 mL) and H₂O (30 mL) was added an aqueous solution of NaOH (4 M, 5 mL, 20 mmol) at 0° C., followed by benzyl chloroformate (2.84 mL, 20 mmol). The reaction was vigorously stirred at room temperature for 18 hours. The reaction mixture was concentrated in vacuo and the residue partitioned between Et₂O (100 mL) and H₂O (30 mL). The aqueous phase was back-extracted with Et₂O (3×50 mL), the combined organic phases were dried (Na₂SO₄) and concentrated in vacuo to give the title compound (5 g, 99%) as a colourless oil, which was used in subsequent steps without further purification.

¹H NMR (400 MHz, CDCl₃): δ 7.43-7.25 (m, 5H), 5.10 (s, 2H), 4.23-4.13 (m, 4H), 3.74 (s, 3H), 3.38 (q, J=7.2 Hz, 1H).

Step 2: Preparation of O1-benzyl-O3-methyl 3-phenylazetidine-1,3-dicarboxylate

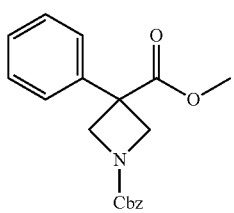 [SMILES: COC(=O)C1(c2ccccc2)CN(C(=O)OCc2ccccc2)C1]

To a round bottomed flask containing Pd₂(dba)₃.HP(tBu)₃ BF₄ (500 mg, 0.38 mmol) under N₂ was added a solution of LiHMDS (1 M in toluene, 48 mL, 48 mol). The reaction was stirred for 20 minutes and cooled to 0° C. Bromobenzene (4.4 mL, 42 mmol) was added, followed by a solution of O1-benzyl O3-methyl azetidine-1,3-dicarboxylate (5 g, 20 mmol) in degassed toluene (60 mL) dropwise under N₂. The reaction was stirred for a further 30 minutes at 0° C., then stirred at room temperature for 18 hours. The reaction was diluted with 10% citric acid solution (50 mL) and extracted with EtOAc (2×100 mL). The combined organic phases were dried (Na₂SO₄), filtered and concentrated in vacuo. The crude residue was purified by silica gel chromatography eluting with 0-20% EtOAc in isohexane to give the title compound, as an oil (420 mg, 6% yield).

¹H NMR (400 MHz, CDCl₃): δ 7.42-7.22 (m, 10H), 5.10 (s, 2H), 4.69 (d, J=8.3 Hz, 2H), 4.39 (d, J=9.0 Hz, 2H), 3.71 (s, 3H). LCMS (Method 2): [MH+]=326 at 3.92 min.

Step 3: Preparation of O1-benzyl-O3-[(3R)-quinuclidin-3-yl]-3-phenylazetidine-1,3-dicarboxylate

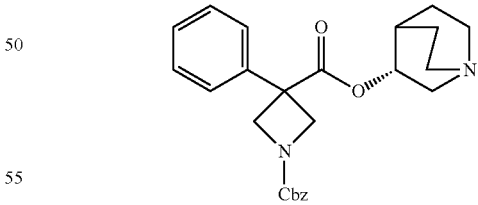

To a stirred solution of O1-benzyl-O3-methyl-3-phenylazetidine-1,3-dicarboxylate (420 mg, 1.29 mmol) in MeOH (5 mL) was added an aqueous solution of 1 N lithium hydroxide (2.6 mL, 2.58 mmol). The reaction mixture was stirred at room temperature for 2 hours. The mixture was acidified by the addition of 2 N hydrochloric acid dropwise to pH 2-3. The mixture was then diluted with DCM (50 mL) and the organic phases were passed through a hydrophobic fit. The solvent was removed in vacuo and the crude material (320 mg, 1.03 mmol) was dissolved in dry THF (5 mL).

N,N'-dicyclohexylcarbodiimide (319 mg, 1.55 mmol), 1-hydroxybenzotriazole (181 mg, 1.55 mmol) and (R)-quinuclidin-3-ol (191 mg, 1.55 mmol) were subsequently added and the resulting slurry was stirred at room temperature for 18 hours. After this time the reaction mixture was filtered through a pad of Celite® and the solvent was removed in vacuo. The residue was partitioned between EtOAc (50 mL) and saturated aqueous $Na_2CO_3$ (2×20 mL). The organic phase was dried ($Na_2SO_4$), filtered and the solvent was removed in vacuo. The residue was purified via silica gel chromatography (eluting with 0-100% of 1:10 7N methanolic ammonia:EtOAc in EtOAc) to give the title compound (178 mg, 41% yield over two steps) as a white solid.

$^1$H NMR (400 MHz, $CDCl_3$): δ 7.40-7.25 (m, 10H), 5.10 (s, 2H), 4.82-4.75 (m, 1H), 4.72-4.66 (m, 2H), 4.41 (dd, J=4.9, 8.5 Hz, 2H), 3.17-3.08 (m, 1H), 2.89-2.61 (m, 4H), 2.48 (d, J=14.7 Hz, 1H), 1.96-1.88 (m, 1H), 1.77-1.36 (m, 3H), 1.28-1.23 (m, 1H).

LCMS (Method 2): [MH+]=421 at 3.77 min.

Step 4: Preparation of [(3R)-quinuclidin-3-yl]-1-[[5-[(1S)-2-(3,5-dichloro-1-oxido-pyridin-1-ium-4-yl)-1-(3,4-dimethoxyphenyl)ethoxy]carbonyl-2-thienyl]methyl]-3-phenyl-azetidine-3-carboxylate

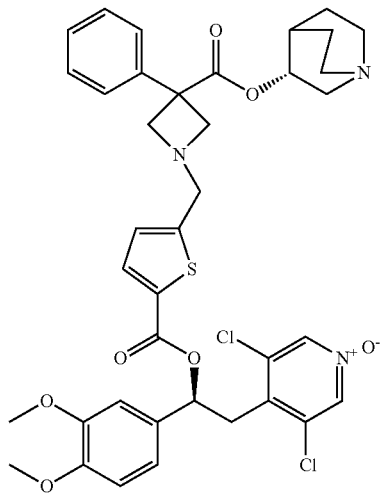

To a solution of O1-benzyl-O3-[(3R)-quinuclidin-3-yl]-3-phenylazetidine-1,3-dicarboxylate (178 mg, 0.43 mmol) in EtOAc (5 mL), was added ammonium formate (210 mg, 3.33 mmol) and 10% Pd/C (100 mg). The mixture was heated to 65° C. for 3 hours. After cooling the slurry to room temperature, the mixture was filtered through a pad of Celite® which was washed with EtOAc (150 mL). The solvent was removed in vacuo to give [(3R)-quinuclidin-3-yl] 3-phenylazetidine-3-carboxylate as a white solid (79 mg, 66%), which was used in the next step without further purification. To a solution of the crude (69 mg, 0.24 mmol) in trifluoroethanol (1 mL) was added acetic acid (0.03 mL, 0.48 mmol) and (S)-3,5-dichloro-4-(2-(3,4-dimethoxyphenyl)-2-((5-formylthiophene-2-carbonyl)oxy)-ethyl)-pyridine 1-oxide (Intermediate 1) (108 mg, 0.24 mmol). The resulting slurry was stirred at room temperature for 18 hours. The solvent was removed in vacuo and the residue was azeotroped with toluene. The residue was taken up in acetonitrile (5 mL), $NaBH(OAc)_3$ (88 mg, 0.48 mmol) was added and the reaction mixture was stirred at room temperature for 1 day. The solvent was removed in vacuo and the residue was diluted with EtOAc (50 mL) and $H_2O$ (20 mL). The aqueous layer was back-extracted with EtOAc (3×50 mL), the combined organic layers were dried ($Na_2SO_4$), filtered and concentrated in vacuo. The crude residue was purified by preparative HPLC to give the title compound as a white solid (40 mg, 22% yield).

$^1$H NMR (400 MHz, DMSO): δ 8.62 (s, 2H), 7.74 (d, J=3.8 Hz, 1H), 7.45-7.40 (m, 2H), 7.37-7.32 (m, 3H), 7.09-7.06 (m, 2H), 7.03 (s, 2H), 6.18 (dd, J=4.3, 9.6 Hz, 1H), 4.76-4.73 (m, 1H), 4.00 (dd, J=6.6, 6.6 Hz, 2H), 3.89 (s, 2H), 3.83 (s, 3H), 3.80 (s, 3H), 3.64 (dd, J=9.7, 14.3 Hz, 1H), 3.56 (t, J=7.1 Hz, 2H), 3.39 (s, 0H), 3.34 (q, J=6.5 Hz, 1H), 3.09 (ddd, J=1.8, 8.1, 14.5 Hz, 1H), 2.74-2.58 (m, 4H), 2.56 (s, 0H), 2.39 (d, J=14.3 Hz, 1H), 1.92-1.87 (m, 1H), 1.64-1.44 (m, 3H), 1.31-1.21 (m, 1H). LCMS (Method 1): [MH+]=752 at 2.42 min.

Example 16. [(3R)-1-methylpyrrolidin-3-yl] 1-[[5-[(1S)-2-(3,5-dichloro-1-oxido-pyridin-1-ium-4-yl)-1-(3,4-dimethoxyphenyl)ethoxy]carbonyl-2-thienyl]methyl]-3-phenyl-azetidine-3-carboxylate

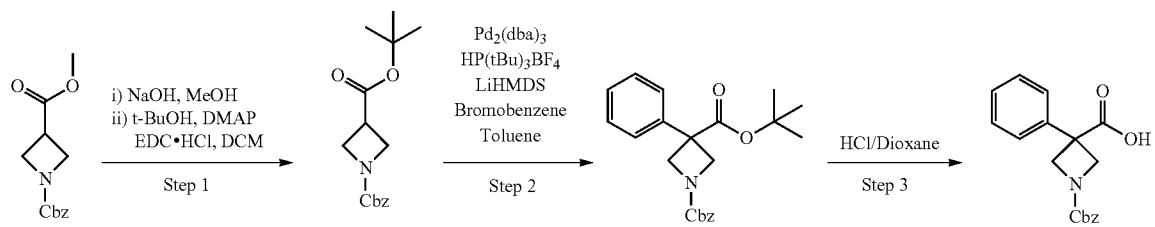

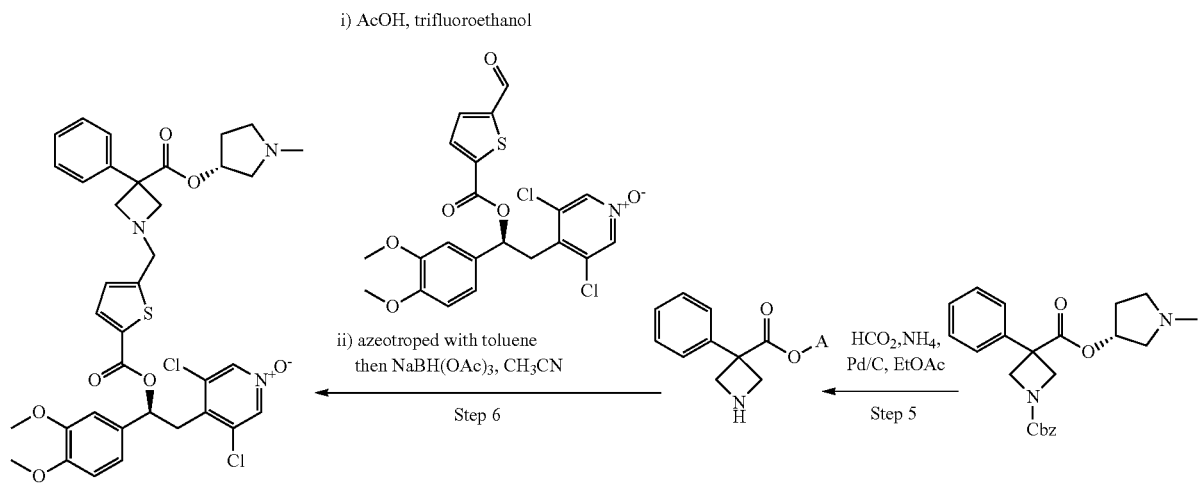

i) AcOH, trifluoroethanol ii) azeotroped with toluene then NaBH(OAc)₃, CH₃CN

Step 6

Step 5

Step 1: Preparation of O1-benzyl-O3-tert-butyl azetidine-1,3-dicarboxylate

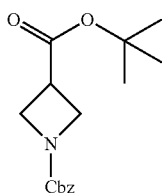 [SMILES: CC(C)(C)OC(=O)C1CN(C(=O)OCc2ccccc2)C1]

To a solution of O1-benzyl-O3-methyl azetidine-1,3-dicarboxylate (6.80 g, 27.3 mmol) in MeOH (100 mL) was added a 2 N NaOH solution (41 mL, 81.9 mmol) and the mixture was stirred at room temperature for 3 hours. The organic solvent was removed in vacuo, the residual solution cooled to 0° C. and acidified to pH 4-5 with 1N HCl and extracted with DCM (3×20 mL). The combined organic extracts were filtered through a phase separator and the solvent was removed in vacuo. The residue was purified by chromatography on silica gel eluting with MeOH/DCM to give a colourless oil. t-BuOH (2.36 g, 31.9 mmol) in DCM (30 mL), DMAP (0.78 g, 6.4 mmol) and EDCI (3.67 g, 19.1 mmol) were added successively to the oil, and the mixture was stirred at room temperature for 3 hours. The solvent was removed in vacuo and the residue was taken up in EtOAc and washed with 10% citric acid (2×20 mL), and saturated NaHCO₃ solution. The organic phase was dried over MgSO₄, filtered and solvent was removed in vacuo to give O1-benzyl O3-tert-butyl azetidine-1,3-dicarboxylate as a colourless oil.

¹H NMR (400 MHz, CDCl₃): δ 7.36-7.34 (m, 5H), 5.10 (s, 2H), 4.14 (d, J=7.7 Hz, 4H), 3.32-3.24 (m, 1H), 1.46 (s, 9H).

Step 2: Preparation of O1-benzyl-O3-tert-butyl-3-phenylazetidine-1,3-dicarboxylate

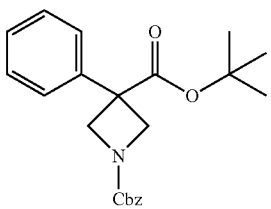 [SMILES: CC(C)(C)OC(=O)C1(c2ccccc2)CN(C(=O)OCc2ccccc2)C1]

To a round bottomed flask containing BF₄H.(tBu)₃P (424 mg, 0.1.5 mmol) and Pd₂(dba)₃ (823 mg, 0.9 mmol) under N₂ was added a 1M solution of LiHMDS in toluene (22.5 mL, 22.0 mol). The reaction mixture was stirred for 10 minutes and bromobenzene (3.35 mL, 22.5 mmol) was added, followed by a solution of O1-benzyl O3-tert-butyl azetidine-1,3-dicarboxylate (3.27 g, 11.2 mmol) in degassed toluene (25 mL) dropwise under N₂. The reaction was stirred at room temperature for 1.5 hours. The reaction was diluted with 10% citric acid solution (100 mL) and extracted with EtOAc (2×100 mL). The combined organic phases were washed with brine, dried over MgSO₄, filtered and concentrated in vacuo. The crude residue was purified by silica gel chromatography eluting with 0-30% EtOAc in isohexane to give the title compound as a yellow oil which solidified on standing (1.4 g, 34%). Impure fractions were re-purified to give a second batch of the title compound as a yellow oil which solidified on standing (684 mg, 16%).

¹H NMR (400 MHz, CDCl₃): δ 7.39-7.25 (m, 10H), 5.10 (s, 2H), 4.63 (d, J=8.8 Hz, 2H), 4.33 (d, J=8.7 Hz, 2H), 1.38 (s, 9H).

Step 3: Preparation of 1-benzyloxycarbonyl-3-phenyl-azetidine-3-carboxylic acid

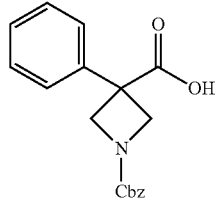 [SMILES: O=C(OCc1ccccc1)N1CC(C(=O)O)(c2ccccc2)C1]

A solution of O1-benzyl-O3-tert-butyl-3-phenylazetidine-1,3-dicarboxylate (402 mg, 1.09 mmol) in 4 N HCl in dioxane (1.4 mL, 5.48 mmol) was stirred at room temperature overnight. Additional 4 N HCl in dioxane (1.4 mL, 5.48 mmol) was added to the mixture and the stirring was maintained at room temperature overnight. The solvent was removed in vacuo, co-evaporated with CH₃CN to give the title compound as a yellow solid (327 mg, 96%). LCMS (Method 2): [MH−]=310 at 2.53 min.

Step 4: Preparation of O1-benzyl-O3-[(3R)-1-methylpyrrolidin-3-yl] 3-phenylazetidine-1,3-dicarboxylate

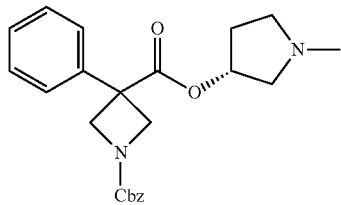 [SMILES: CN1CC[C@@H](OC(=O)C2(c3ccccc3)CN(C(=O)OCc3ccccc3)C2)C1]

To a stirred suspension of 1-benzyloxycarbonyl-3-phenyl-azetidine-3-carboxylic acid (352 mg, 1.04 mmol) in CHCl₃ (20 mL) 2 drops of DMF were added. The mixture was cooled in an ice-bath and oxalyl chloride (0.14 mL, 1.67 mmol) was added dropwise. After stirring in the cold bath for a further 10 minutes the mixture was stirred at room temperature for 2 hours. The solvent was removed in vacuo, co-evaporated further with CHCl₃ (20 mL). The residue was taken up with CHCl₃ (5 mL) and the resulting solution was added dropwise to a solution of (R)-1-methylpyrrolidin-3-ol (0.13 mL, 1.15 mmol) in CHCl₃ (5 mL) at 0° C. under N₂. The mixture was stirred at 0° C. for 30 minutes and allowed to warm to room temperature overnight. The reaction mixture was washed with H₂O (2×10 mL), the organic phase was separated and the solvent removed in vacuo. The residue was taken up in EtOAc (20 mL) and washed with saturated NaHCO₃ solution (2×10 mL). The organic phase was separated, filtered through a phase separator and the solvent removed in vacuo to give the title compound as a brown gum (301 mg, 73%).

LCMS (Method 1): [MH+]=395 at 2.69 min.

Step 5: Preparation of [(3R)-1-methylpyrrolidin-3-yl]-3-phenylazetidine-3-carboxylate

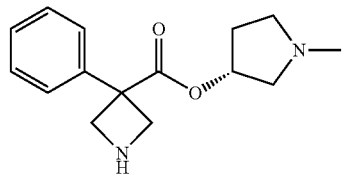 [SMILES: CN1CC[C@@H](OC(=O)C2(c3ccccc3)CNC2)C1]

To a solution of O1-benzyl-O3-[(3R)-1-methylpyrrolidin-3-yl]-3-phenylazetidine-1,3-dicarboxylate (301 mg, 0.76 mmol) in EtOAc (10 mL) was added 10% Pd/C (200 mg) followed by ammonium formate (310 mg, 4.96 mmol) and the mixture was heated at 60° C. for 4 hours. The mixture was allowed to stand at room temperature overnight then filtered through a Celite® cartridge, washed through with EtOAc (100 mL) and the filtrate was evaporated in vacuo to give the title compound as a pale yellow gum (159 mg, 80%). LCMS (Method 2): [MH+]=261 at 2.27 min.

Step 6: Preparation of [(3R)-1-methylpyrrolidin-3-yl]-1-[[5-[(1S)-2-(3,5-dichloro-1-oxido-pyridin-1-ium-4-yl)-1-(3,4-dimethoxyphenyl)ethoxy]carbonyl-2-thienyl]methyl]-3-phenyl-azetidine-3-carboxylate

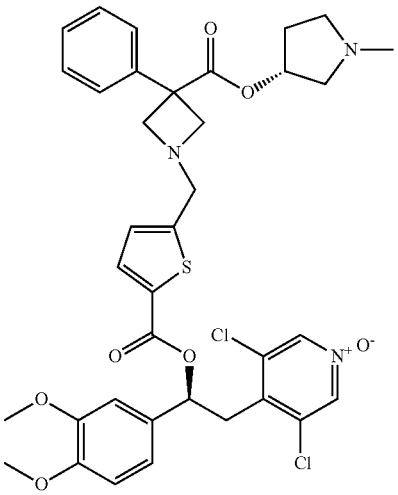

To a stirred mixture of [(1S)-2-(3,5-dichloro-1-oxido-pyridin-1-ium-4-yl)-1-(3,4-dimethoxyphenyl)ethyl] 5-formylthiophene-2-carboxylate (Intermediate 1) (262 mg, 0.54 mmol) and [(3R)-1-methylpyrrolidin-3-yl]-3-phenylazetidine-3-carboxylate (155 mg, 0.60 mmol) in trifluoroethanol (5 mL) at room temperature was added acetic acid (0.062 mL, 1.08 mmol). The mixture was stirred at room temperature overnight. The solvent was removed in vacuo and azeotroped with toluene (3×5 mL). The residue was suspended in anhydrous CH₃CN (5 mL) and NaBH(OAc)₃ (228 mg, 1.08 mmol) was added. The resultant reaction mixture was stirred at room temperature for 48 hours. Additional NaBH(OAc)₃ (50 mg, 0.2 mmol) was added and the mixture was stirred at room temperature for a further 7 hours. The solvent was removed in vacuo and the residue was partitioned between EtOAc (25 mL) and H₂O (25 mL). The aqueous layer was further extracted with EtOAc (20 mL). The combined organic extracts were washed with brine (20 mL), separated, filtered through a phase separator and the solvent was removed in vacuo to give a gum. The residue was re-dissolved in CHCl₃ (10 mL) and washed with saturated NaHCO₃ solution (10 mL). The organic phases were filtered through a phase separator and the solvent was removed in vacuo. The residue was purified by preparative HPLC to give the title compound as a beige solid (72 mg, 18%).

$^1$H NMR (400 MHz, CDCl$_3$): ä 8.15 (s, 2H), 7.63 (d, J=3.8 Hz, 1H), 7.36-7.31 (m, 2H), 7.29-7.27 (m, 3H), 7.01-6.96 (m, 2H), 6.88-6.84 (m, 2H), 6.22 (dd, J=4.5, 9.6 Hz, 1H), 5.25-5.19 (m, 1H), 4.08-4.04 (m, 2H), 3.91 (s, 3H), 3.87 (s, 3H), 3.80 (s, 2H), 3.67 (dd, J=9.9, 13.9 Hz, 1H), 3.55 (d, J=6.6 Hz, 2H), 3.31 (dd, J=4.7, 14.0 Hz, 1H), 2.77-2.62 (m, 2H), 2.50 (dd, J=2.8, 11.1 Hz, 1H), 2.39-2.32 (m, 1H), 2.30 (s, 3H), 2.26-2.16 (m, 1H), 1.77-1.68 (m, 1H). LCMS (Method 2): [MH+]=726 at 3.21 min.

Example 17. Single diastereoisomer of [(1S)-2-(3,5-dichloro-1-oxido-pyridin-1-ium-4-yl)-1-(3,4-dimethoxyphenyl)ethyl] 5-[[[2-hydroxy-3-oxo-3-[(3R)-quinuclidin-3-yl]oxy-2-(2-thienyl)propyl]amino]methyl]thiophene-2-carboxylate

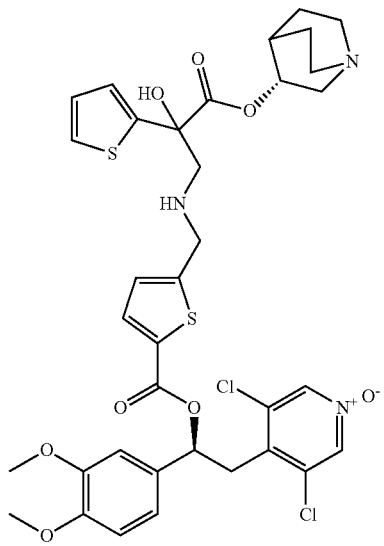

A suspension of [(1S)-2-(3,5-dichloro-1-oxidopyridin-1-ium-4-yl)-1-(3,4-dimethoxyphenyl)ethyl]-5-formylthiophene-2-carboxylate (3.39 g, 7.04 mmol), [(3R)-quinuclidin-3-yl] 3-amino-2-hydroxy-2-(2-thienyl)propanoate bis acetate (3.66 g, 8.80 mmol) and NaBH$_3$CN (1.11 g, 17.6 mmol) in EtOH (60 mL) was stirred at room temperature for 18 hours. The solvent was removed in vacuo and the residue was partitioned between EtOAc (30 mL) and H$_2$O (20 mL). The aqueous layer was further extracted with EtOAc (3×10 mL). The aqueous phase was acidified to ~pH 2 with 0.2 N HCl and extracted with CHCl$_3$ (3×30 mL). The combined CHCl$_3$ extracts were filtered through a phase separator and the solvent was removed in vacuo. The crude residue was purified by preparative HPLC to give the title compound as a white solid (90 mg, 2% yield). The compound was isolated as an apparent single diastereoisomer.

$^1$H NMR (400 MHz, CD$_3$CN): δ 8.19 (s, 2H), 7.66 (d, J=3.8 Hz, 1H), 7.33 (dd, J=1.0, 5.1 Hz, 1H), 7.12 (dd, J=1.1, 3.7 Hz, 1H), 7.06-6.98 (m, 3H), 6.96-6.91 (m, 2H), 6.16 (dd, J=4.7, 9.7 Hz, 1H), 4.83-4.78 (m, 1H), 4.07 (d, J=14.9 Hz, 1H), 3.89 (d, J=15.2 Hz, 1H), 3.82 (s, 3H), 3.80 (s, 3H), 3.65 (dd, J=9.6, 14.1 Hz, 1H), 3.37-3.29 (m, 2H), 3.10-3.02 (m, 2H), 2.73-2.53 (m, 4H), 2.42 (d, J=14.7 Hz, 1H), 1.88-1.84 (m, 1H), 1.76-1.67 (m, 1H), 1.57-1.47 (m, 1H), 1.46-1.36 (m, 1H), 1.30-1.21 (m, 1H), OH and NH not visible. LCMS (Method 3): [MH+]=762 at 2.47 min.

Chiral analysis (Method 8) at 2.09 min.

Example 18 and Example 19

Single diastereoisomers of [(1S)-2-(3,5-dichloro-1-oxido-pyridin-1-ium-4-yl)-1-(3,4-dimethoxyphenyl)ethyl] 5-[[[2-hydroxy-3-oxo-2-phenyl-3-[(3R)-quinuclidin-3-yl]oxy-propyl]amino]methyl]thiophene-2-carboxylate (diastereoisomers 1 and 2)

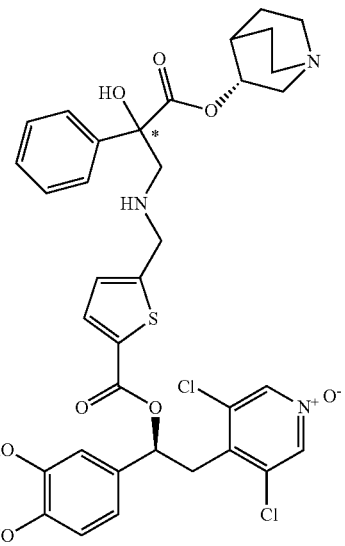

A suspension of [(1S)-2-(3,5-dichloro-1-oxido-pyridin-1-ium-4-yl)-1-(3,4-dimethoxyphenyl)ethyl]-5-formylthiophene-2-carboxylate (350 mg, 0.73 mmol), [(3R)-quinuclidin-3-yl]-2-hydroxy-3-nitro-2-phenyl-propanoate (300 mg, 1.03 mmol) and NaBH(OAc)$_3$ (32 mg, 0.52 mmol) in EtOH (15 mL) was stirred at room temperature for 20 hours. The solvent was removed in vacuo and the residue was partitioned between CHCl$_3$ (30 mL) and brine (30 mL). The aqueous phase was further extracted with CHCl$_3$ (2×30 mL) and the combined organic extracts were filtered through a phase separator fit and the solvent was removed in vacuo. The crude residue was purified by preparative HPLC to give two fractions highly enriched in either single diastereoisomer 1 or 2 (39 mg and 27 mg). Purification of the 39 mg batch by chiral preparative SFC afforded the single diastereoisomer 1 as major compound. Purification of the 27 mg batch by chiral SFC afforded the single diastereoisomer 2 as major compound.

Title compound (Example 18, single diastereoisomer 1) was obtained as a white solid (22.9 mg, 8%).

$^1$H NMR (400 MHz, CD$_3$CN): δ 8.20 (s, 2H), 7.67 (d, J=3.8 Hz, 1H), 7.61-7.57 (m, 2H), 7.41-7.31 (m, 3H), 7.07-7.00 (m, 2H), 6.97-6.92 (m, 2H), 6.17 (dd, J=4.5, 9.6 Hz, 1H), 4.77-4.74 (m, 1H), 4.47 (s, 1H), 4.09 (d, J=14.9 Hz, 1H), 3.92 (d, J=17.2 Hz, 1 H), 3.83 (s, 3H), 3.81 (s, 3H), 3.67 (dd, J=9.6, 14.1 Hz, 1H), 3.47 (d, J=11.9 Hz, 1H), 3.34 (dd, J=4.7, 14.0 Hz, 1H), 3.06-2.95 (m, 2H), 2.68-2.50 (m, 4H), 2.29 (d, J=14.9 Hz, 1H), 1.87-1.84 (m, 1H), 1.70-1.62 (m, 1H), 1.56-1.36 (m, 2H), 1.27-1.18 (m, 1H), NH not observed LCMS (Method 1): [MH+]=756 at 2.32 min. Chiral analysis (Method 7) at 3.08 min.

Title compound (Example 19, single diastereoisomer 2) was obtained as a white solid (13.8 mg, 5%).

$^1$H NMR (400 MHz, CD$_3$CN): δ 8.19 (s, 2H), 7.69 (d, J=3.8 Hz, 1H), 7.61-7.57 (m, 2H), 7.39-7.30 (m, 3H), 7.05-6.96 (m, 3H), 6.93 (d, J=8.1 Hz, 1H), 6.16 (dd, J=4.7, 9.5 Hz, 1H), 4.78-4.74 (m, 1H), 4.38 (s, 1H), 4.10 (d, J=14.9 Hz, 1H), 3.95 (d, J=14.9 Hz, 1H), 3.82 (s, 3H), 3.80 (s, 3H), 3.66 (dd, J=9.7, 14.0 Hz, 1H), 3.49 (d, J=11.5 Hz, 1H), 3.33

(dd, J=4.5, 14.1 Hz, 1H), 3.13 (dd, J=7.8, 14.9 Hz, 1H), 2.98 (d, J=11.9 Hz, 1H), 2.71-2.59 (m, 5H), 2.12-2.08 (m, 1H), 1.86-1.82 (m, 1H), 1.64-1.43 (m, 3H), 1.29-1.20 (m, 1H). LCMS (Method 2): [MH+]=756 at 2.98 min. Chiral analysis (Method 7) at 4.48 min.

Example 20 and Example 21

Single diastereoisomers [(1S)-2-(3,5-dichloro-1-oxido-pyridin-1-ium-4-yl)-1-(3,4-dimethoxyphenyl)ethyl]-5-[[[3-oxo-2-phenyl-3-[(3R)-quinuclidin-3-yl]oxypropyl]amino]-methyl]thiophene-2-carboxylate (diastereoisomers 1 and 2)

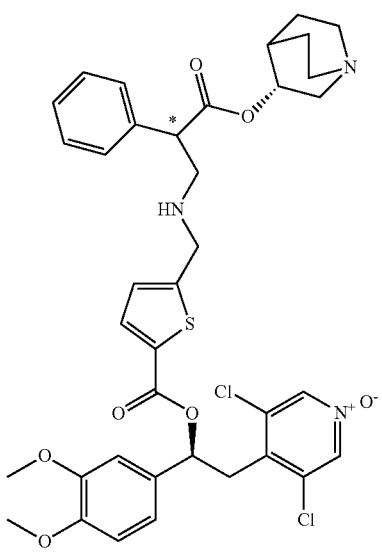

Purification of the 1:1 mixture of diastereoisomers of Example 1 by chiral preparative SFC afforded the single diastereoisomers.

Title compound (Example 20, single diastereoisomer 1) was obtained as a white solid (7.3 mg, 18%).

$^1$H NMR (400 MHz, CD$_3$CN): δ 8.09 (s, 2H), 7.58 (d, J=3.8 Hz, 1H), 7.27-7.22 (m, 5H), 6.96-6.91 (m, 2H), 6.87-6.83 (m, 2H), 6.07 (dd, J=4.5, 9.6 Hz, 1H), 4.65-4.61 (m, 1H), 3.90-3.83 (m, 2H), 3.74 (s, 3H), 3.72 (s, 3H), 3.71-3.67 (m, 1H), 3.57 (dd, J=9.9, 14.1 Hz, 1H), 3.27-3.14 (m, 2H), 2.97 (dd, J=8.0, 14.5 Hz, 1H), 2.83 (dd, J=6.1, 11.9 Hz, 1H), 2.60-2.47 (m, 4H), 2.34-2.30 (m, 1H), 2.03-2.01 (m, 1H), 1.60-1.48 (m, 3H), 1.24-1.18 (m, 2H). LCMS (Method 1): [MH+]=740 at 2.31 min. Chiral analysis (Method 6) at 7.29 min.

Title compound (Example 21, single diastereoisomer 2) was obtained as a white solid (20.74 mg, 52%).

$^1$H NMR (400 MHz, CD$_3$CN): δ 8.19 (s, 2H), 7.69 (d, J=3.8 Hz, 1H), 7.37-7.34 (m, 5H), 7.07-7.01 (m, 2H), 6.98-6.93 (m, 2H), 6.18 (dd, J=4.5, 9.6 Hz, 1H), 4.76-4.72 (m, 1H), 4.05-3.93 (m, 2H), 3.84 (s, 3H), 3.82 (s, 3H), 3.81-3.78 (m, 1H), 3.67 (dd, J=9.6, 14.1 Hz, 1H), 3.37-3.24 (m, 2H), 3.13 (dd, J=8.3, 14.4 Hz, 1H), 2.93 (dd, J=5.8, 11.9 Hz, 1H), 2.73-2.54 (m, 5H), 1.88-1.79 (m, 1H), 1.64-1.43 (m, 3H), 1.31-1.20 (m, 2H). LCMS (Method 2): [MH+]=740 at 3.65 min. Chiral analysis (Method 6) at 8.74 min.

Compounds reported in the table herebelow were made according to the analogous procedures as that described for the preparation of Example 20 and Example 21. Chiral preparative SFC or chiral preparative HPLC afforded the single diastereoisomers.

| Structure | Example Number | Precursor | Analytical Data |
|---|---|---|---|
| Single diastereoisomer [(1S)-2-(3,5-dichloro-1-oxido-pyridin-1-ium-4-yl)-1-(3,4-dimethoxyphenyl)ethyl] 5-[[[3-(2-dimethylaminoethyloxy)-3-oxo-2-phenyl-propyl]amino]methyl]thiophene-2-carboxylate | Example 22 | Example 6 | $^1$H NMR (400 MHz, CD$_3$CN): δ 8.18 (s, 2 H), 7.66 (d, J = 3.8 Hz, 1 H), 7.32-7.26 (m, 5 H), 7.04-6.98 (m, 2 H), 6.95-6.90 (m, 2 H), 6.14 (dd, J = 4.5, 9.6 Hz, 1 H), 4.21-4.08 (m, 2 H), 3.97 (d, J = 15.5 Hz, 1 H), 3.92 (d, J = 15.1 Hz, 1 H), 3.83-3.77 (m, 1 H), 3.80 (s, 3 H), 3.79 (s, 3 H), 3.65 (dd, J = 9.7, 13.7 Hz, 1 H), 3.31 (dd, J = 4.5, 13.9 Hz, 1 H), 3.21 (dd, J = 9.1, 12.1 Hz, 1 H), 2.86 (dd, J = 5.9, 12.0 Hz, 1 H), 2.48 (dd, J = 5.6, 5.6 Hz, 2 H), 2.13 (s, 6 H), NH not visible. LCMS (Method 1): [MH+] = 702 at 2.27 min. Chiral analysis (Method 6) at 4.08 min. |

| Structure | Example Number | Precursor | Analytical Data |
|---|---|---|---|
| Single diastereoisomer [(1S)-2-(3,5-dichloro-1-oxido-pyridin-1-ium-4-yl)-1-(3,4-dimethoxyphenyl)ethyl] 5-[[[3-(2-dimethylaminoethyloxy)-3-oxo-2-phenyl-propyl]amino]methyl]thiophene-2-carboxylate | Example 23 | Example 6 | $^1$H NMR (400 MHz, CD$_3$CN): δ 8.15 (s, 2 H), 7.65 (d, J = 3.8 Hz, 1 H), 7.33-7.28 (m, 5 H), 7.04-6.97 (m, 2 H), 6.95-6.89 (m, 2 H), 6.14 (dd, J = 4.7, 9.5 Hz, 1 H), 4.18-4.11 (m, 2 H), 4.02-3.90 (m, 2 H), 3.82-3.73 (m, 1 H), 3.80 (s, 3 H), 3.79 (s, 3 H), 3.63 (dd, J = 10.0, 14.3 Hz, 1 H), 3.31 (dd, J = 4.4, 13.7 Hz, 1 H), 3.22 (dd, J = 9.3, 12.3 Hz, 1 H), 2.86 (dd, J = 5.9, 12.0 Hz, 1 H), 2.44 (dd, J = 5.7, 5.7 Hz, 2 H), 2.10 (s, 6 H), NH not visible. LCMS (Method 1): [MH+] = 702 at 2.29 min. Chiral analysis (Method 6) at 4.94 min. |
| Single diastereoisomer [(1S)-2-(3,5-dichloro-1-oxido-pyridin-1-ium-4-yl)-1-(3,4-dimethoxyphenyl)ethyl] 5-[[[2-methyl-3-[(1-methyl-4-piperidyl)oxy]-3-oxo-2-phenyl-propyl]amino]methyl]thiophene-2-carboxylate | Example 24 | Example 8 | $^1$H NMR (400 MHz, CD$_3$CN): δ 8.16 (s, 2 H), 7.65 (d, J = 3.8 Hz, 1 H), 7.33-7.30 (m, 4 H), 7.30-7.22 (m, 1 H), 7.05-6.99 (m, 2 H), 6.94-6.91 (m, 2 H), 6.15 (dd, J = 4.5, 9.6 Hz, 1 H), 4.80-4.72 (m, 1 H), 3.96 (d, J = 14.7 Hz, 1 H), 3.92 (d, J = 14.9 Hz, 1 H), 3.81 (s, 3 H), 3.80 (s, 3 H), 3.65 (dd, J = 9.6, 14.1 Hz, 1 H), 3.32 (dd, J = 4.5, 14.1 Hz, 1 H), 3.19 (d, J = 11.9 Hz, 1 H), 2.94 (d, J = 11.9 Hz, 1 H), 2.36-2.31 (m, 2 H), 2.23-2.10 (m, 2 H), 2.10 (s, 3 H), 1.80-1.70 (m, 2 H), 1.58 (s, 3 H), 1.57-1.47 (m, 2 H), NH not visible. LCMS (Method 1): [MH+] = 742 at 2.33 min. Chiral analysis (Method 4) at 8.12 min. |

| Structure | Example Number | Precursor | Analytical Data |
|---|---|---|---|
| Single diastereoisomer [(1S)-2-(3,5-dichloro-1-oxido-pyridin-1-ium-4-yl)-1-(3,4-dimethoxyphenyl)ethyl] 5-[[[2-methyl-3-[(1-methyl-4-piperidyl)oxy]-3-oxo-2-phenyl-propyl]amino]methyl]thiophene-2-carboxylate | Example 25 | Example 8 | $^1$H NMR (400 MHz, CD$_3$CN): δ 8.16 (s, 2 H), 7.65 (d, J = 3.8 Hz, 1 H), 7.33-7.31 (m, 4 H), 7.27-7.22 (m, 1 H), 7.04-6.99 (m, 2 H), 6.94-6.91 (m, 2 H), 6.15 (dd, J = 4.5, 9.6 Hz, 1 H), 4.79-4.73 (m, 1 H), 3.97 (d, J = 15.7 Hz, 1 H), 3.92 (d, J = 15.4 Hz, 1 H), 3.81 (s, 3 H), 3.80 (s, 3 H), 3.64 (dd, J = 9.6, 14.1 Hz, 1 H), 3.32 (dd, J = 4.5, 13.9 Hz, 1 H), 3.18 (d, J = 11.6 Hz, 1 H), 2.95 (d, J = 11.9 Hz, 1 H), 2.37-2.28 (m, 2 H), 2.23-2.10 (m, 2 H), 2.10 (s, 3 H), 1.80-1.72 (m, 2 H), 1.57 (s, 3 H), 1.56-1.47 (m, 2 H), NH not visible. LCMS (Method 1): [MH+] = 742 at 2.31 min. Chiral analysis (Method 4) at 9.97 min. |
| Single diastereoisomer [(1S)-2-(3,5-dichloro-1-oxido-pyridin-1-ium-4-yl)-1-(3,4-dimethoxyphenyl)ethyl] 5-[[methyl-[2-methyl-3-oxo-2-phenyl-3-[(3R)-quinuclidin-3-yl]oxy-propyl]amino]methyl]thiophene-2-carboxylate | Example 26 | Example 10 | $^1$H NMR (400 MHz, CD$_3$CN): δ 8.17 (s, 2 H), 7.64 (d, J = 3.8 Hz, 1 H), 7.42-7.38 (m, 2 H), 7.36-7.31 (m, 2 H), 7.27-7.23 (m, 1 H), 7.05-6.99 (m, 2 H), 6.95-6.88 (m, 2 H), 6.16 (dd, J = 4.7, 9.7 Hz, 1 H), 4.76-4.71 (m, 1 H), 3.82 (s, 3 H), 3.80 (s, 3 H), 3.80 (d, J = 14.8 Hz, 1 H), 3.72 (d, J = 15.3 Hz, 1 H), 3.65 (dd, J = 9.8, 14.1 Hz, 1 H), 3.33 (dd, J = 4.6, 14.2 Hz, 1 H), 3.29 (d, J = 14.1 Hz, 1 H), 3.07 (ddd, J = 2.2, 8.3, 14.6 Hz, 1 H), 2.93 (d, J = 13.6 Hz, 1 H), 2.71-2.55 (m, 4 H), 2.46 (td, J = 2.3, 14.3 Hz, 1 H), 2.16 (s, 3 H), 1.91-1.87 (m, 1 H), 1.68 (s, 3 H), 1.64-1.44 (m, 3 H), 1.32-1.21 (m, 1 H). LCMS (Method 1): [MH+] = 768 at 2.62 min. Chiral analysis (Method 6) at 3.87 min. |

| Structure | Example Number | Precursor | Analytical Data |
|---|---|---|---|
| Single diastereoisomer [(1S)-2-(3,5-dichloro-1-oxido-pyridin-1-ium-4-yl)-1-(3,4-dimethoxyphenyl)ethyl] 5-[[methyl-[2-methyl-3-oxo-2-phenyl-3-[(3R)-quinuclidin-3-yl]oxy-propyl]amino]methyl]thiophene-2-carboxylate | Example 27 | Example 10 | ¹H NMR (400 MHz, CD₃CN): δ 8.17 (s, 2 H), 7.63 (d, J = 3.5 Hz, 1 H), 7.40 (d, J = 8.1 Hz, 2 H), 7.34 (dd, J = 7.7, 7.7 Hz, 2 H), 7.24 (dd, J = 7.2, 7.2 Hz, 1 H), 7.05-6.99 (m, 2 H), 6.93 (d, J = 8.3 Hz, 1 H), 6.89 (d, J = 3.8 Hz, 1 H), 6.15 (dd, J = 4.5, 9.6 Hz, 1 H), 4.76-4.72 (m, 1 H), 3.82 (s, 3 H), 3.80 (s, 3 H), 3.81 (d, J = 15.1 Hz, 1 H), 3.71 (d, J = 15.1 Hz, 1 H), 3.65 (dd, J = 9.9, 14.2 Hz, 1 H), 3.33 (dd, J = 4.5, 14.2 Hz, 1 H), 3.29 (d, J = 13.5 Hz, 1 H), 3.12 (ddd, J = 2.0, 8.2, 14.5 Hz, 1 H), 2.90 (d, J = 13.9 Hz, 1 H), 2.70-2.57 (m, 4 H), 2.49 (d, J = 14.7 Hz, 1 H), 2.16 (s, 3 H), 1.81-1.78 (m, 1 H), 1.70 (s, 3 H), 1.63-1.52 (m, 2 H), 1.51-1.42 (m, 1 H), 1.31-1.22 (m, 1 H). LCMS (Method 1): [MH+] = 768 at 2.61 min. Chiral analysis (Method 6) at 5.04 min. |
| Single diastereoisomer [(1S)-2-(3,5-dichloro-1-oxido-pyridin-1-ium-4-yl)-1-(3,4-dimethoxyphenyl)ethyl] 5-[[[3-(2-dimethylaminoethyloxy)-2-methyl-3-oxo-2-phenyl-propyl]amino]methyl]thiophene-2-carboxylate | Example 28 | Example 9 | ¹H NMR (400 MHz, CD₃CN): δ 8.15 (s, 2 H), 7.65 (d, J = 3.8 Hz, 1 H), 7.33-7.30 (m, 4 H), 7.30-7.21 (m, 1 H), 7.05-6.99 (m, 2 H), 6.94-6.91 (m, 2 H), 6.15 (dd, J = 4.5, 9.9 Hz, 1 H), 4.28-4.22 (m, 1 H), 4.10-4.03 (m, 1 H), 4.00-3.91 (m, 2 H), 3.81 (s, 3 H), 3.79 (s, 3 H), 3.65 (dd, J = 9.9, 14.1 Hz, 1 H), 3.31 (dd, J = 4.5, 14.4 Hz, 1 H), 3.23 (d, J = 11.6 Hz, 1 H), 2.88 (d, J = 11.6 Hz, 1 H), 2.41 (dd, J = 5.7, 5.7 Hz, 2 H), 2.07 (s, 6 H), 1.57 (s, 3 H), NH not visible. LCMS (Method 2): [MH+] = 716 at 3.35 min. Chiral analysis (Method 5) at 4.55 min. |

| Structure | Example Number | Precursor | Analytical Data |
|---|---|---|---|
| Single diastereoisomer [(1S)-2-(3,5-dichloro-1-oxido-pyridin-1-ium-4-yl)-1-(3,4-dimethoxyphenyl)ethyl] 5-[[[3-(2-dimethylaminoethyloxy)-2-methyl-3-oxo-2-phenyl-propyl]amino]methyl]thiophene-2-carboxylate 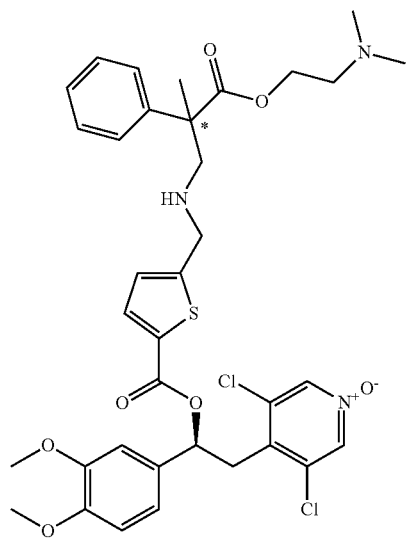 | Example 29 | Example 9 | $^1$H NMR (400 MHz, CD$_3$CN): δ 8.16 (s, 2 H), 7.66 (d, J = 3.8 Hz, 1 H), 7.33-7.30 (m, 4 H), 7.27-7.22 (m, 1 H), 7.04-6.98 (m, 2 H), 6.94-6.91 (m, 2 H), 6.15 (dd, J = 4.5, 9.9 Hz, 1 H), 4.29-4.22 (m, 1 H), 4.10-4.03 (m, 1 H), 4.00-3.92 (m, 2 H), 3.80 (s, 3 H), 3.79 (s, 3 H), 3.64 (dd, J = 9.9, 14.1 Hz, 1 H), 3.31 (dd, J = 4.9, 14.1 Hz, 1 H), 3.23 (d, J = 11.6 Hz, 1 H), 2.90 (d, J = 11.6 Hz, 1 H), 2.42 (dd, J = 5.7, 5.7 Hz, 2 H), 2.07 (s, 6 H), 1.57 (s, 3 H), NH not visible. LCMS (Method 2): [MH+] = 716 at 3.34 min. Chiral analysis (Method 5) at 5.68 min. |
| Single diastereoisomer [(1S)-2-(3,5-dichloro-1-oxido-pyridin-1-ium-4-yl)-1-(3,4-dimethoxyphenyl)ethyl] 5-[[[2-methyl-3-oxo-2-phenyl-3-[(3R)-quinuclidin-3-yl]oxy-propyl]amino]methyl]thiophene-2-carboxylate 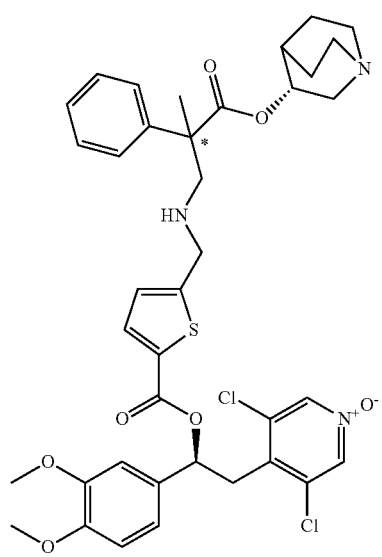 | Example 30 | Example 7 | $^1$H NMR (400 MHz, DMSO): δ 8.55 (s, 2 H), 7.65 (d, J = 3.8 Hz, 1 H), 7.34-7.27 (m, 4 H), 7.26-7.20 (m, 1 H), 7.02-6.96 (m, 4 H), 6.12 (dd, J = 4.4, 9.7 Hz, 1 H), 4.64-4.58 (m, 1 H), 3.94 (d, J = 14.6 Hz, 1 H), 3.87 (d, J = 15.2 Hz, 1 H), 3.76 (s, 3 H), 3.74 (s, 3 H), 3.57 (dd, J = 9.7, 14.0 Hz, 1 H), 3.32-3.25 (m, 1 H), 3.19-3.13 (m, 1 H), 3.00 (ddd, J = 2.0, 8.0, 14.8 Hz, 1 H), 2.92 (d, J = 10.8 Hz, 1 H), 2.61-2.43 (m, 3 H), 2.43-2.35 (m, 1 H), 2.31 (d, J = 15.2 Hz, 1 H), 1.68-1.63 (m, 1 H), 1.54 (s, 3 H), 1.45-1.27 (m, 3 H), 1.12-1.03 (m, 1 H), NH not visible. LCMS (Method 1): [MH+] = 754 at 2.36 min. Chiral analysis (Method 9) at 6.34 min. |

| Structure | Example Number | Precursor | Analytical Data |
|---|---|---|---|
| Single diastereoisomer [(1S)-2-(3,5-dichloro-1-oxido-pyridin-1-ium-4-yl)-1-(3,4-dimethoxyphenyl)ethyl] 5-[[[2-methyl-3-oxo-2-phenyl-3-[(3R)-quinuclidin-3-yl]oxy-propyl]amino]methyl]thiophene-2-carboxylate | Example 31 | Example 7 | $^1$H NMR (400 MHz, DMSO): δ 8.55 (s, 2 H), 7.67 (d, J = 3.8 Hz, 1 H), 7.33-7.28 (m, 4 H), 7.26-7.21 (m, 1 H), 7.02-6.98 (m, 2 H), 6.98-6.94 (m, 2 H), 6.13 (dd, J = 4.4, 9.7 Hz, 1 H), 4.70-4.65 (m, 1 H), 3.97 (d, J = 15.2 Hz, 1 H), 3.89 (d, J = 13.9 Hz, 1 H), 3.76 (s, 3 H), 3.75 (s, 3 H), 3.57 (dd, J = 9.9, 14.1 Hz, 1 H), 3.30 (dd, J = 4.3, 14.0 Hz, 1 H), 3.20 (d, J = 11.4 Hz, 1 H), 3.04 (ddt, J = 1.8, 7.6, 7.2 Hz, 1 H), 2.94 (d, J = 12.1 Hz, 1 H), 2.65-2.54 (m, 3 H), 2.53-2.45 (m, 1 H), 2.43 (d, J = 14.3 Hz, 1 H), 1.85-1.78 (m, 1 H), 1.54-1.52 (m, 1 H), 1.53 (s, 3 H), 1.49-1.34 (m, 2 H), 1.23-1.13 (m, 1 H), NH not visible. LCMS (Method 1): [MH+] = 754 at 2.33 min. Chiral analysis (Method 9) at 8.96 min. |

Intermediate 22. (1-methyl-4-piperidyl) 3-oxo-1-phenyl-cyclobutanecarboxylate A mixture of 3-oxo-1-phenyl-cyclobutanecarboxylic acid (350 mg, 1.84 mmol), N,N'-dicyclohexylcarbodiimide (760 mg, 3.67 mmol) and 1-hydroxybenzotriazole (500 mg, 3.67 mmol) in dry THF (10 mL) was stirred at room temperature. After one hour, 1-methylpiperidin-4-ol (420 mg, 3.67 mmol) was added and the mixture was stirred at room temperature for 18 hours. After this time the reaction mixture was filtered through a Celite® cartridge, washed through with THF and the filtrate was concentrated in vacuo. The residue was taken up with EtOAc (20 mL) and washed with saturated aqueous NaHCO$_3$ (2×30 mL) and brine (30 mL). The organic phase was filtered through a phase separator and the solvent was removed in vacuo to give the title compound as a brown gum.

LCMS (Method 1): [MH+]=288 at 2.24 min.

The following intermediate was synthesized via a similar method to Intermediate 22:

| Structure | Intermediate number | Analytical Data |
|---|---|---|
| 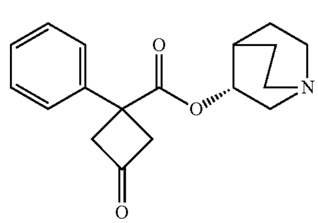 [SMILES: O=C1CC(C(=O)O[C@H]2CN3CCC2CC3)(c2ccccc2)C1] | Intermediate 23 | LCMS (Method 1): [MH+] = 300 at 2.27 min. |

Intermediate 24. 5-[(tert-butoxycarbonylamino)methyl]thiophene-2-carboxylic acid

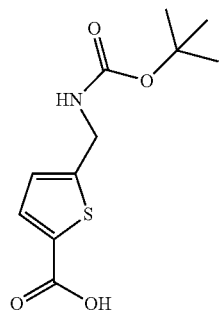 [SMILES: CC(C)(C)OC(=O)NCc1ccc(C(=O)O)s1]

To a stirred mixture of 5-(aminomethyl)thiophene-2-carboxylic acid (0.5 g, 3.18 mmol) and di-tert-butyl dicarbonate (0.83 g, 3.82 mmol) in dioxane (5 mL) and water (1 mL) was added NaHCO$_3$ (0.53 g, 6.37 mmol) and the resulting mixture was stirred at room temperature for 72 hours. The solvent was removed by evaporation and the residue was partitioned between EtOAc (25 mL) and 0.2 N HCl (2×10 mL). The aqueous extracts were combined and back-extracted with EtOAc (20 mL), the organic extracts were combined and filtered through a phase separator and the solvent was removed in vacuo to give the title compound as a white solid (0.85 g, quantitative).
LCMS (Method 10): [MH+]=256 at 2.30 min.

Intermediate 25. [(1S)-2-(3,5-dichloro-1-oxido-pyridin-1-ium-4-yl)-1-(3,4-dimethoxyphenyl)ethyl] 5-[(tert-butoxycarbonylamino)methyl]thiophene-2-carboxylate

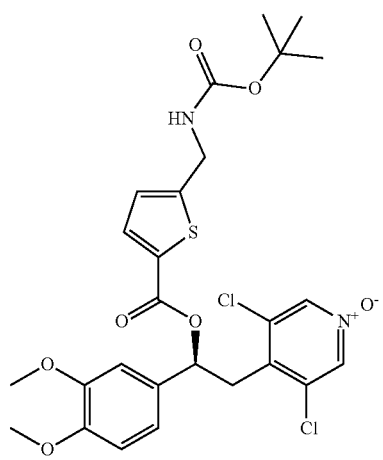

A mixture of 5-[(tert-butoxycarbonylamino)methyl]thiophene-2-carboxylic acid (0.8 g, 3.11 mmol, (1S)-2-(3,5-dichloro-1-oxido-pyridin-1-ium-4-yl)-1-(3,4-dimethoxyphenyl)-ethanol (0.94 g, 3.11 mmol), (compound I-1/A described in the co-pending international application n. PCT/EP2013/075520), 4-(dimethylamino)pyridine (0.19 mg, 1.56 mmol) and N-(3-dimethylaminopropyl)-N'-ethyl-carbodiimide hydrochloride (1.2 g, 6.22 mmol)) in dichloromethane (20 mL) was stirred at room temperature for 18 hours. The reaction mixture was washed with water (2×25 mL), the organic phase was isolated by filtering through a phase separator and the solvent was removed in vacuo. The crude material was purified by silica gel column chromatography, eluting with 40-100% EtOAc in iso-hexane, to afford the title compound (1.35 g, 75%) as a white solid.
LCMS (Method 10): [MH+]=583 at 3.24 min.

Intermediate 26. [(1S)-2-(3,5-dichloro-1-oxido-pyridin-1-ium-4-yl)-1-(3,4-dimethoxyphenyl)ethyl] 5-(aminomethyl)thiophene-2-carboxylate

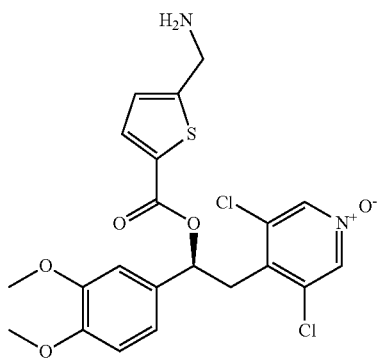

To a solution of [(1S)-2-(3,5-dichloro-1-oxido-pyridin-1-ium-4-yl)-1-(3,4-dimethoxyphenyl)ethyl] 5-[(tert-butoxycarbonylamino)methyl]thiophene-2-carboxylate (0.31 g, 0.53 mmol) in DCM (5 mL) at 0° C. was added a 4N solution of HCl in dioxane (0.4 mL, 1.6 mmol) and the resulting mixture was stirred at 0° C. for 4 hours then left standing in the cold overnight. The mixture was diluted with DCM (10 mL) and washed with saturated NaHCO$_3$ aqueous solution (20 mL), the organic phase was filtered through a phase separator and the solvent was removed in vacuo to give the title compound as a pale yellow gum (0.3 g, quantitative).
LCMS (Method 3): [MH+]=483 at 2.46 min

Example 32. [(1S)-2-(3 dimethoxyphenyl)ethyl] 5-[[[3-[(1-methyl-4-piperidyl)oxycarbonyl]-3-phenyl-cyclobutyl]amino]methyl]-thiophene-2-carboxylate

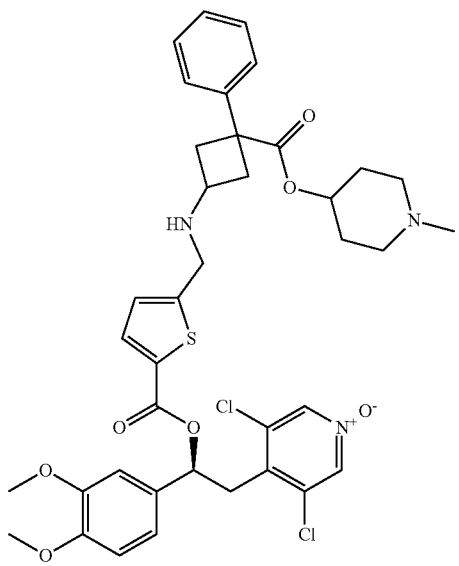

To a stirred mixture of [(1S)-2-(3,5-dichloro-1-oxido-pyridin-1-ium-4-yl)-1-(3,4-dimethoxyphenyl)ethyl] 5-(aminomethyl)thiophene-2-carboxylate (0.3 g, 0.62 mmol) and (1-methyl-4-piperidyl)-3-oxo-1-phenylcyclobutanecarboxylate (0.18 g, 0.62 mmol) in trifluoroethanol (5 mL) at room temperature was added AcOH (35 µL, 0.62 mmol) and the resulting mixture was stirred at room temperature for 72 hours. The solvent was removed in vacuo and the residue was azeotroped with toluene (3×5 mL). The residue was taken up into dry DCM (5 mL) and NaBH(OAc)$_3$ (0.46 g, 2.17 mmol) was added and the mixture was stirred at room temperature for 18 hours. The mixture was diluted with DCM (15 mL) and washed with saturated NaHCO$_3$ aqueous solution (2×20 mL). The organic phase was filtered through a phase separator and the solvent was removed in vacuo. The crude residue was purified by preparative HPLC to give the title compound as a beige solid (74 mg, 16%).

$^1$H NMR (400 MHz, CD$_3$CN): δ 8.10$^{†or*}$ (s, 2H), 8.18$^{†or*}$ (s, 2H), 7.70$^{†or*}$ (d, J=3.6 Hz, 1H), 7.68$^{†or*}$ (d, J=3.8 Hz, 1H), 7.44-7.33 (m, 3H), 7.28-7.24 (m, 2H), 7.08-7.01 (m, 2H), 6.99-6.93 (m, 2H), 6.18 (dd, J=5.0, 9.5 Hz, 1H), 4.74-4.66 (m, 1H), 3.92 (d, J=5.1 Hz, 2H), 3.84$^{†or*}$ (s, 3H), 3.83$^{†or*}$ (s, 3H), 3.82 (s, 3H), 3.71-3.63 (m, 1H), 3.46-3.39* (m, 1H), 3.34 (dd, J=4.3, 14.3 Hz, 1H), 3.20-3.16$^†$ (m, 1H), 3.14-3.06* (m, 2H), 2.79-2.72$^†$ (m, 2H), 2.58-2.50$^†$ (m, 2H), 2.39-2.30$^†$ (m, 2H), 2.30-2.18* (m, 6H), 2.30-2.15$^†$ (m, 2H), (s, 3H), 2.12$^{†or*}$ (s, 3H), 1.76-1.69 (m, 2H), 1.59-1.49 (m, 2H). † and * refer to different isomers (arbitrarily assigned), NH not seen.

LCMS (Method 3): [MH+]=754 at 2.45 min.

The following compound was synthesized following the same procedure.

Example 34 and Example 35

Single diastereomers of [(1S)-2-(3,5-dichloro-1-oxido-pyridin-1-ium-4-yl)-1-(3,4-dimethoxyphenyl)ethyl] 5-[[[3-[(1-methyl-4-piperidyl)oxycarbonyl]-3-phenyl-cyclobutyl]amino]methyl]thiophene-2-carboxylate (diastereoisomers 1 and 2)

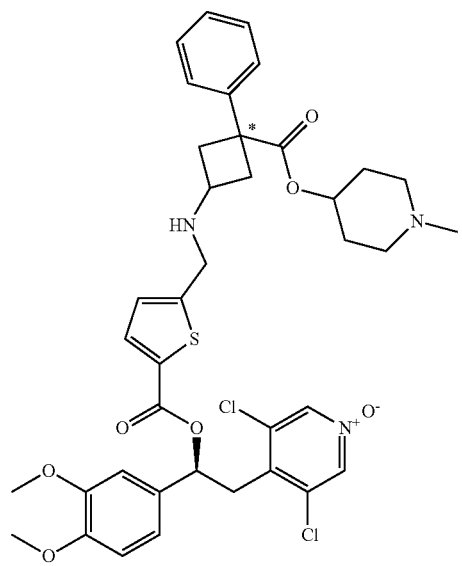

| Structure | Example Number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[3-phenyl-3-[(3R)-quinuclidin-3-yl]oxycarbonyl-cyclobutyl]amino]methyl]thiophene-2-carboxylate | Example 33 | Intermediate 23 and Intermediate 26 | $^1$H NMR (400 MHz, CD3CN): δ 8.20† (s, 2 H), 8.19* (s, 2 H), 7.70† (d, J = 3.3 Hz, 1 H), 7.69* (d, J = 3.1 Hz, 1 H), 7.45-7.27 (m, 5 H), 7.08-7.02 (m, 2 H), 7.00-6.94 (m, 2 H), 6.22-6.16 (m, 1 H), 4.69-4.64 (m, 1 H), 3.94† (s, 2 H), 3.92* (s, 2 H), 3.85$^{†or*}$ (s, 3 H), 3.84$^{†or*}$ (s, 3 H), 3.83$^{†or*}$ (s, 3 H), 3.82$^{†or*}$ (s, 3 H), 3.72-3.64 (m, 1 H), 3.48-3.40† (m, 1 H), 3.35 (dd, J = 3.7, 14.0 Hz, 1 H), 3.21-3.17* (m, 1 H), 3.15-3.10† (m, 2 H), 3.08-3.03 (m, 1 H), 2.82-2.76* (m, 2 H), 2.68-2.51 (m, 4 H), 2.42-2.35 (m, 1 H), 2.23-2.20† (m, 2 H), 1.84-1.79 (m, 1 H), 1.64-1.54 (m, 1 H), 1.50-1.42 (m, 2 H), 1.26-1.18 (m, 1 H), † and * refer to different isomers (arbitrarily assigned), NH not observed. LCMS (Method 3): [MH+] = 766 at 2.44 min. |

Purification of the 1:1 mixture of diastereoisomers of Example 32 by chiral preparative HPLC afforded the single diastereoisomers.

Title compound (Example 34, single diastereoisomer 1) was obtained as an off-white solid (31.4 mg, 13%).

¹H NMR (400 MHz, CD₃CN): δ 8.19 (s, 2H), 7.70 (dd, J=3.0, 3.0 Hz, 1H), 7.39-7.33 (m, 2H), 7.28-7.23 (m, 3H), 7.08-7.02 (m, 2H), 7.00-6.94 (m, 2H), 6.19 (dd, J=4.5, 9.6 Hz, 1H), 4.74-4.69 (m, 1H), 3.93 (s, 2H), 3.84 (s, 3H), 3.83 (s, 3H), 3.68 (dd, J=9.7, 14.0 Hz, 1H), 3.47-3.38 (m, 1H), 3.35 (dd, J=3.7, 14.3 Hz, 1H), 3.14-3.06 (m, 2H), 2.32-2.18 (m, 6H), 2.11 (s, 3H), 1.77-1.68 (m, 2H), 1.59-1.50 (m, 2H). NH not seen. LCMS (Method 3): [MH+]=754 at 2.42 min.

Chiral analysis (Method 12) at 14.33 min.

Title compound (Example 35, single diastereoisomer 2) was obtained as an off-white solid (17 mg, 7%).

¹H NMR (400 MHz, CD₃CN): δ 8.18 (s, 2H), 7.67 (d, J=3.8 Hz, 1H), 7.44-7.34 (m, 4H), 7.30-7.25 (m, 1H), 7.06-7.00 (m, 2H), 6.97-6.93 (m, 2H), 6.17 (dd, J=4.5, 9.6 Hz, 1H), 4.71-4.63 (m, 1H), 3.91 (s, 2H), 3.83 (s, 3H), 3.82 (s, 3H), 3.66 (dd, J=9.6, 14.1 Hz, 1H), 3.34 (dd, J=4.5, 14.1 Hz, 1H), 3.21-3.12 (m, 1H), 2.79-2.71 (m, 2H), 2.57-2.50 (m, 2H), 2.38-2.34 (m, 2H), 2.21-2.18 (m, 2H), 2.13 (s, 3H), 1.77-1.68 (m, 2H), 1.58-1.48 (m, 2H). NH not seen. LCMS (Method 3): [MH+]=754 at 2.45 min.

Chiral analysis (Method 12) at 18.42 min.

Compounds reported in the table herebelow were made according to the analogous procedures as that described for the preparation of Example 34 and Example 35. Chiral preparative SFC or chiral preparative HPLC afforded the single diastereoisomers.

| Structure | Example Number | Precursor | Analytical Data |
|---|---|---|---|
| Single diastereoisomer [(1S)-2-(3,5-dichloro-1-oxido-pyridin-1-ium-4-yl)-1-(3,4-dimethoxyphenyl)ethyl] 5-[[[3-phenyl-3-[(3R)-quinuclidin-3-yl]oxy-carbonyl-cyclobutyl]amino]methyl]thiophene-2-carboxylate | Example 36 | Example 33 | ¹H NMR (400 MHz, CD₃CN): δ 8.20 (s, 2 H), 7.70 (d, J = 4.4 Hz, 1 H), 7.39-7.33 (m, 2 H), 7.29-7.25 (m, 3 H), 7.08-7.03 (m, 2 H), 7.00-6.94 (m, 2 H), 6.20 (ddd, J = 4.6, 4.6, 4.6 Hz, 1 H), 4.70-4.65 (m, 1 H), 3.94 (s, 2 H), 3.85 (s, 3 H), 3.83 (s, 3 H), 3.69 (dd, J = 9.5, 16.1 Hz, 1 H), 3.48-3.40 (m, 1H), 3.35 (dd, J = 4.0, 15.0 Hz, 1 H), 3.15-3.02 (m, 3 H), 2.68-2.59 (m, 3 H), 2.54-2.49 (m, 1 H), 2.42-2.35 (m, 1 H), 2.25-2.20 (m, 2 H), 1.84-1.79 (m, 1 H), 1.63-1.55 (m, 1 H), 1.50-1.45 (m, 2 H), 1.25-1.17 (m, 1 H). NH not observed. LCMS (Method 3): [MH+] = 766 at 2.46 min. Chiral analysis (Method 11) at 9.38 min. |

-continued

| Structure | Example Number | Precursor | Analytical Data |
|---|---|---|---|
| Single diastereoisomer [(1S)-2-(3,5-dichloro-1-oxido-pyridin-1-ium-4-yl)-1-(3,4-dimethoxyphenyl)ethyl] 5-[[[3-phenyl-3-[(3R)-quinuclidin-3-yl]oxy-carbonyl-cyclobutyl]amino]methyl]thiophene-2-carboxylate | Example 37 | Example 33 | $^1$H NMR (400 MHz, CD$_3$CN): δ 8.19 (s, 2 H), 7.69 (d, J = 3.8 Hz, 1 H), 7.45-7.36 (m, 4 H), 7.32-7.27 (m, 1 H), 7.07-7.02 (m, 2 H), 6.98-6.94 (m, 2 H), 6.19 (dd, J = 4.5, 9.7 Hz, 1 H), 4.68-4.64 (m, 1 H), 3.92 (s, 2 H), 3.84 (s, 3 H), 3.83 (s, 3 H), 3.67 (dd, J = 9.6, 14.1 Hz, 1 H), 3.35 (dd, J = 4.6, 14.1 Hz, 1 H), 3.23-3.15 (m, 1 H), 3.05 (ddd, J = 2.3, 8.2, 14.6 Hz, 1 H), 2.82-2.75 (m, 2 H), 2.71-2.54 (m, 6 H), 2.42-2.38 (m, 1 H), 1.84-1.79 (m, 1 H), 1.64-1.42 (m, 3 H), 1.32-1.21 (m, 2 H). LCMS (Method 3): [MH+] = 766 at 2.48 min. Chiral analysis (Method 11) at 12.17 min. |

Pharmacological Activity of the Compounds of the Invention.

In Vitro Determination of PDE4 Inhibitory Activity.

In vitro determination of PDE4 inhibitory activity for compounds of the invention may be determined according to one of the protocols reported below.

PDE4B2 HTRF assay:

PDE4B2 activity is detected using the LANCE Ultra cAMP homogeneous time resolved fluorescence resonance energy transfer (TR-FRET) assay from Perkin Elmer. The assay is based on the competition between the europium (Eu) chelate-labeled cAMP tracer and sample cAMP for binding sites on cAMP-specific monoclonal antibodies (mAb) labelled with the ULight™ dye. The assay is carried out in 384-well low volume plates in a volume of 10 μl. Human recombinant PDE4B2 (80 pM) is incubated for 2 h with 3 nM cAMP in buffer containing 1×HBSS, 5 mM HEPES, 3 mM MgCl$_2$, 0.1% BSA, pH 7.4 with or without test compounds. The enzymatic reactions are efficiently stopped by the addition of 500 μM IBMX present in the combined Stop/Detection buffer containing europium (Eu) chelate-labeled cAMP tracer and cAMP-specific monoclonal antibodies (mAb) labelled with the ULight™ dye. Samples are then further incubated for 1 h before plates are read at ex 340 nm and em at 665 nm and 615 nm on an EnVision reader. IC$_{50}$ values are determined from competition curves using a non-linear curve fitting program.

PDE4 Cell Free Assay Protocol:

PDE4 activity is determined in U937 human monocytic supernatants cells lysate. Cells are cultured, harvested and supernatant fraction prepared essentially as described in Torphy T J et al J. Pharmacol. Exp. Ther. 1992; 263:1195-1205, which is incorporated herein by reference in its entirety. U937 cells are grown at 37° C., 5% CO$_2$ in RPMI 1640 with GlutaMAX™-I medium supplemented with 10% fetal bovine serum and 100 μg/mL Pen-strep (Gibco). Cells are harvested and washed twice by centrifugation (150×g, 8 min) in cold PBS. Washed cells are re-suspended in cold Krebs-Ringer-Henseleit buffer at a final concentration 20×10$^6$ cells/mL and sonicated. After centrifugation at 15000×g for 20 min, the supernatants are pooled, divided in aliquots and stored at −80° C.

PDE4 activity is determined in cells supernatants by assaying cAMP disappearance from the incubation mixtures. The concentration of the test compounds ranges between 10$^{-12}$ M and 10$^{-6}$ M. Reactions are stopped by enzyme heat inactivation (2.5 minutes at 100° C.) and residual cAMP content is determined using the 'LANCE cAMP Assay' from PerkinElmer following the provider instructions.

The results, expressed as mean±standard deviation of the molar concentration of the test compound producing 50% inhibition of cAMP disappearance (IC$_{50}$). Percentage of inhibition of PDE4 activity is calculated, assuming cAMP disappearance in the absence of inhibitors as 100% and cAMP disappearance in heat inactivated samples as 0%.

Compounds of the invention, when tested in one of the above reported protocols, displayed an IC$_{50}$ lower than 100 nM.

In Vitro Determination of M3 Antagonism

In vitro determination of M3 antagonism for compounds of the invention may be determined according to one of the protocols reported below.

M3 Receptor Radioligand Binding Assay:

Human $M_3$ receptor membranes (15 μg/well) from Perkin Elmer are incubated with 0.52 nM Scopolamine Methyl Chloride, [N-methyl-3H] with or without test compounds, or a saturating concentration of Atropine (5 μM) for the determination of non-specific binding. The assay is carried out in 96-well polypropylene plates in a volume of 250 μl. The assay buffer used is 50 mM Tris-HCl, 154 mM NaCl (pH 7.4). The final assay concentration of DMSO is 0.5% (v/v). The plates are sealed and incubated for 2 h at room temperature on an orbital shaker (slow speed). Membranes are harvested onto 96-well unifilter GF/C filter plates pre-treated with 0.5% polyethyleneimine (v/v), using a filter manifold, washed four times with 2000 of assay buffer. The plates are dried before addition of 50 μl of microscint-0, sealed then read in a Trilux Microbeta scintillation counter. $IC_{50}$ values are determined from competition curves using a non-linear curve fitting program. $K_i$ values are calculated from $IC_{50}$ values by the Cheng and Prusoff equation.

M3 Binding Assay:

CHO-K1 clone cells expressing the human M3-receptor (Swissprot P20309) were harvested in $Ca^{++}/Mg^{++}$ free phosphate-buffered saline and collected by centrifugation at 1500 rpm for 3 min. The pellets were resuspended in ice cold buffer A (15 mM Tris-HCl pH 7.4, 2 mM $MgCl_2$, 0.3 mM EDTA, 1 mM EGTA) and homogenized by a PBI politron (setting 5 for 15 s). The crude membrane fraction was collected by two consecutive centrifugation steps at 40000 g for 20 min at 4° C., separated by a washing step in buffer A. The pellets obtained were finally resuspended in buffer B (75 mM Tris HCl pH 7.4, 12.5 mM $MgCl_2$, 0.3 mM EDTA, 1 mM EGTA, 250 mM sucrose), and aliquots were stored at −80° C.

The day of experiment, frozen membranes were resuspended in buffer C (50 mM Tris-HCl pH 7.4, 2.5 mM $MgCl_2$, 1 mM EDTA). The non-selective muscarinic radioligand [$^3$H]-N-methyl scopolamine (*Mol. Pharmacol.* 45:899-907, which is incorporated herein by reference in its entirety) was used to label the M3 binding sites. Binding experiments were performed in duplicate (ten point concentrations curves) in 96 well plates at radioligand concentration of 0.1-0.3 nM. The non-specific binding was determined in the presence of cold N-methyl scopolamine 10 μM. Samples (final volume 0.75 mL) were incubated at room temperature for 90 min. The reaction was terminated by rapid filtration through GF/B Unifilter plates and two washes (0.75 mL) with cold buffer C using a Packard Filtermate Harvester. Radioactivity on the filters was measured by a microplate scintillation counter TriCarb 2500 (PerkinElmer).

The compounds of the invention, when tested in one of the above reported protocols, displayed an $IC_{50}$ lower than 100 nM. The compounds of the invention, displayed an $IC_{50}$ lower than 100 nM, preferred even less than 10 nM or even less than 1 nM, in both PDE4 cell free and M3 binding assays.

In the following table $IC_{50}$ data are reported for the compounds tested in the above methods, classified according to the following ranges:

+: M3 IC50 in the range 10-100 nM
++: M3 IC50 in the range 1-10 nM
+++: M3 IC50<=1 nM
+: PDE4B2 IC50 in the range 10-100 nM
++: PDE4B2 IC50 in the range 1-10 nM
+++: PDE4B2 IC50<=1 nM

| Ex. N | M3 IC50 Activity* | PDE4B2 IC50 Activity** |
|---|---|---|
| 1 | ++ | ++ |
| 2 | ++ | ++ |
| 3 | ++ | ++ |
| 4 | + | ++ |
| 5 | ++ | +++ |
| 7 | +++ | ++ |
| 8 | + | +++ |
| 9 | + | +++ |
| 10 | ++ | ++ |
| 11 | + | ++ |
| 12 | ++ | ++ |
| 14 | ++ | ++ |
| 15 | +++ | ++ |
| 16 | ++ | ++ |
| 17 | ++ | +++ |
| 18 | +++ | ++ |
| 19 | ++ | ++ |
| 20 | +++ | ++ |
| 21 | ++ | ++ |
| 22 | ++ | ++ |
| 24 | + | +++ |
| 25 | + | ++ |
| 26 | ++ | ++ |
| 27 | +++ | ++ |
| 28 | + | +++ |
| 29 | + | ++ |
| 30 | ++ | +++ |
| 31 | + | ++ |
| 32 | + | +++ |
| 33 | ++ | ++ |
| 34 | + | ++ |
| 35 | ++ | ++ |
| 36 | +++ | ++ |
| 37 | ++ | ++ |

*M3 Receptor radioligand binding assay
**PDE4B2 HTRF assay

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

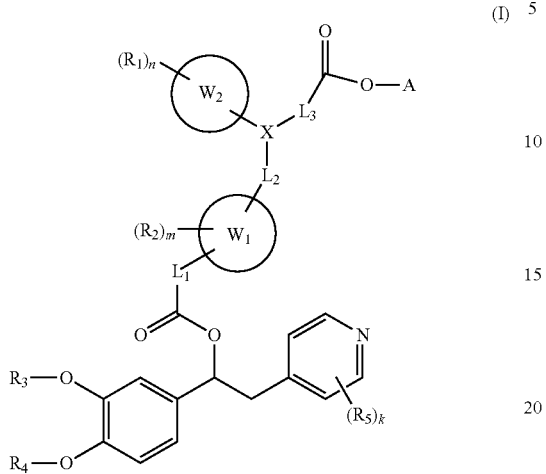

wherein:
  each $R_1$ is hydrogen halogen, $(C_1-C_4)$ alkyl, $(C_1-C_4)$ alkoxy, $(C_1-C_4)$ haloalkyl, hydroxy, $-SO_2NR_6R_7$, $-CN$, $-NR_8SO_2R_9$, $-NR_6R_7$, $-CONR_6R_7$, or $-NR_8COR_9$, wherein said $(C_1-C_4)$ alkyl is optionally substituted by one or more groups selected from the group consisting of $(C_3-C_7)$ cycloalkyl, hydroxyl, and $-NR_6R_7$ and wherein said $(C_1-C_4)$ alkoxy is optionally substituted by one or more halogens or $(C_3-C_7)$ cycloalkyl groups, wherein
    $R_6$ is hydrogen or $(C_1-C_6)$ alkyl;
    $R_7$ is hydrogen or $(C_1-C_6)$ alkyl;
    $R_8$ is hydrogen or $(C_1-C_6)$ alkyl;
    $R_9$ is hydrogen or $(C_1-C_6)$ alkyl;
  n is an integer of 1 to 3;
  each $R_2$ is hydrogen halogen, $(C_1-C_4)$ alkyl, $(C_1-C_4)$ alkoxy, $(C_1-C_4)$haloalkyl, hydroxy, $-SO_2NR_{10}R_{11}$, $-CN$, or $-NR_{12}SO_2R_{13}$, wherein said $(C_1-C_4)$ alkyl and said $(C_1-C_4)$ alkoxy are optionally substituted by one or more $(C_3-C_7)$ cycloalkyl groups, wherein
    $R_{10}$ is hydrogen or $(C_1-C_6)$ alkyl;
    $R_{11}$ is hydrogen or $(C_1-C_6)$ alkyl;
    $R_{12}$ is hydrogen or $(C_1-C_6)$ alkyl;
    $R_{13}$ is hydrogen or $(C_1-C_6)$ alkyl;
  m is an integer of 1 to 3;
  $R_3$ and $R_4$ are different or the same and are independently:
    H;
    $(C_3-C_7)$ cycloalkylcarbonyl;
    $(C_1-C_6)$ alkyl, optionally substituted by one or more substituents selected from the group consisting of $(C_1-C_4$ alkoxy), $(C_3-C_7)$ cycloalkyl, and $(C_5-C_7)$ cycloalkenyl;
    $(C_1-C_6)$ haloalkyl;
    $(C_3-C_7)$ cycloalkyl;
    $(C_5-C_7)$ cycloalkenyl;
    $(C_2-C_6)$ alkenyl; or
    $(C_2-C_6)$ alkynyl;
  each $R_5$, whenever present, is independently CN, $NO_2$, $CF_3$, or a halogen atom;
  k is 0 or an integer of 1 to 3;
  $L_1$ is a bond $W_1$ is a heteroarylene group;
$W_2$ is aryl or heteroaryl;
$L_2$ is a group $-(CH_2)_q-$ wherein q is an integer of 1 to 4;
$L_3$ is a bond or a group $-(CH_2)_s-$ wherein s is 1 or 2;
X is:

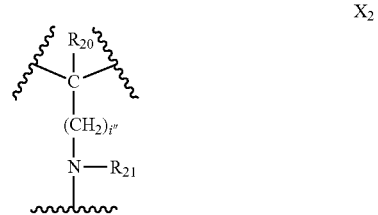

wherein
  $R_{20}$ is H, OH, or $(C_1-C_4)$ alkyl optionally substituted by one or more hydroxyl group;
  $R_{21}$ is hydrogen or $(C_1-C_6)$ alkyl optionally substituted by hydroxyl;
  i is 1 or 2;
  i' is 1 or 2;
  i" is an integer of 1 to 4;
  A is:
    a group $(CH_2)_s-NR_{16}R_{17}$ wherein s is an integer of 1 to 4 and $R_{16}$ and $R_{17}$ are independently hydrogen or $(C_1-C_4)$ alkyl; or
    a saturated monocyclic, bicyclic, or tricyclic heterocyclic ring system containing one N heteroatom or $NR_{18}$ wherein $R_{18}$ is $(C_1-C_4)$ alkyl or benzyl;
  an N-oxide on the pyridine ring, a deuterated derivative, or a pharmaceutically acceptable salt thereof.

2. The compound, N-oxide, deuterated derivative, or pharmaceutically acceptable salt according to claim 1, which has formula (I)':

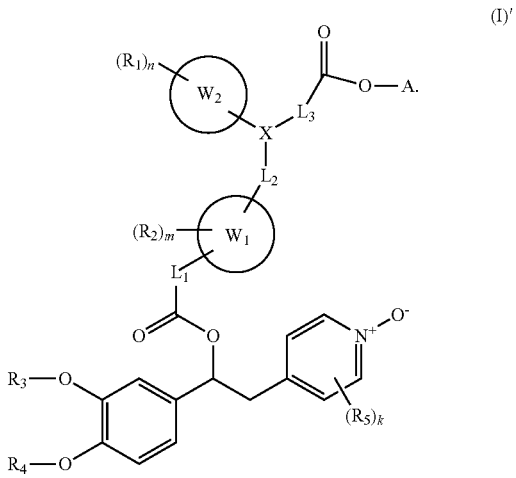

3. The compound, N-oxide, deuterated derivative, or pharmaceutically acceptable salt according to claim 1, wherein A is a group of formula (i), (ii), (iii), or (iv):

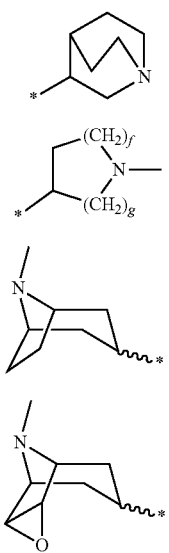

(i)

(ii)

(iii)

(iv)

wherein
f=1, 2 or 3; and
g=1, 2 or 3.

4. The compound, N-oxide, deuterated derivative, or pharmaceutically acceptable salt according to claim 1, wherein $L_3$ is a bond, X is a group $X_2$, and i" is 1, having formula (IA):

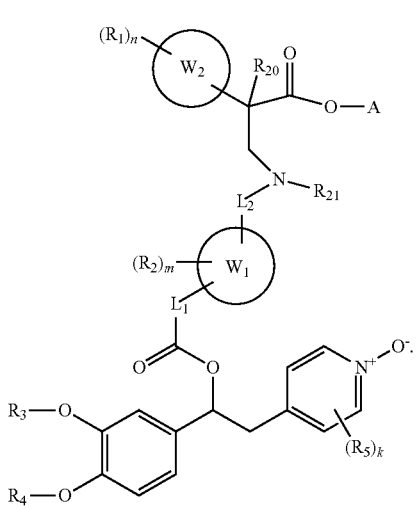

(IA)

5. The compound, N-oxide, deuterated derivative, or pharmaceutically acceptable salt according to claim 4, wherein k is 2 and each $R_5$ is a halogen atom.

6. The compound, N-oxide, deuterated derivative, or pharmaceutically acceptable salt according to claim 5, wherein $R_5$ are two chlorine atoms at positions 3 and 5 of the pyridine ring.

7. The compound, N-oxide, deuterated derivative, or pharmaceutically acceptable salt according to claim 4, wherein $R_4$ is a ($C_1$-$C_6$) alkyl and $R_3$ is ($C_3$-$C_7$) cycloalkyl or ($C_1$-$C_6$) alkyl which is optionally substituted by ($C_3$-$C_7$) cycloalkyl.

8. The compound, N-oxide, deuterated derivative, or pharmaceutically acceptable salt according to claim 1 of formula (IC):

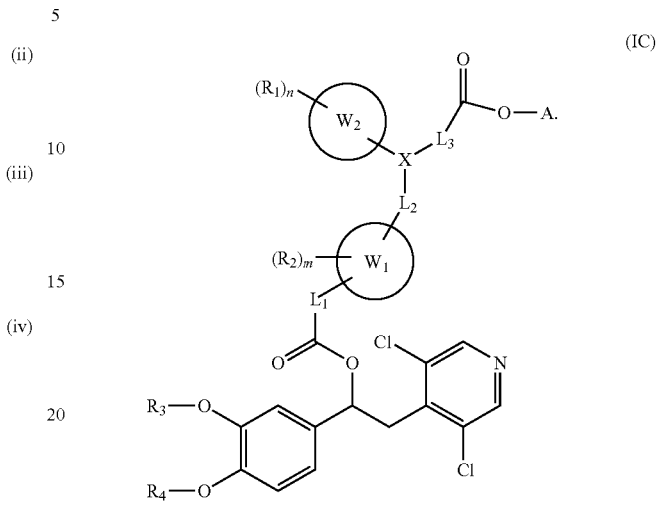

(IC)

9. The compound, N-oxide, deuterated derivative, or pharmaceutically acceptable salt according to claim 8 of formula (ID):

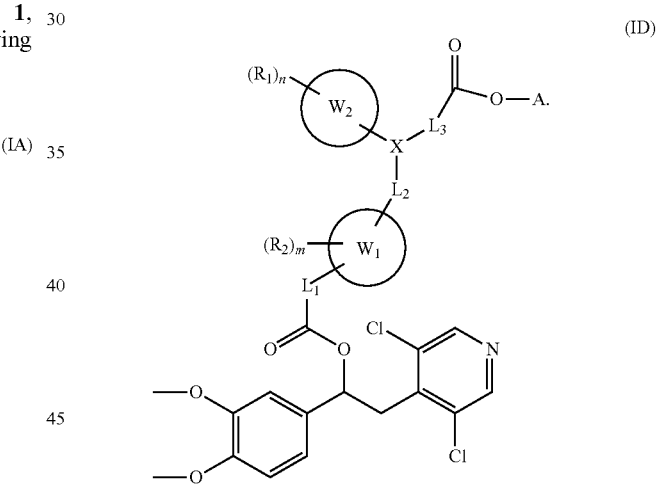

(ID)

10. The compound, N-oxide, deuterated derivative, or pharmaceutically acceptable salt according to claim 9, wherein:
both $L_1$ and $L_3$ are a bond;
m is 0;
$W_1$ is thienylene-2,5-diyl;
n is 0;
$W_2$ is phenyl;
X is a group of formula $X_2$ wherein i" is 1, and $R_{20}$ and $R_{21}$ are each independently H or methyl;
A is a group of formula (i) or (ii):

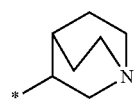

(i)

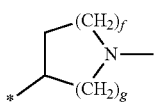

wherein f is 1 and g is 1 or f is 1 and g is 2 and the asterisk (*) represents the point of attachment to the oxygen atom of Formula (I); or A is the group —CH$_2$CH$_2$N (CH$_3$).

11. The compound, N-oxide, deuterated derivative, or pharmaceutically acceptable salt according to claim 1, represented by formula (I)" wherein the absolute configuration of carbon (1) is that shown below:

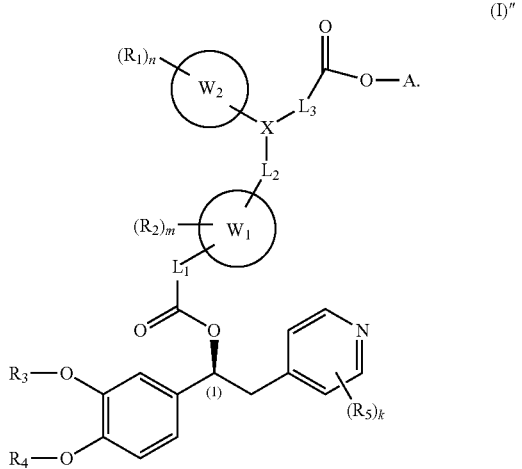

12. The compound, N-oxide, deuterated derivative, or pharmaceutically acceptable salt according to claim 1 which is selected from the group consisting of:

[(1S)-2-(3,5-dichloro-1-oxido-pyridin-1-ium-4-yl)-1-(3,4-dimethoxyphenyl)ethyl] 5-[[[3-oxo-2-phenyl-3-[(3R)-quinuclidin-3-yl] oxy-propyl]amino] methyl]thiophene-2-carboxylate;

[(1S)-2-(3,5-dichloro-1-oxido-pyridin-1-ium-4-yl)-1-(3,4-dimethoxyphenyl)ethyl]-5-[[[3-[(3R)-1-methylpyrrolidin-3-yl]oxy-3-oxo-2-phenyl-propyl]amino]methyl]thiophene-2-carboxylate;

[(1S)-2-(3,5-dichloro-1-oxido-pyri di n-1-ium-4-yl)-1-(3,4-dimethoxyphenyl)ethyl] 5-[[[3-[(1-methyl-4-piperidyl)oxy]-3-oxo-2-phenyl-propyl]amino] methyl]thiophene-2-carboxylate;

[(1S)-2-(3,5-dichloro-1-oxido-pyridin-1-ium-4-yl)-1-(3,4-dimethoxyphenyl)ethyl] 5-[[[3-(2-dimethylaminoethyloxy)-3-oxo-2-phenyl-propyl]amino] methyl]thiophene-2-carboxylate;

[(1S)-2-(3,5-dichloro-1-oxido-pyridin-1-ium-4-yl)-1-(3,4-dimethoxyphenyl)ethyl] 5-[[[2-methyl-3-oxo-2-phenyl-3-[(3R)-quinuclidin-3-yl]oxy-propyl]amino] methyl]thiophene-2-carboxylate;

[(1S)-2-(3,5-dichloro-1-oxido-pyridin-1-ium-4-yl)-1-(3,4-dimethoxyphenyl)ethyl] 5-[[[2-methyl-3-[(1-methyl-4-piperidyl)oxy]-3-oxo-2-phenyl-propyl]amino]methyl]thiophene-2-carboxylate;

[(1S)-2-(3,5-di chloro-1-oxido-pyridin-1-ium-4-yl)-1-(3,4-dimethoxyphenyl)ethyl] 5-[[[3-(2-dimethylaminoethyloxy)-2-methyl-3-oxo-2-phenyl-propyl]amino] methyl]thiophene-2-carboxylate;

[(1S)-2-(3,5-dichloro-1-oxido-pyridin-1-ium-4-yl)-1-(3,4-dimethoxyphenyl)ethyl]-5-[[methyl-[2-methyl-3-oxo-2-phenyl-3-[(3R)-quinuclidin-3-yl] oxy-propyl]amino]methyl]thiophene-2-carboxylate;

Single diastereoisomer of [(1S)-2-(3,5-dichloro-1-oxido-pyridin-1-ium-4-yl)-1-(3,4-dimethoxyphenyl)ethyl] 5-[[[2-hydroxy-3-oxo-3-[(3R)-quinuclidin-3-yl]oxy-2-(2-thienyl)propyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl]-5-[[[3-oxo-2-phenyl-3-[(3R)-quinuclidin-3-yl]oxypropyl]amino]-methyl]thiophene-2-carboxylate (diastereoisomer 1);

Single diastereoisomer 2 of [(1S)-2-(3,5-dichloro-1-oxido-pyridin-1-ium-4-yl)-1-(3,4-dimethoxyphenyl)ethyl]-5-[[[3-oxo-2-phenyl-3-[(3R)-quinuclidin-3-yl]oxypropyl]amino]-methyl]thiophene-2-carboxylate (diastereoisomer 2);

Single diastereoisomer 1 of [(1S)-2-(3,5-dichloro-1-oxido-pyridin-1-ium-4-yl)-1-(3,4-dimethoxyphenyl)ethyl] 5-[[[2-hydroxy-3-oxo-2-phenyl-3-[(3R)-quinuclidin-3-yl]oxy-propyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl] 5-[[[2-hydroxy-3-oxo-2-phenyl-3-[(3R)-quinuclidin-3-yl]oxy-propyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl] 5-[[[3-(2-dimethylaminoethyloxy)-3-oxo-2-phenyl-propyl]amino] methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl] 5-[[[3-(2-dimethylaminoethyloxy)-3-oxo-2-phenyl-propyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl] 5-[[[2-methyl-3-[(1-methyl-4-piperidyl)oxy]-3-oxo-2-phenyl-propyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)ethyl] 5-[[[2-methyl-3-[(1-methyl-4-piperidyl)oxy]-3-oxo-2-phenyl-propyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl] 5-[[methyl-[2-methyl-3-oxo-2-phenyl-3-[(3R)-quinuclidin-3-yl]oxy-propyl]amino] methyl] thiophene-2-carboxylate;

Single diastereoisomer 2 of [(1S)-2-(3,5-dichloro-1-oxido-pyridin-1-ium-4-yl)-1-(3,4-dimethoxyphenyl)ethyl] 5-[[methyl-[2-methyl-3-oxo-2-phenyl-3-[(3R)-quinuclidin-3-yl]oxy-propyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl] 5-[[[3-(2-dimethylaminoethyloxy)-2-methyl-3-oxo-2-phenyl-propyl]amino]methyl]thiophene-2-carboxylate;

Single diastereoisomer 2 of [(1S)-2-(3,5-dichloro-1-oxido-pyridin-1-ium-4-yl)-1-(3,4-dimethoxyphenyl)

ethyl] 5-[[[3-(2-dimethylaminoethyloxy)-2-methyl-3-oxo-2-phenyl-propyl]amino]methyl]thiophene-2-carboxylate;

Single diastereoisomer 1 of [(1S)-2-(3,5-dichloro-1-oxido-pyridin-1-ium-4-yl)-1-(3,4-dimethoxyphenyl)ethyl] 5-[[[2-methyl-3-oxo-2-phenyl-3-[(3R)-quinuclidin-3-yl]oxy-propyl]amino]methyl]thiophene-2-carboxylate; and Single diastereoisomer 2 of [(1S)-2-(3,5-dichloro-1-oxido-pyridin-1-ium-4-yl)-1-(3,4-dimethoxyphenyl)ethyl] 5-[[[2-methyl-3-oxo-2-phenyl-3-[(3R)-quinuclidin-3-yl]oxy-propyl]amino]methyl]thiophene-2-carboxylate.

13. A pharmaceutical composition, comprising a compound, N-oxide, deuterated derivative, or pharmaceutically acceptable salt according to claim 1, in admixture with one or more pharmaceutically acceptable carriers.

14. The pharmaceutical composition according to claim 13, further comprising another active ingredient selected from the group consisting of a beta2-agonist, an antimuscarinic agent, a corticosteroid, a mitogen-activated protein kinase (P38 MAP kinase) inhibitor, a nuclear factor kappa-B kinase subunit beta (IKK2) inhibitor, a human neutrophil elastase (HNE) inhibitor, a phosphodiesterase 4 (PDE4) inhibitor, a leukotriene modulator, a non-steroidal anti-inflammatory agent (NSAID), and a mucus regulator.

15. A method for the prevention treatment of a disease of the respiratory tract characterized by airway obstruction, comprising administering to a subject in need thereof an effective amount of a compound, N-oxide, deuterated derivative, or pharmaceutically acceptable salt according to claim 1, wherein said disease of the respiratory tract is asthma or COPD.

16. The method according to claim 15, wherein said disease of the respiratory tract is asthma.

17. The method according to claim 15, wherein said disease of the respiratory tract is COPD.

* * * * *